(12) United States Patent
Deodhar et al.

(10) Patent No.: US 9,815,782 B2
(45) Date of Patent: Nov. 14, 2017

(54) SUBSTITUTED 3-HALOALLYLAMINE INHIBITORS OF SSAO AND USES THEREOF

(71) Applicant: Boehringer Ingelheim International GmbH, Ingelheim am Rhein (DE)

(72) Inventors: Mandar Deodhar, New South Wales (AU); Alison Dorothy Findlay, New South Wales (AU); Jonathan Stuart Foot, New South Wales (AU); Wolfgang Jarolimek, New South Wales (AU); Ian Alexander Mcdonald, New South Wales (AU); Alan Duncan Robertson, New South Wales (AU); Craig Ivan Turner, New South Wales (AU)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 15/054,243

(22) Filed: Feb. 26, 2016

(65) Prior Publication Data
US 2016/0244406 A1    Aug. 25, 2016

Related U.S. Application Data

(63) Continuation of application No. 14/397,931, filed as application No. PCT/AU2013/000356 on Apr. 5, 2013, now Pat. No. 9,302,986.

(60) Provisional application No. 61/641,814, filed on May 2, 2012.

(51) Int. Cl.
| | | |
|---|---|---|
| A61K 31/165 | (2006.01) |
| C07C 321/26 | (2006.01) |
| C07C 235/46 | (2006.01) |
| C07C 323/62 | (2006.01) |
| C07C 237/30 | (2006.01) |
| C07C 311/37 | (2006.01) |
| C07C 323/63 | (2006.01) |
| C07C 311/29 | (2006.01) |
| C07C 311/16 | (2006.01) |

(52) U.S. Cl.
CPC .......... *C07C 321/26* (2013.01); *C07C 235/46* (2013.01); *C07C 237/30* (2013.01); *C07C 311/16* (2013.01); *C07C 311/29* (2013.01); *C07C 311/37* (2013.01); *C07C 323/62* (2013.01); *C07C 323/63* (2013.01)

(58) Field of Classification Search
None
See application file for complete search history.

(56) References Cited

U.S. PATENT DOCUMENTS

| | | | |
|---|---|---|---|
| 4,454,158 A | 6/1984 | Bey | |
| 4,650,907 A | 3/1987 | Bey et al. | |
| 4,699,928 A | 10/1987 | McDonald | |
| 6,316,652 B1 | 11/2001 | Steliou | |
| 8,110,562 B2 | 2/2012 | Dalton et al. | |
| 2006/0025438 A1 | 2/2006 | Salter-Cid et al. | |
| 2009/0170770 A1 | 7/2009 | Hafezi-Moghadam | |

FOREIGN PATENT DOCUMENTS

| | | |
|---|---|---|
| CA | 2702885 A1 | 4/2009 |
| GB | 2162518 A | 2/1986 |
| WO | 2007005737 A2 | 1/2007 |
| WO | 2007120528 A2 | 10/2007 |
| WO | 2008011072 A2 | 1/2008 |
| WO | 2009051223 A1 | 4/2009 |
| WO | 2009066152 A2 | 5/2009 |
| WO | 2011029996 A1 | 3/2011 |
| WO | 2011113798 A2 | 9/2011 |

OTHER PUBLICATIONS

Foot et al., PXS-4681A, a Potent and Selective Mechanism-Based Inhibitor of SSAO/VAP-1 with Anti-Inflammatory Effects In Vivo, Pharmacological Reviews, vol. 347, No. 2, 2013, pp. 365-374.
International Search Report for corresponding application PCT/AU2013/000356, dated May 8, 2013.
Kim et al., Inactivation of bovine plasma amine oxidase by haloallylamines, Bioorganic & Medicinal Chemistry, 2006, vol. 14, No. 5, pp. 1444-1453.
Marttila-Ichihara et al., Small-Molecule Inhibitors of Vascular Adhesion Protein-1 Reduced the Accumulation of Myeloid Cells into Tumors and Attenute Tumor Growth in Mice, the Journal of Immunology, 2010, vol. 184, No. 6, pp. 3164-3173.
McDonald et al., Semicarbazide Sensitive Amine Oxidas and Vascular Adhesion Protein Being Validated as a Therapeutic Target for Inflammatory Diseases, Annual Reports in Medicinal Chemistry, 2008, vol. 43, pp. 229-241.

(Continued)

*Primary Examiner* — Samantha Shterengarts
(74) *Attorney, Agent, or Firm* — Marc Began; David L. Kershner

(57) ABSTRACT

The present invention is related to the preparation and pharmaceutical use of substituted 3-haloallylamine derivatives as SSAO/VAP-1 inhibitors having the structure of Formula I, as defined in the specification:

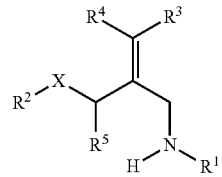

Formula I

The invention also relates to methods of using compounds of Formula I, or pharmaceutically acceptable salt or derivatives thereof, for the treatment of a variety of indications, e.g., inflammatory diseases, ocular diseases, fibrotic diseases, diabetes-induced diseases and cancer.

26 Claims, 22 Drawing Sheets

(56) References Cited

OTHER PUBLICATIONS

O'Rourke et al., Anti-Inflammatory Effects of LJP 1586 [Z-3-Fluoro-2-(4-methoxybenzyl)allylamine Hydrochloride], an Amine-Based Inhibitor of Semicarbazide-Sensitive Amine Oxidase Activity, the Journal of Pharmacology and Experimental Therapeutics, 2008, vol. 324, No. 2, pp. 867-875.

O'Rourke et al., Benefit of inhibiting SSAO in relapsing experimental autoimmune encephalomyelitis, Journal of Neural Transmission, 2007, vol. 114, pp. 845-849.

Wong et al., Semicarbazide-sensitive amine oxidase (SSAO) inhibition ameliorates kidney fibrosis in a unilateral ureteral obstruction murine model, American Journal of Physiology, vol. 307, No. 8, 2014, pp. F908-F916.

Xu et al., Vascular Adhesion Protein-1 Plays an Important Role in Postischemic Inflammation and Neuropathologhy in Diabetic, Estrogen-Treated Ovariectomized Female Rats Subjected to Transient Forebrain Ischemia, Journal Pharmacology and Experimental Therapeutics, 2006, vol. 317, No. 1, pp. 19-29.

Yu et al., Involvement of SSAO-mediated deamination in adipose glucose transport and weight gain in obese diabetic KKAy mice, American Journal of Pysiology Endocrinology and Metabolism, 2004, vol. 286, No. 4, pp. E634-E641.

Toulouse, Amine Oxidase Conference, "In vivo Profile and anti-inflammatory effects of PXS-4681A a potent and selective SSAO/VAP-1 inhibitor", Jul. 2012.

Toulouse, Amine Oxidase Conference, "PXS-4728A, a potent, selective SSAO/VAP-1 inhibitor", Presentation, Jul. 2012.

Bowral, 4th Annual ASI NSW ACT Branch Retreat, "Anti-inflammatory Effects of a potent and selective SSAO-VAP-1 inhibitor", Jul. 2012.

Jarolimek, Division of Chemistry and Structural Biology, "A roller coaster ride—The discovery of SSAO/VAP-1 inhibitor", 2012.

Jarolimek, Department Presentation at Kolling Institute, North Shore Hospital, "Drug Discovery at Pharmaxis a Sydney based life science company", 2012.

Buson, the Inflammation Conference, "Characterization of a selective mechanism based inhibitors for human Semicarbazide-sensitive Amine Oxidase"—Melbourne Nov. 30-Dec. 2, 2012.

Schilter, Australan Society for Immunology 2012: 42nd Annual Meeting, Austraila 2012, "Anti-inflammatory effects of a potent and selective SSAO/VAP-1 inhibitor", 2012. Abstract and Poster.

Becchi, Australian Society for Immunology 2012: 42nd Annual Meeting, Australia, Dec. 2-6, 2012, "Anti-Inflammatory efffects of a potent and selective SSAO/VAP-1 inhibitor". Abstract and Presentation.

Schilter, American Thoracic Society, "Anti-Inflammatory Effects of a potent and Selective SSAO/VAP-1 Inhibitor", 2013.

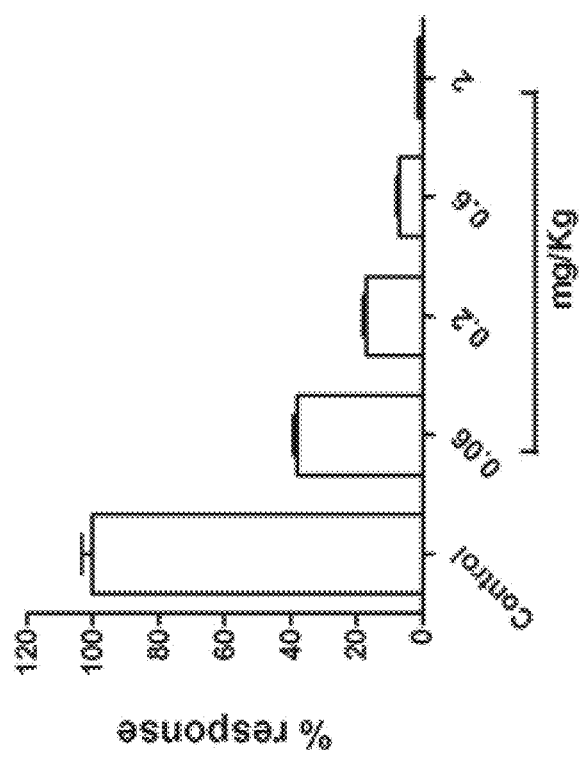
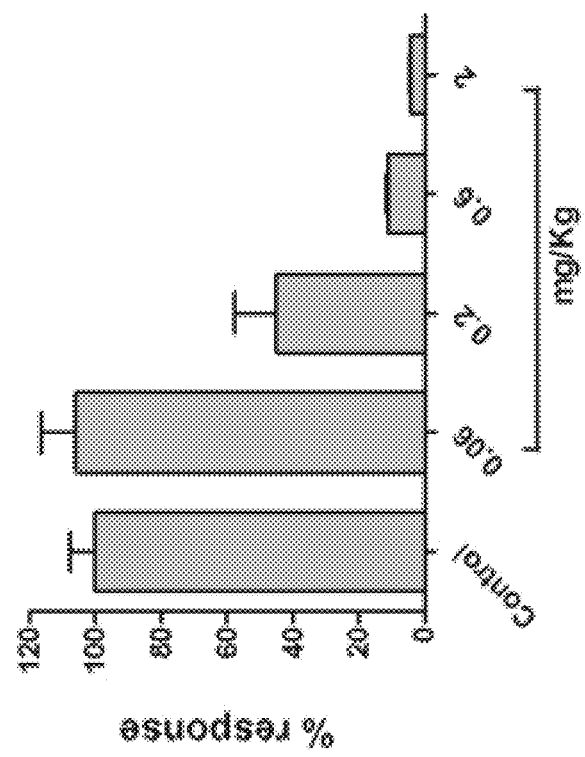
Fig. 1A Abdominal Fat
Fig. 1B Plasma

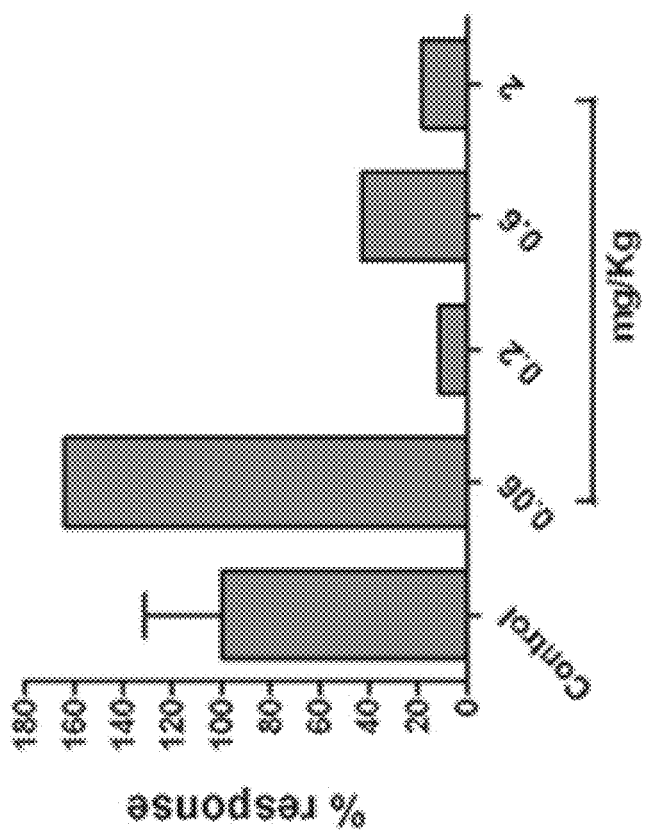
Fig. 1D Aorta
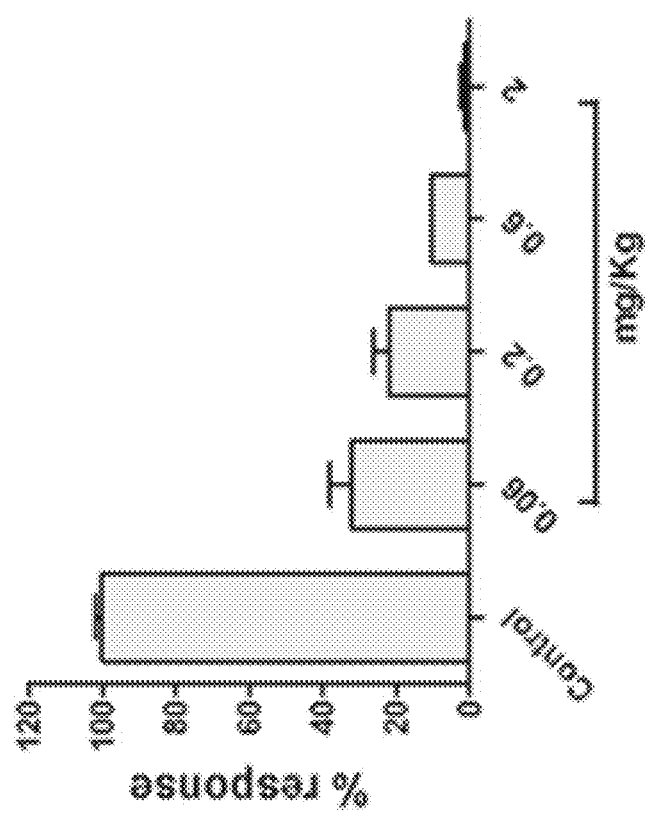
Fig. 1C Lung

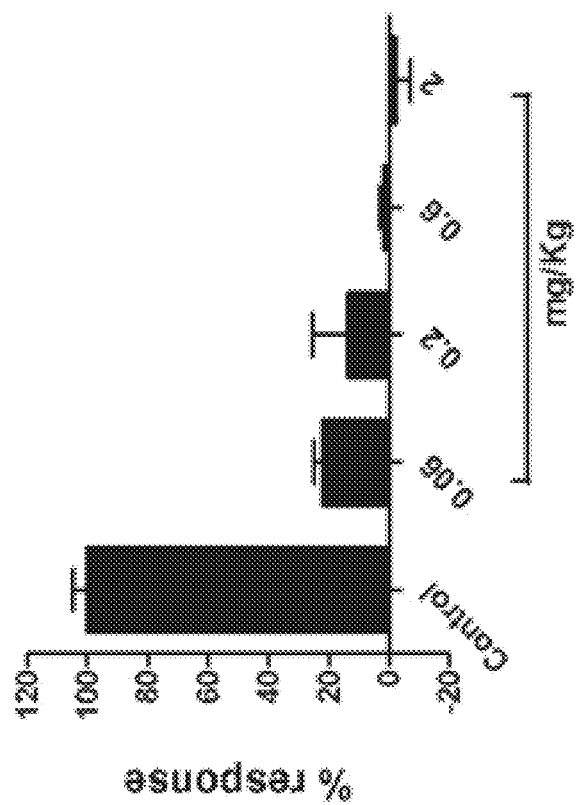

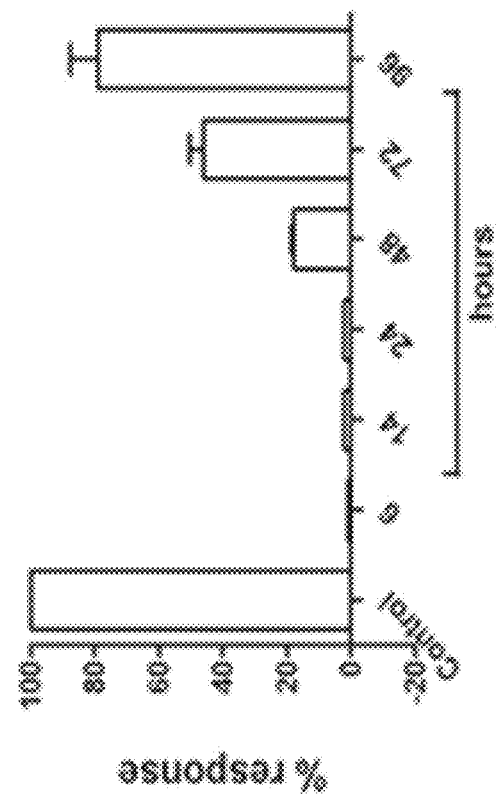
Fig. 2B Plasma
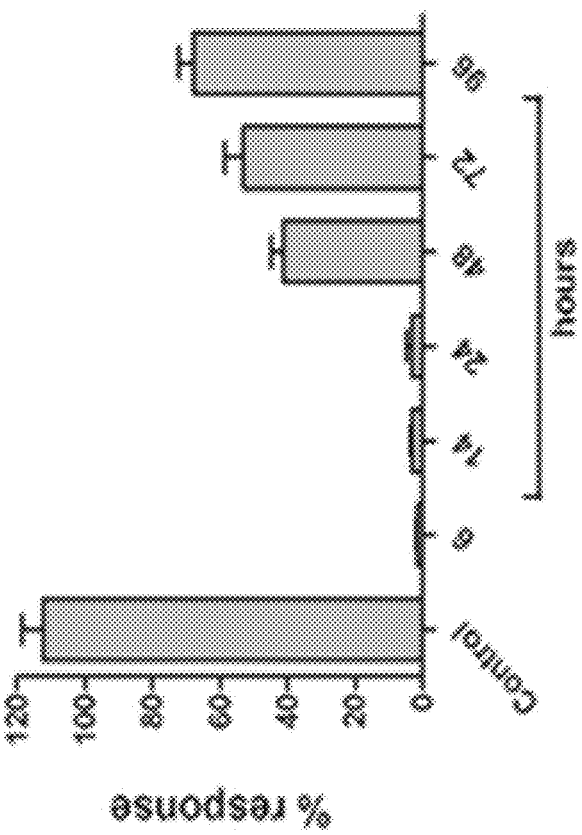
Fig. 2A Abdominal Fat

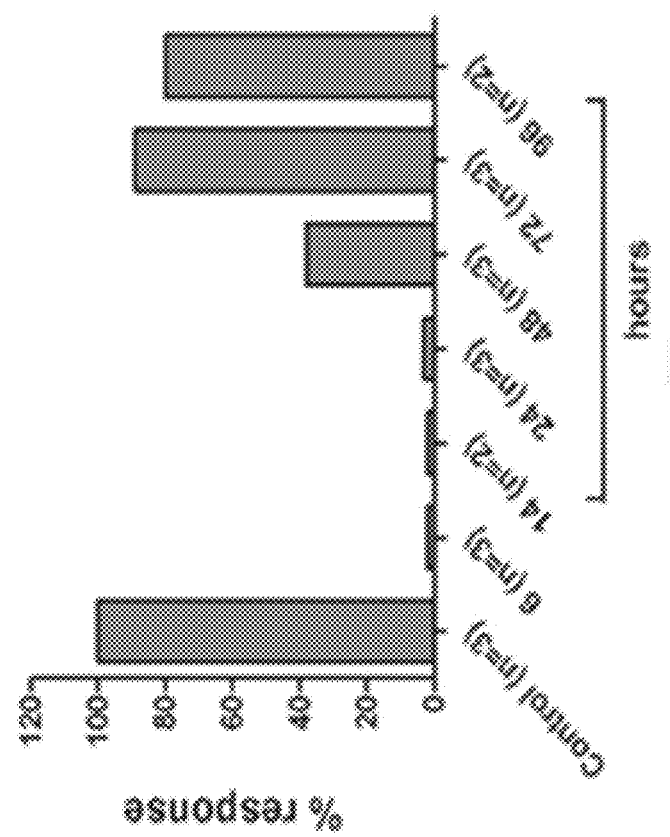
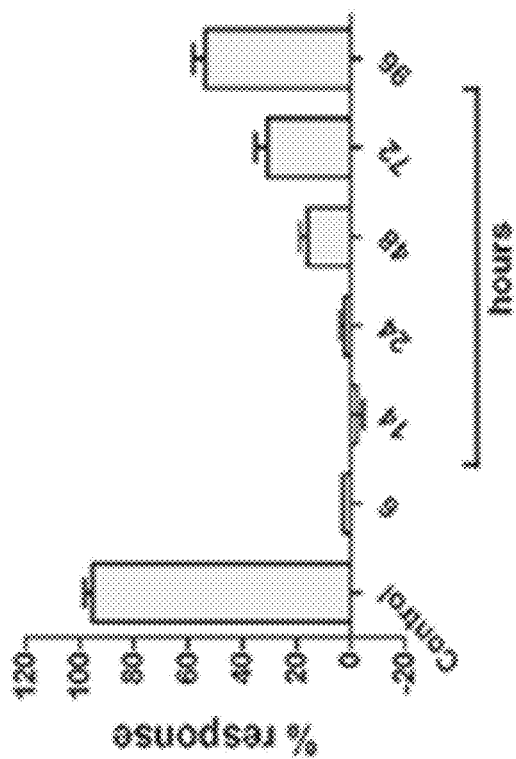
Fig. 2D Aorta
Fig. 2C Lung

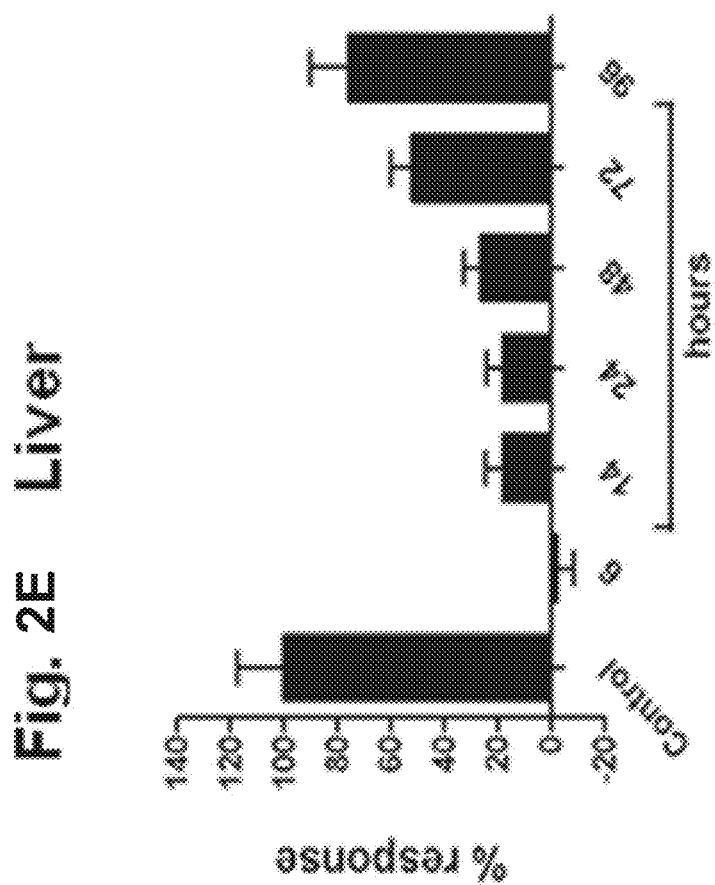

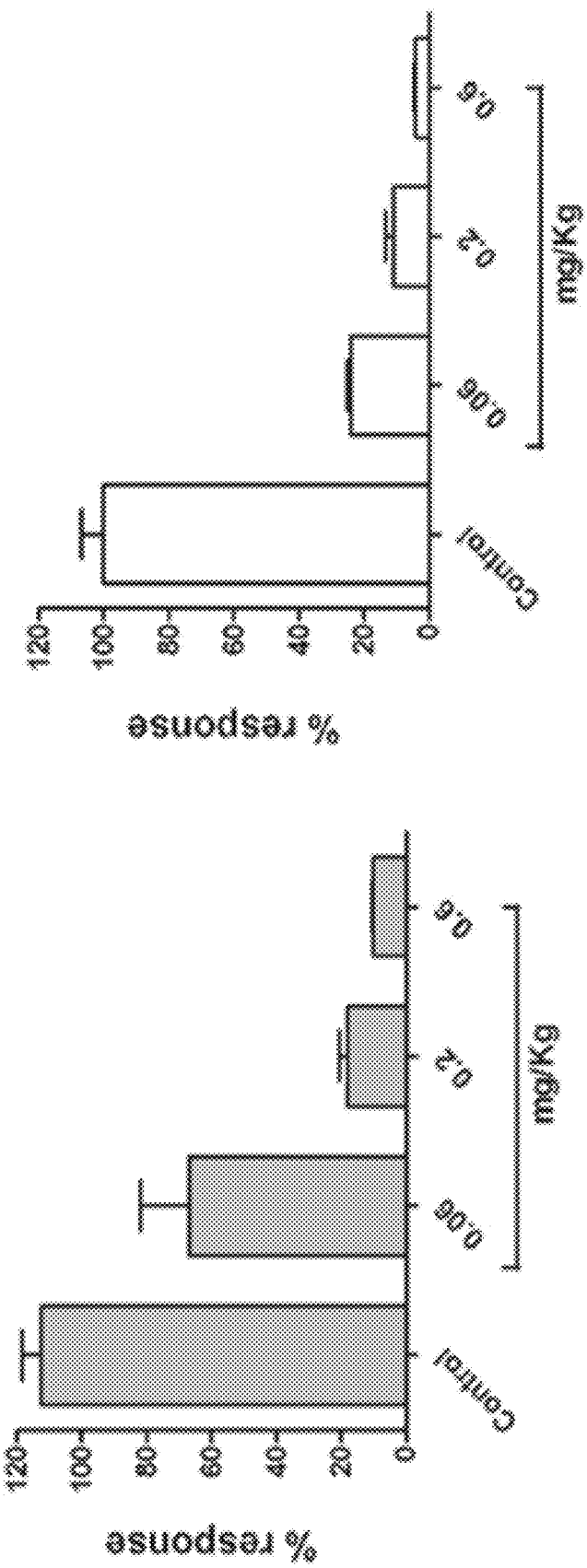

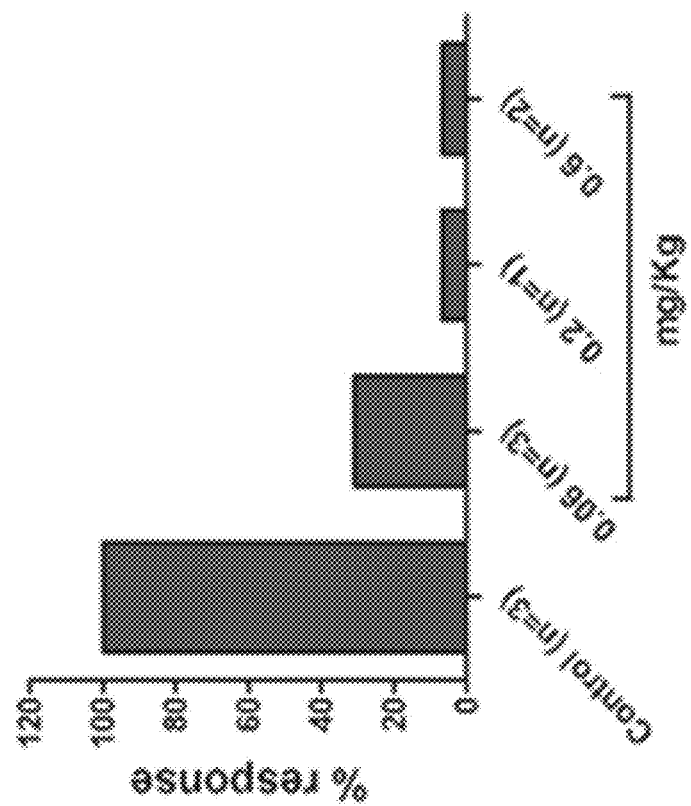
Fig. 3D Aorta
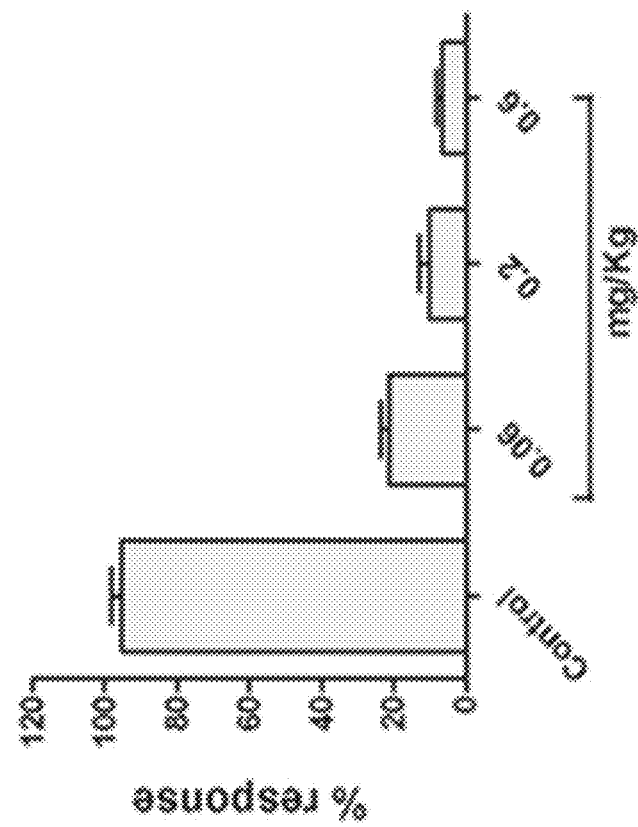
Fig. 3C Lung

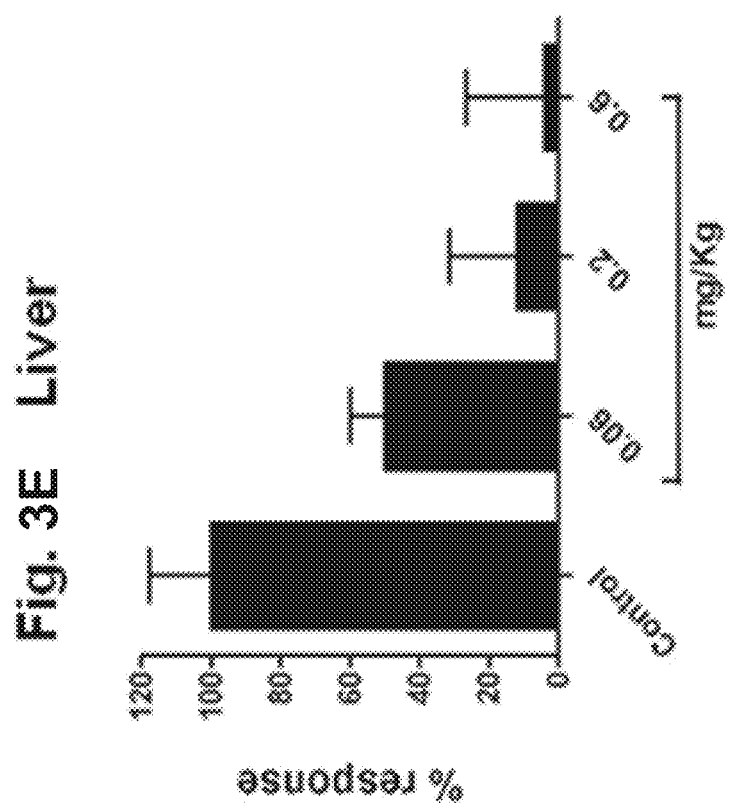

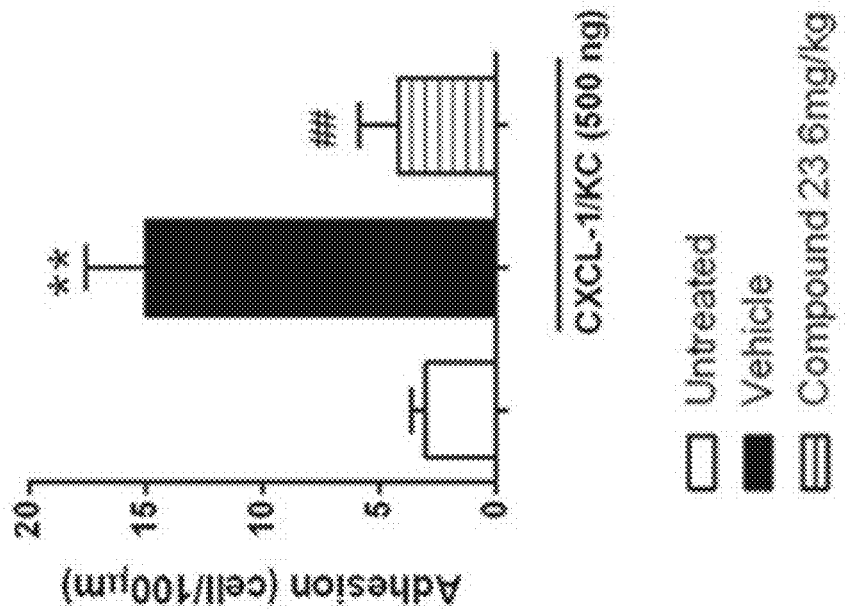
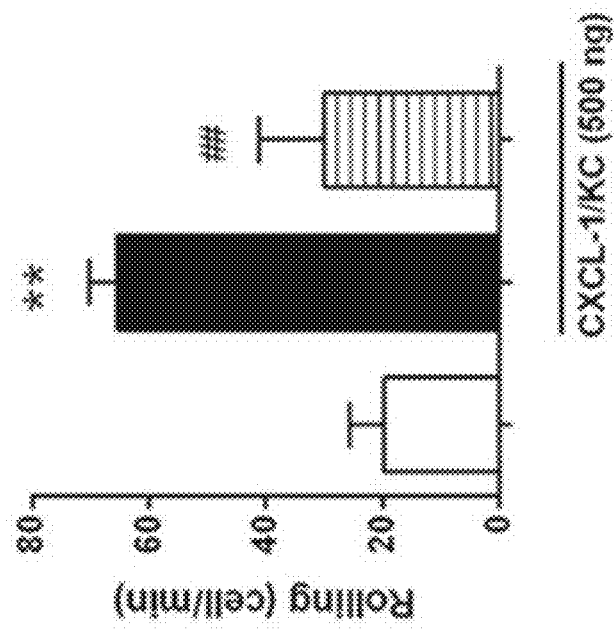
Fig. 5A
Fig. 5B

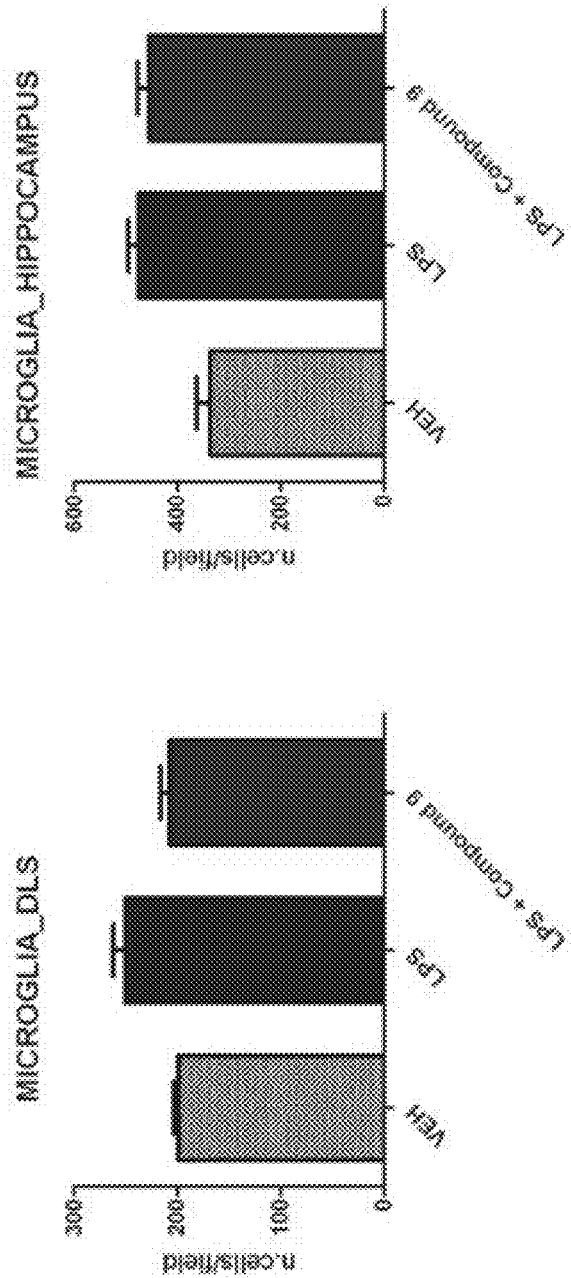

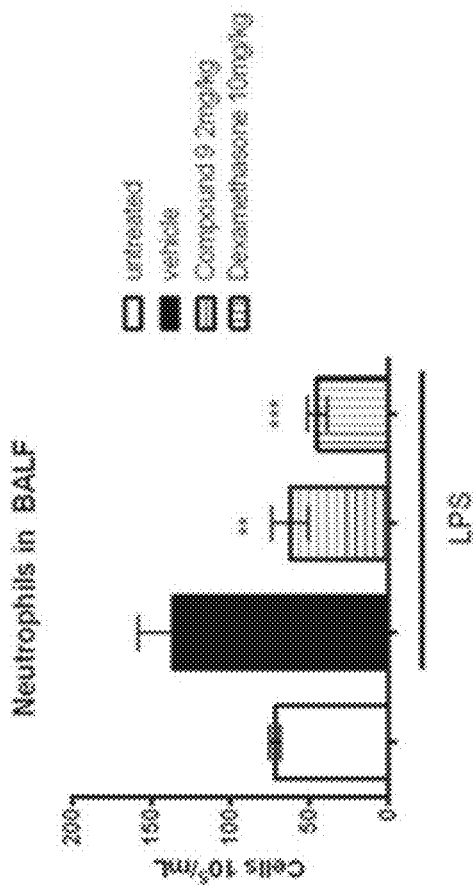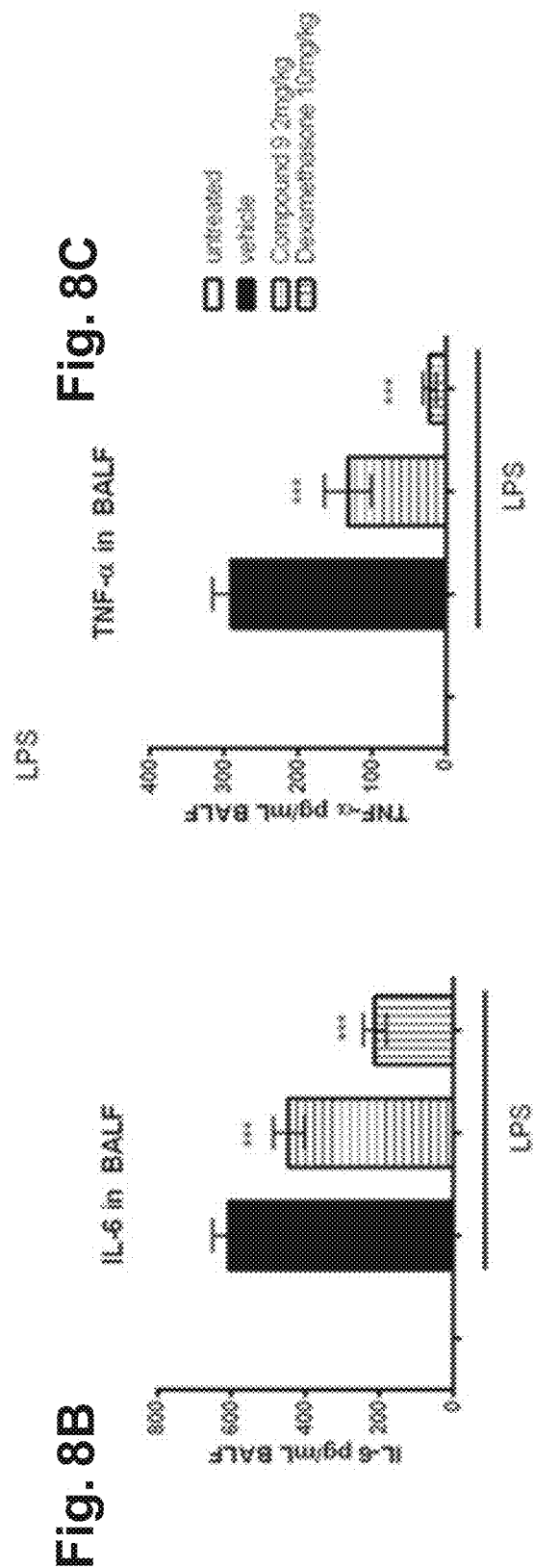

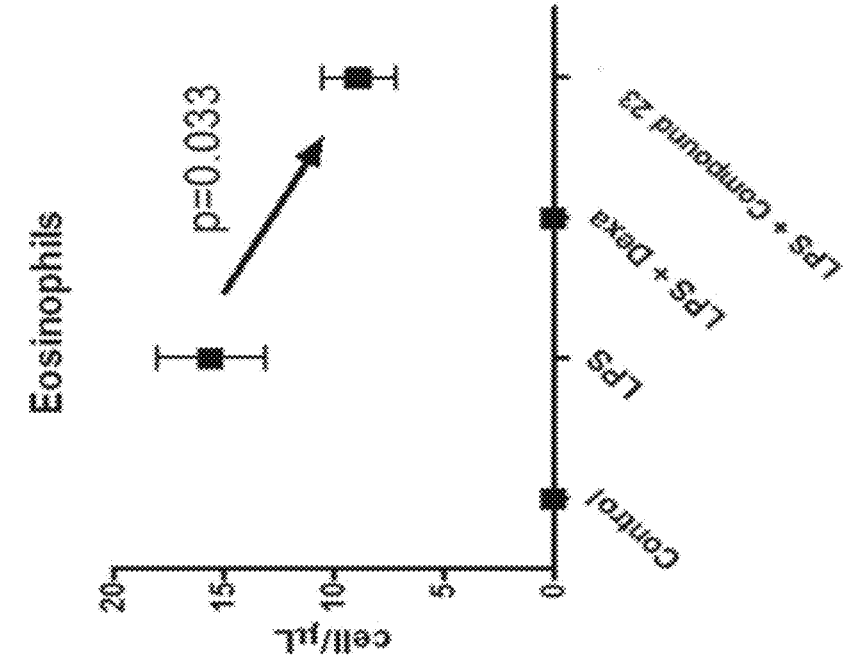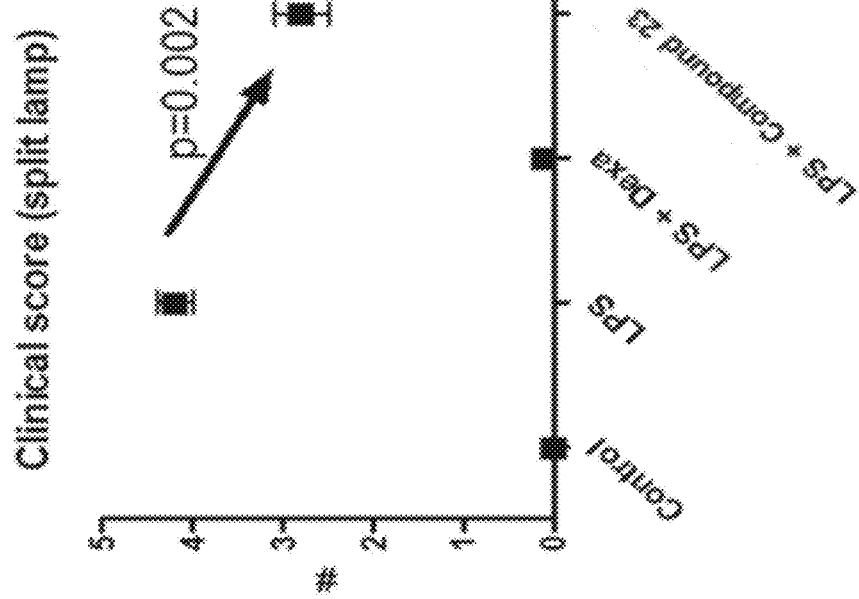

SUBSTITUTED 3-HALOALLYLAMINE INHIBITORS OF SSAO AND USES THEREOF

TECHNICAL FIELD

The present invention relates to novel compounds which are capable of inhibiting certain amine oxidase enzymes. These compounds are useful for treatment of a variety of indications, e.g., the symptoms of inflammation and/or fibrosis in human subjects as well as in pets and livestock, the treatment of psychological diseases, neurodegenerative disorders, and the like. In addition, the present invention relates to pharmaceutical compositions containing these compounds, as well as various uses therefore.

BACKGROUND

Semicarbazide-sensitive amine oxidase (SSAO), also known as primary amine oxidase, plasma amine oxidase and benzylamine oxidase, is identical in structure to vascular adhesion protein-1 (VAP-1). In the following discussion, SSAO/VAP-1 is used to describe this protein. The role of this protein in inflammatory diseases has been reviewed (see, for example, Smith D. J. and Vaino P. J., Targeting Vascular Adhesion Protein-1 to Treat Autoimmune and Inflammatory Diseases. Ann. N.Y. Acad. Sci. 2007, 1110, 382-388; and McDonald I. A. et al., Semicarbazide Sensitive Amine Oxidase and Vascular Adhesion Protein-1: One Protein Being Validated as a Therapeutic Target for Inflammatory Diseases. Annual Reports in Medicinal Chemistry, 2008, 43, 229-241).

In most organisms, including humans, two families of mammalian amine oxidases metabolize various mono-, di-, and polyamines produced endogenously or absorbed from exogenous sources. These include the monoamine oxidases (MAO-A and MAO-B) which are present in the mitochondria of most cell types and use covalently bound flavin adenine dinucleotide (FAD) as the cofactor. Polyamine oxidase is another FAD-dependent amine oxidase which oxidatively deaminates spermine and spermidine. SSAO/VAP-1 belongs to the second family which is dependent on copper and uses other co-factors apart from FAD, such as an oxidized tyrosine residue (abbreviated as TPQ or LTQ). MAO and SSAO/VAP-1 oxidatively deaminate some common substrates which includes the monoamines such as dopamine, tyramine and benzylamine SSAO/VAP-1 also oxidizes endogenous methylamine and aminoacetone.

Some of these enzymes were originally defined by the ability of certain compounds to inhibit the enzymatic activity thereof. For example MAO-A is selectively inhibited by clorgyline, MAO-B by L-deprenyl, while neither clorgyline nor L-deprenyl can inhibit the amine oxidase activity of SSAO/VAP-1. SSAO/VAP-1 can be inhibited by semicarbazide, hence the name semicarbazide sensitive amine oxidase.

SSAO/VAP-1 is an ectoenzyme containing a very short cytoplasmic tail, a single transmembrane domain, and a large, highly glycosylated extracellular domain which contains the active center for the amine oxidase activity. SSAO/VAP-1 is also present in a soluble form circulating in the plasma of some animals. It has been shown that this form is a cleaved product of membrane-bound SSAO/VAP-1.

SSAO/VAP-1 appears to have two physiological functions: the first is the amine oxidase activity mentioned above and the second is cell adhesion activity. Both activities are associated with inflammatory processes. SSAO/VAP-1 was shown to play an important role in extravasation of inflammatory cells from the circulation to sites of inflammation (Salmi M. and Jalkanen S., VAP-1: an adhesin and an enzyme. Trends Immunol. 2001, 22, 211-216). VAP-1 antibodies have been demonstrated to attenuate inflammatory processes by blocking the adhesion site of the SSAO/VAP-1 protein and, together with a substantial body of evidence of in vitro and in vivo knockouts, it is now clear that SSAO/VAP-1 is an important cellular mediator of inflammation. Transgenic mice lacking SSAO/VAP-1 show reduced adhesion of leukocytes to endothelial cells, reduced lymphocyte homing to the lymph nodes and a concomitant attenuated inflammatory response in a peritonitis model. These animals were otherwise healthy, grew normally, were fertile, and examination of various organs and tissues showed the normal phenotype. Furthermore, inhibitors of the amine oxidase activity of SSAO/VAP-1 have been found to interfere with leukocyte rolling, adhesion and extravasation and, similar to SSAO/VAP-1 antibodies, exhibit anti-inflammatory properties.

Inflammation is the first response of the immune system to infection or irritation. The migration of leukocytes from the circulation into tissues is essential for this process. Inappropriate inflammatory responses can result in local inflammation of otherwise healthy tissue which can lead to disorders such as rheumatoid arthritis, inflammatory bowel disease, multiple sclerosis and respiratory diseases. Leukocytes first adhere to the endothelium via binding to adhesion molecules before they can start the process of passing through the walls of the blood vessels. Membrane bound SSAO/VAP-1 is abundantly expressed in vascular endothelial cells such as high venule endothelial cells (HVE) of lymphatic organs and is also expressed in hepatic sinusoidal endothelial cells (HSEC), smooth muscle cells and adipocytes. The expression of SSAO/VAP-1 on the cell surface of endothelial cells is tightly regulated and is increased during inflammation. In the presence of an SSAO/VAP-1 substrate (benzylamine), NFκB was activated in HSECs together with up-regulation of other adhesion molecules, E-selectin and chemokine CXCL8 (IL-8) in vitro. A recent study confirms this result by showing (by mutagenesis) that the transcription and translation of E-selectin and P-selectin is induced by the enzyme activity of SSAO/VAP-1. These results suggest an important role of the amine oxidase activity of SSAO/VAP-1 in the inflammatory response. It has been reported that the oxidase activity of SSAO/VAP-1 induces endothelial E- and P-selectins and leukocyte binding (Jalkanen, S. et al., The oxidase activity of vascular adhesion protein-1 (VAP-1) induces endothelial E- and P-selectins and leukocyte binding. Blood 2007, 110, 1864-1870).

Excessive and chronic inflammatory responses have been associated with the symptoms of many chronic diseases, such as rheumatoid arthritis, multiple sclerosis, asthma and chronic obstructive pulmonary disease (COPD). Patients suffering from either atopic eczema or psoriasis (both chronic inflammatory skin disorders) have higher levels of SSAO/VAP-1 positive cells in their skin compared to skin from healthy controls.

Asthma can be considered a disease resulting from chronic inflammation of the airways which results in bronchoconstriction and excessive build-up of mucus. Many patients can be adequately treated with bronchodilators (eg, β2 agonists, leukotriene antagonists and with inhaled steroids). However, up to about 20% of patients suffer from severe asthma and don't respond well to these treatments. A subset of these patients are resistant to inhaled steroids and present with high neutrophil counts in their lung fluids. SSAO/VAP-1 is expressed in the lungs and plays a role in the trafficking of neutrophils.

Another subset of asthma patients is acutely sensitive to viral infections of the airways; such infections exacerbate the underlying inflammation and can lead to severe asthma attacks.

It has been recently recognized that patients suffering from cystic fibrosis frequently suffer from persistent lung inflammation which can be independent from chronic lung infection. It has been argued that tissue damage in cystic fibrosis patients is due to mediators released by neutrophils. While standard antibiotic treatment to clear bacterial infection would be expected to resolve the underlying inflammation if the inflammation were solely due to the infection, data from recent studies demonstrate that this is not the case and that the airways are in a neutrophil-driven pro-inflammatory state primed for excessive and prolonged inflammatory response to bacterial infection. See Rao S. and Grigg J., New insights into pulmonary inflammation in cystic fibrosis. *Arch Dis Child* 2006, 91:786-788.

SSAO/VAP-1 is also highly expressed in adipocytes where it plays a role in glucose transport independent of the presence of insulin. It has been observed that levels of plasma SSAO/VAP-1 are increased in patients suffering from diabetes. Elevated levels of plasma SSAO/VAP-1 have been found in patients suffering from other illnesses, such as congestive heart failure and liver cirrhosis. It has been suggested that SSAO/VAP-1 is associated with most, if not all, inflammatory diseases whether the inflammation is in response to an immune response or subsequent to other events such as occlusion and reperfusion of blood vessels.

It has been recognized in recent years that SSAO/VAP-1 is expressed in sinusoidal endothelial cells in the liver and that this protein is believed to be associated with hepatic disease, in particular liver fibrosis (Weston C. J. and Adams D. H., Hepatic consequences of vascular adhesion protein-1 expression, *J Neural Transm* 2011; 118:1055-1064). Furthermore, a VAP-1 antibody and a small molecule inhibitor were found to attenuate carbon tetrachloride induced fibrosis in mice. Thus, SSAO/VAP-1 inhibitors have the potential to treat fibrotic disease (WO 2011/029996). It has been recently reported that oxidation of methylamine by SSAO/VAP-1 in the presence of tumor necrosis factor α induces the expression of MAdCAM-1 in hepatic vessels, and that this is associated with the hepatic complications of inflammatory bowel disease (IBD) (Liaskou W. et al., Regulation of Mucosal Addressin Cell Adhesion Molecule 1 Expression in Human and Mice by Vascular Adhesion Protein 1 Amine Oxidase Activity, *Hepatology* 2011; 53, 661-672).

It has been reported that SSAO/VAP-1 inhibitors can attenuate angiogenesis and lymphangiogenesis, and that these inhibitors offer potential to treat ocular diseases such as macular degeneration, corneal angiogenesis, cataracts, and inflammatory conditions such as uveitis (US 2009/0170770; WO 2009/051223; Noda K., et al, Inhibition of vascular adhesion protein-1 suppresses endotoxin-induced uveitis, *FASEB J.* 2008, 22, 1094-1103).

Increased levels of SSAO/VAP-1 were observed in the serum of patients suffering from hepatocellular carcinoma. In a murine melanoma model, small molecule SSAO/VAP-1 inhibitors were shown to retard tumor growth, in contrast to VAP-1 antibodies which had no activity (Weston C. J. and Adams D. H., Hepatic consequences of vascular adhesion protein-1 expression, *J Neural Transm* 2011, 118, 1055-1064).

It was reported that SSAO/VAP-1 plays an important role in cancer biology (Marttila-Ichihara F. et al. Small-Molecule Inhibitors of Vascular Adhesion Protein-1 Reduce the Accumulation of Myeloid Cells into Tumors and Attenuate Tumor Growth in Mice. *The Journal of Immunology,* 2010, 184, 3164-3173). SSAO/VAP-1 small molecule inhibitors reduced the number of proangiogenic Gr-1+CD11b+ myeloid cells in melanomas and lymphomas.

During the SSAO/VAP-1 amine oxidase catalytic cycle the covalently bound cofactor, TPQ, is first reduced, and then re-oxidized by oxygen in the presence of copper with the generation of hydrogen peroxide as a by-product. It has been speculated that excessive hydrogen peroxide concentrations can be deleterious and may contribute to the pathology of various inflammatory and neurodegenerative processes (Götz M. E., et al., Oxidative stress: Free radical production in neural degeneration. *Pharmacol Ther* 1994, 63, 37-122).

Inflammation is believed to be an important feature of neurodegenerative diseases such as Parkinson's disease, Alzheimer's disease and multiple sclerosis, and similarly is a feature of the pathophysiology that occurs after a cerebral occlusion/reperfusion event (Aktas, O. et al., Neuronal damage in brain inflammation. *Arch Neurol* 2007, 64, 185-9). Excessive activity SSAO/VAP-1 has been independently implicated in these processes (Xu, H-L., et al., Vascular Adhesion Protein-1 plays an important role in postischemic inflammation and neuropathology in diabetic, estrogen-treated ovariectomized female rats subjected to transient forebrain ischemia. *Journal Pharmacology and Experimental Therapeutics,* 2006, 317, 19-26).

Some known MAO inhibitors also inhibit SSAO/VAP-1 (e.g., the MAO-B inhibitor Mofegiline illustrated below). Mofegiline has been reported to inhibit experimental autoimmune encephalomyelitis (US 2006/0025438 A1). This inhibitor is a member of the haloallylamine family of MAO inhibitors; the halogen in Mofegiline is fluorine. Fluoroallylamine inhibitors are described in U.S. Pat. No. 4,454,158. There have been reports of a chloroallylamine, MDL72274 (illustrated below), selectively inhibiting rat SSAO/VAP-1 compared to MAO-A and MAO-B:

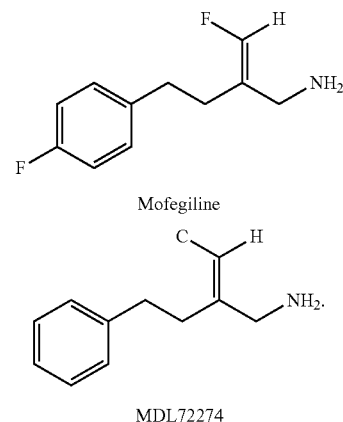

Additional fluoroallylamine inhibitors are described in U.S. Pat. No. 4,699,928; the two compounds illustrated below were described as selective inhibitors of MAO-B:

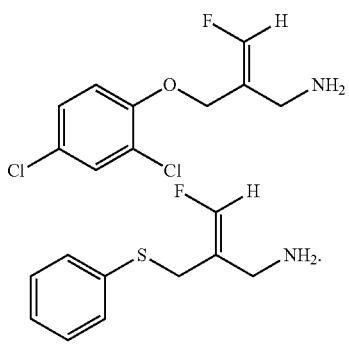

Other examples structurally related to Mofegiline can be found in WO 2007/120528.

Haloallylamine compounds that differ from Mofegiline in core structure have been synthesized and were shown to inhibit the amine oxidase activity from copper-dependent amine oxidases from a number of species (see Kim J., et al., Inactivation of bovine plasma amine oxidase by haloallylamines *Bioorg Med Chem* 2006, 14, 1444-1453). These compounds have been included in a patent application (WO 2007/005737):

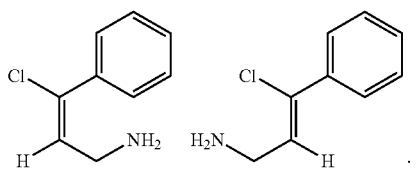 [SMILES: NC/C=C(/Cl)c1ccccc1 ; NC/C=C(\Cl)c1ccccc1]

WO 2009/066152 describes a family of 3-substituted 3-haloallylamines that are inhibitors of SSAO/VAP-1 and are claimed as treatment for a variety of indications, including inflammatory disease. The following compounds are specifically described:

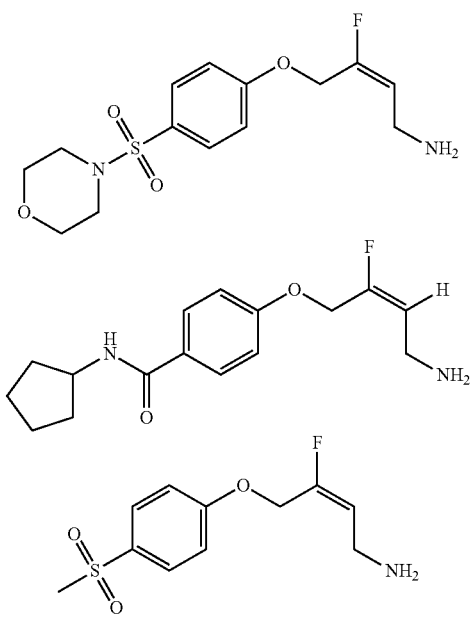

References to the effects of SSAO/VAP-1 inhibitors in various animal models of disease can be found in the review publication by McDonald I. A. et al., Semicarbazide Sensitive Amine Oxidase and Vascular Adhesion Protein-1: One Protein Being Validated as a Therapeutic Target for Inflammatory Diseases. *Annual Reports in Medicinal Chemistry,* 2008, 43, 229-241 and in the following publications, O'Rourke A. M. et al., Anti-inflammatory effects of LJP 1586 [Z-3-fluoro-2-(4-methoxybenzyl)allylamine hydrochloride], an amine-based inhibitor of semicarbazide-sensitive amine oxidase activity. *J. Pharmacol. Exp. Ther.,* 2008, 324, 867-875; and O'Rourke A. M. et al., Benefit of inhibiting SSAO in relapsing experimental encephalomyelitis. *J. Neural. Transm.,* 2007, 114, 845-849.

SUMMARY

The present invention provides substituted haloallylamine compounds that inhibit SSAO/VAP-1. Surprisingly, modification of 2-substituted-3-haloallylamine structures described previously has led to the development of novel compounds that are potent inhibitors of the human SSAO/VAP-1 enzyme and which have much improved pharmacological and safety properties. These compounds are very potent on SSAO/VAP-1 and were surprisingly found to be very weak inhibitors of other family members, such as monoamine oxidase A, monoamine oxidase B, diamine oxidase, lysyl oxidase, and lysyl-like amine oxidases LOX1-4.

A first aspect of the invention provides for a compound of Formula I:

Formula I or a stereoisomer, pharmaceutically acceptable salt, polymorphic form, solvate or prodrug thereof; wherein:

R[1] and R[4] are independently hydrogen or optionally substituted $C_{1-6}$alkyl;

R[2] and R[3] are independently selected from the group consisting of hydrogen, chlorine and fluorine; provided, however, that R[2] and R[3] are not hydrogen at the same time;

R[5] is an optionally substituted arylene group;

R[6] is selected from

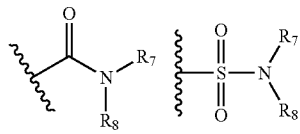

R[7] and R[8] are independently selected from the group consisting of hydrogen, optionally substituted $C_{1-6}$alkyl and optionally substituted $C_{3-7}$cycloalkyl; and X is $CH_2$, oxygen, sulfur or $SO_2$.

A second aspect of the invention provides for a pharmaceutical composition comprising a compound according to the first aspect of the invention, or a pharmaceutically acceptable salt or solvate thereof, and at least one pharmaceutically acceptable excipient, carrier or diluent.

A third aspect of the invention provides for a method of inhibiting the amine oxidase activity of SSAO/VAP-1 in a subject in need thereof, said method comprising administering to said subject an effective amount of a compound according to the first aspect of the invention, or a pharmaceutically acceptable salt or solvate thereof, or a composition according to the second aspect of the invention.

A fourth aspect of the invention provides for a method of treating a disease associated with or modulated by SSAO/VAP-1 protein, said method comprising administering to a subject in need thereof a therapeutically effective amount of a compound according to the first aspect of the invention, or a pharmaceutically acceptable salt or solvate thereof, or a composition according to the second aspect of the invention.

A fifth aspect of the invention provides for a method of treating a disease associated with or modulated by SSAO/VAP-1, said method comprising administering to a subject in need thereof a therapeutically effective amount of a compound according to the first aspect of the invention, or a pharmaceutically acceptable salt or solvate thereof, or a composition according to the second aspect of the invention.

A sixth aspect of the invention provides for use of a compound according to the first aspect of the invention, or a pharmaceutically acceptable salt or solvate thereof, for the manufacture of a medicament for treating a disease associated with or modulated by SSAO/VAP-1 protein.

A seventh aspect of the invention provides for a compound according to the first aspect of the invention, or a pharmaceutically acceptable salt or solvate thereof, for use in treating a disease associated with or modulated by SSAO/VAP-1 protein.

In another aspect, the present invention describes the synthesis and use of compounds which inhibit the amine oxidase activity of SSAO/VAP-1, and describes the use of such inhibitors to treat patients suffering inflammatory diseases.

The compounds of the present invention are useful for the treatment of the symptoms of inflammation and/or fibrosis in human subjects as well as in pets and livestock. Human inflammatory diseases contemplated for treatment herein include arthritis, Crohn's disease, irritable bowel disease, psoriasis, eosinophilic asthma, severe asthma, virally exacerbated asthma, chronic pulmonary obstructive disease, cystic fibrosis, bronchiectasis, atherosclerosis, inflammation due to diabetes, inflammatory cell-mediated tissue destruction following stroke, and the like. Human fibrotic diseases and disorders contemplated for treatment herein include idiopathic pulmonary fibrosis or other interstitial lung diseases, liver fibrosis, kidney fibrosis, fibrosis of other organs and tissues, radiation induced fibrosis, and the like.

The compounds of the present invention are also useful for the treatment of bacteria-induced lung inflammation associated with cystic fibrosis. Treatment can be both prophylactic and therapeutic. Furthermore, the compounds of the present invention are useful for the treatment of other bacteria-induced lung diseases such as sepsis, acute respiratory distress syndrome (ARDS), acute lung injury (ALI), transfusion induced lung injury (TRALI), and the like.

The compounds of the present invention are also useful for the treatment of ocular diseases, such as uveitis and macular degeneration.

The compounds of the present invention are also useful as an adjunct therapy to treat cancer. In combination with standard and novel chemotherapeutic agents, the compounds of the present invention can lead to better control of the cancer, and to help reduce metastatic secondary cancers.

Since SSAO/VAP-1 small molecule inhibitors actively attenuate neutrophil levels in the lipopolysaccharide (LPS) mouse model of lung neutrophilia, such molecules have the potential to treat steroid resistant asthma in human subjects. Accordingly, in accordance with one aspect of the present invention, there are provided methods for treating patients with an inhibitor of SSAO/VAP-1 either as a prophylactic or therapeutic agent to reduce neutrophil levels and treat the symptoms of severe asthma.

In accordance with another aspect of the present invention, there are provided methods for treating patients with an inhibitor of SSAO/VAP-1 either as a prophylactic agent or as a therapeutic agent to treat on-going disease.

In accordance with still another aspect of the present invention, there are provided methods for the use of an SSAO/VAP-1 inhibitor to modulate the concentration of neutrophils in the airways and to treat the underlying cause of inflammation in patients suffering from inflammation of the airways.

In accordance with yet another aspect of the present invention, there are provided methods for treating patients suffering from liver fibrosis with an SSAO/VAP-1 inhibitor.

In accordance with a further aspect of the present invention, there are provided methods for treating patients suffering from ocular disease with an SSAO/VAP-1 inhibitor to treat symptoms of the disease.

Since SSAO/VAP-1 is expressed in various cancer types, in accordance with yet another aspect of the present invention, there is contemplated the use of SSAO/VAP-1 inhibitors as adjunctive therapy to treat patients suffering from cancers which express SSAO/VAP-1.

In one embodiment of the methods and uses of the present invention the disease is inflammation. In another embodiment the inflammation is associated with liver disease. In a further embodiment the inflammation is associated with respiratory disease. In a still further embodiment the inflammation is associated with cystic fibrosis. In another embodiment the inflammation is associated with asthma or chronic obstructive pulmonary disease. In a further embodiment the inflammation is associated with ocular disease.

In one embodiment of the methods and uses of the present invention the disease is a diabetes-induced disease selected from the group consisting of diabetic nephropathy, glomerulosclerosis, diabetic retinopathy, non-alcoholic fatty liver disease and choroidal neovascularisation.

In another embodiment of the methods and uses of the present invention the disease is a neuroinflammatory disease. In a further embodiment of the methods and uses of the present invention the disease is selected from the group consisting of liver fibrosis, liver cirrhosis, kidney fibrosis, idiopathic pulmonary fibrosis and radiation-induced fibrosis. In a still further embodiment of the methods and uses of the present invention the disease is cancer.

DEFINITIONS

The following are some definitions that may be helpful in understanding the description of the present invention. These are intended as general definitions and should in no way limit the scope of the present invention to those terms alone, but are put forth for a better understanding of the following description.

Unless the context requires otherwise or specifically stated to the contrary, integers, steps, or elements of the invention recited herein as singular integers, steps or elements clearly encompass both singular and plural forms of the recited integers, steps or elements.

Throughout this specification, unless the context requires otherwise, the word "comprise", or variations such as "comprises" or "comprising", will be understood to imply the inclusion of a stated step or element or integer or group of steps or elements or integers, but not the exclusion of any other step or element or integer or group of elements or integers. Thus, in the context of this specification, the term "comprising" means "including principally, but not necessarily solely".

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

As used herein, the term "alkyl" includes within its meaning monovalent ("alkyl") and divalent ("alkylene") straight chain or branched chain saturated hydrocarbon radicals having from 1 to 6 carbon atoms, e.g., 1, 2, 3, 4, 5 or 6 carbon atoms (unless specifically defined). The straight chain or branched alkyl group is attached at any available point to produce a stable compound. In many embodiments, a lower alkyl is a straight or branched alkyl group containing from 1-6, 1-4, or 1-2, carbon atoms. For example, the term alkyl includes, but is not limited to, methyl, ethyl, 1-propyl, isopropyl, 1-butyl, 2-butyl, isobutyl, tert-butyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, and the like.

The term "alkoxy" as used herein refers to straight chain or branched alkyloxy (i.e., O-alkyl) groups, wherein alkyl is as defined above. Examples of alkoxy groups include methoxy, ethoxy, n-propoxy, and isopropoxy The term "cycloalkyl" as used herein includes within its meaning monovalent ("cycloalkyl") and divalent ("cycloalkylene") saturated, monocyclic, bicyclic, polycyclic or fused analogs. In the context of the present disclosure the cycloalkyl group may have from 3 to 10 or from 3 to 7 carbon atoms A fused analog of a cycloalkyl means a monocyclic ring fused to an aryl or heteroaryl group in which the point of attachment is on the non-aromatic portion. Examples of cycloalkyl and fused analogs thereof include cyclopropyl, cyclobutyl, cyclopentyl, cyclohexyl, cycloheptyl, tetrahydronaphthyl, decahydronaphthyl, indanyl, and the like.

The term "aryl" or variants such as "arylene" as used herein refers to monovalent ("aryl") and divalent ("arylene") single, polynuclear, conjugated and fused analogs of aromatic hydrocarbons having from 6 to 10 carbon atoms. A fused analog of aryl means an aryl group fused to a monocyclic cycloalkyl or monocyclic heterocyclyl group in which the point of attachment is on the aromatic portion. Examples of aryl and fused analogs thereof include phenyl, naphthyl, indanyl, indenyl, tetrahydronaphthyl, 2,3-dihydrobenzofuranyl, dihydrobenzopyranyl, 1,4-benzodioxanyl, and the like. Examples of an arylene include phenylene and natpthylene. A "substituted aryl" is an aryl that is independently substituted, with one or more, preferably 1, 2 or 3 substituents, attached at any available atom to produce a stable compound. A "substituted arylene" is an arylene that is independently substituted, with one or more, preferably 1, 2 or 3 substituents, attached at any available atom to produce a stable compound.

The term "alkylaryl" as used herein, includes within its meaning monovalent ("aryl") and divalent ("arylene"), single, polynuclear, conjugated and fused aromatic hydrocarbon radicals attached to divalent, saturated, straight or branched chain alkylene radicals. Examples of alkylaryl groups include, but are not limited to, benzyl.

The term "heteroaryl" refers to a monocyclic aromatic ring structure containing 5 or 6 ring atoms, wherein heteroaryl contains one or more heteroatoms independently selected from the group consisting of O, S, and N. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable compound is produced. Examples of heteroaryl groups include, but are not limited to, pyridinyl, pyridazinyl, pyrazinyl, quinaoxalyl, indolizinyl, benzo[b]thienyl, quinazolinyl, purinyl, indolyl, quinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, and indolyl. "Nitrogen containing heteroaryl" refers to heteroaryl wherein any heteroatoms are N. A "substituted heteroaryl" is a heteroaryl that is independently substituted, with one or more, preferably 1, 2 or 3 substituents, attached at any available atom to produce a stable compound.

"Heteroarylene" refers to a divalent, monocyclic aromatic ring structure containing 5 or 6 ring atoms, wherein heteroarylene contains one or more heteroatoms independently selected from the group consisting of O, S, and N. Heteroarylene is also intended to include oxidized S or N, such as sulfinyl, sulfonyl and N-oxide of a tertiary ring nitrogen. A carbon or nitrogen atom is the point of attachment of the heteroarylene ring structure to the substituents thereon, such that a stable compound is produced. Examples of heteroaryl groups include, but are not limited to, pyridinylene, pyridazinylene, pyrazinylene, quinaoxalylene, indolizinylene, benzo[b]thienylene, quinazolinylene, purinylene, indolylene, quinolinylene, pyrimidinylene, pyrrolylene, oxazolylene, thiazolylene, thienylene, isoxazolylene, oxathiadiazolylene, isothiazolylene, tetrazolylene, imidazolylene, triazinylene, furanylene, benzofurylene, and indolylene. "Nitrogen containing heteroarylene" refers to heteroarylene wherein any heteroatoms are N. A "substituted heteroarylene" is a heteroarylene that is independently substituted, with one or more, preferably 1, 2 or 3 substituents, attached at any available atom to produce a stable compound.

The term "heterocyclyl" and variants such as "heterocycloalkyl" as used herein, includes within its meaning monovalent ("heterocyclyl") and divalent ("heterocyclylene"), saturated, monocyclic, bicyclic, polycyclic or fused hydrocarbon radicals having from 3 to 10 ring atoms, wherein from 1 to 5, or from 1 to 3, ring atoms are heteroatoms independently selected from O, N, NH, or S, in which the point of attachment may be carbon or nitrogen. A fused analog of heterocyclyl means a monocyclic heterocycle fused to an aryl or heteroaryl group in which the point of attachment is on the non-aromatic portion. The heterocyclyl group may be $C_{3-8}$ heterocyclyl. The heterocycloalkyl group may be $C_{3-6}$ heterocyclyl. The heterocyclyl group may be $C_{3-5}$ heterocyclyl. Examples of heterocyclyl groups and fused analogs thereof include aziridinyl, pyrrolidinyl, thiazolidinyl, piperidinyl, piperazinyl, imidazolidinyl, 2,3-dihydrofuro(2,3-b)pyridyl, benzoxazinyl, tetrahydroquinolinyl, tetrahydroisoquinolinyl, dihydroindolyl, quinuclidinyl, azetidinyl, morpholinyl, tetrahydrothiophenyl, tetrahydrofuranyl, tetrahydropyranyl, and the like. The term also includes partially unsaturated monocyclic rings that are not aromatic, such as 2- or 4-pyridones attached through the nitrogen or N-substituted uracils.

The term "halogen" or variants such as "halide" or "halo" as used herein refers to fluorine, chlorine, bromine and iodine.

The term "heteroatom" or variants such as "hetero-" or "heterogroup" as used herein refers to O, N, NH and S.

In general, "substituted" refers to an organic group as defined herein (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents.

The term "optionally substituted" as used herein means the group to which this term refers may be unsubstituted, or may be substituted with one or more groups independently selected from alkyl, alkenyl, alkynyl, cycloalkyl, cycloalkenyl, heterocycloalkyl, halo, haloalkyl, haloalkynyl, hydroxyl, hydroxyalkyl, alkoxy, thioalkoxy, alkenyloxy, haloalkoxy, haloalkenyloxy, $NO_2$, NH(alkyl), N(alkyl)$_2$, nitroalkyl, nitroalkenyl, nitroalkynyl, nitroheterocyclyl, alkylamino, dialkylamino, alkenylamine, alkynylamino, acyl, alkenoyl, alkynoyl, acylamino, diacylamino, acyloxy, alkylsulfonyloxy, heterocycloxy, heterocycloamino, haloheterocycloalkyl, alkylsulfenyl, alkylcarbonyloxy, alkylthio, acylthio, phosphorus-containing groups such as phosphono and phosphinyl, aryl, heteroaryl, alkylaryl, aralkyl, alkylheteroaryl, cyano, cyanate, isocyanate, $CO_2H$, $CO_2$alkyl, $C(O)NH_2$, —C(O)NH(alkyl), and —C(O)N(alkyl)$_2$. Preferred substituents include halogen, $C_1$-$C_6$alkyl, $C_2$-$C_6$alkenyl, $C_1$-$C_6$haloalkyl, $C_1$-$C_6$alkoxy, hydroxy($C_{1-6}$) alkyl, $C_3$-$C_6$cycloalkyl, C(O)H, C(O)OH, NHC(O)H, NHC (O)$C_1$-$C_4$alkyl, C(O)$C_1$-$C_4$alkyl, $NH_2$, NHC$_1$-$C_4$alkyl, N($C_1$-$C_4$alkyl)$_2$, $NO_2$, OH and CN. Particularly preferred substituents include $C_{1-3}$alkyl, $C_{1-3}$alkoxy, halogen, OH, hydroxy($C_{1-3}$)alkyl (e.g., $CH_2OH$), C(O)$C_1$-$C_4$alkyl (eg C(O)$CH_3$), and $C_{1-3}$haloalkyl (e.g., $CF_3$, $CH_2CF_3$).

The present invention includes within its scope all stereoisomeric and isomeric forms of the compounds disclosed herein, including all diastereomeric isomers, racemates, enantiomers and mixtures thereof. Compounds of the present invention may have asymmetric centers and may occur, except when specifically noted, as mixtures of stereoisomers or as individual diastereomers, or enantiomers, with all isomeric forms being included in the present invention. It is also understood that the compounds described by Formula I may be present as E and Z isomers, also known as cis and trans isomers. Thus, the present disclosure should be understood to include, for example, E, Z, cis, trans, (R), (S), (L), (D), (+), and/or (−) forms of the compounds, as appropriate in each case. Where a structure has no specific stereoisomerism indicated, it should be understood that any and all possible isomers are encompassed. Compounds of the present invention embrace all conformational isomers. Compounds of the present invention may also exist in one or more tautomeric forms, including both single tautomers and mixtures of tautomers. Also included in the scope of the present invention are all polymorphs and crystal forms of the compounds disclosed herein.

The present invention includes within its scope isotopes of different atoms. Any atom not specifically designated as a particular isotope is meant to represent any stable isotope of that atom. Thus, the present disclosure should be understood to include deuterium and tritium isotopes of hydrogen All references cited in this application are specifically incorporated by cross-reference in their entirety. Reference to any such documents should not be construed as an admission that the document forms part of the common general knowledge or is prior art.

In the context of this specification the term "administering" and variations of that term including "administer" and "administration", includes contacting, applying, delivering or providing a compound or composition of the invention to an organism, or a surface by any appropriate means. In the context of this specification, the term "treatment", refers to any and all uses which remedy a disease state or symptoms, prevent the establishment of disease, or otherwise prevent, hinder, retard, or reverse the progression of disease or other undesirable symptoms in any way whatsoever.

In the context of this specification the term "effective amount" includes within its meaning a sufficient but non-toxic amount of a compound or composition of the invention to provide a desired effect. Thus, the term "therapeutically effective amount" includes within its meaning a sufficient but non-toxic amount of a compound or composition of the invention to provide the desired therapeutic effect. The exact amount required will vary from subject to subject depending on factors such as the species being treated, the sex, age and general condition of the subject, the severity of the condition being treated, the particular agent being administered, the mode of administration, and so forth. Thus, it is not possible to specify an exact "effective amount". However, for any given case, an appropriate "effective amount" may be determined by one of ordinary skill in the art using only routine experimentation.

BRIEF DESCRIPTION OF THE FIGURES

FIGS. 1A-1E show the ability of Compound 23 to inhibit SSAO/VAP-1 enzyme in various tissues in rats after a single oral dose, with activity determined 24 hours after administration: Abdominal Fat (FIG. 1A); Plasma (FIG. 1B); Lung (FIG. 1C); Aorta (FIG. 1D); Liver (FIG. 1E).

FIGS. 2A-2E show the ability of 2 mg/kg of Compound 23 to inhibit SSAO/VAP-1 enzyme in various tissues in rats after a single oral dose, with activity determined at various time points after administration: Abdominal Fat (FIG. 2A); Plasma (FIG. 2B); Lung (FIG. 2C); Aorta (FIG. 2D); Liver (FIG. 2E).

FIGS. 3A-3E show the ability of Compound 23 to inhibit SSAO/VAP-1 enzyme in various tissues in rats after 5 days of repeated, daily oral dosing, with activity determined 24 hours after administration of the final dose: Abdominal Fat (FIG. 3A); Plasma (FIG. 3B); Lung (FIG. 3C); Aorta (FIG. 3D); Liver (FIG. 3E).

FIGS. 5A & 5B show the ability of Compound 23 to reduce leukocyte migration in the mouse cremaster microcirculation: Inhibition of leukocyte rolling (FIG. 5A); Inhibition of leukocyte adhesion (FIG. 5B).

FIGS. 7A-7F show the ability of Compound 9 to reduce neutrophil migration and microglial activation in a mouse model of neurodegeneration: Neutrophils in substantia nigra (FIG. 7A); Neutrophils in dorso-lateral striatum (DLS) (FIG. 7B); Neutrophils in hippocampus (7C); Microglial cells in substantia nigra (FIG. 7D); Microglial cells in dorso-lateral striatum (DLS) (FIG. 7E); Microglial cells in hippocampus (FIG. 7F).

FIGS. 8A-8C show the ability of Compound 9 to reduce inflammation in a mouse model of acute lung inflammation: Neutrophils in broncheoalveolar lavage fluid (BALF) (FIG. 8A); IL-6 in broncheoalveolar lavage fluid (BALF) (FIG. 8B); TNF-α in broncheoalveolar lavage fluid (BALF) (FIG. 8C).

FIGS. 12A-12E show the ability of Compound 23 to improve liver function, reduce fibrosis and reduce inflammation in a rat model of liver fibrosis: Reduction in serum ALT (FIG. 12A); Reduction in liver AST (FIG. 12B); Reduction in Sirius red area (FIG. 12C); Reduction of inflammation score (FIG. 12D); Reduction of steatotic regions in the liver (FIG. 12E).

FIGS. 14A & 14B show the ability of Compound 23 to reduce inflammation in a mouse model of uveitis: Reduction of clinical score (FIG. 14A); Reduction of eosinophil infiltration (FIG. 14B).

DETAILED DESCRIPTION

Figure 4A:
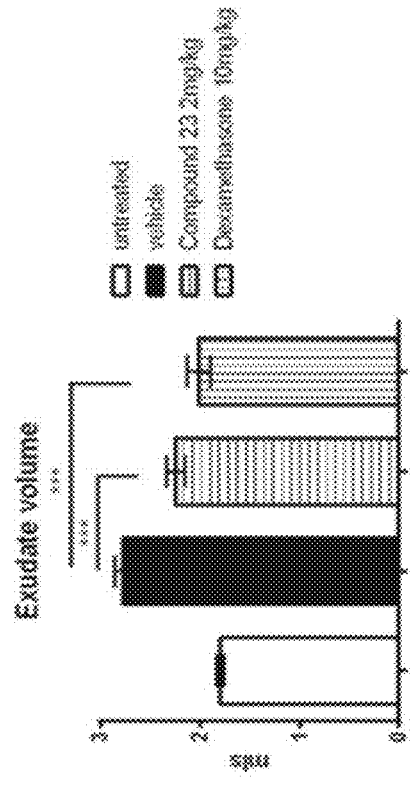
FIGS. 4A-4D show the ability of Compound 23 to reduce inflammation in an inflamed air pouch in a mouse model: Neutrophils in exudate (FIG. 4A); Exudate volume (FIG. 4B); IL-6 in exudate (FIG. 4C); TNF-α in exudate (FIG. 4D).
Figure 4B:
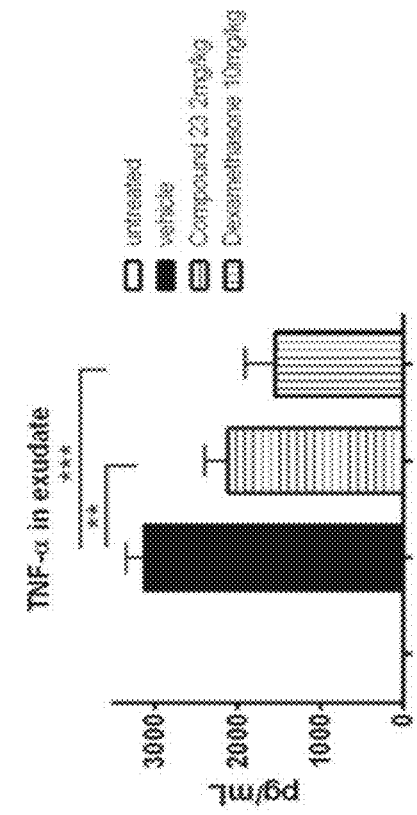
Figure 4C:
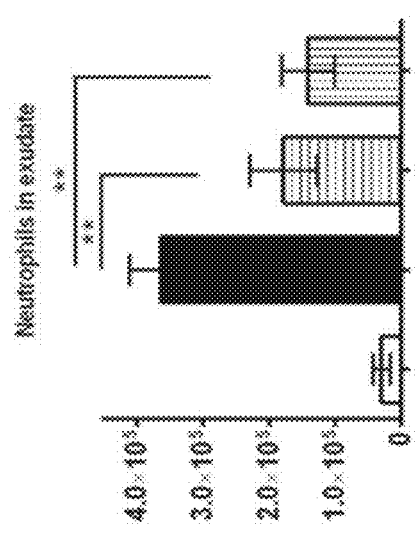
Figure 4D:
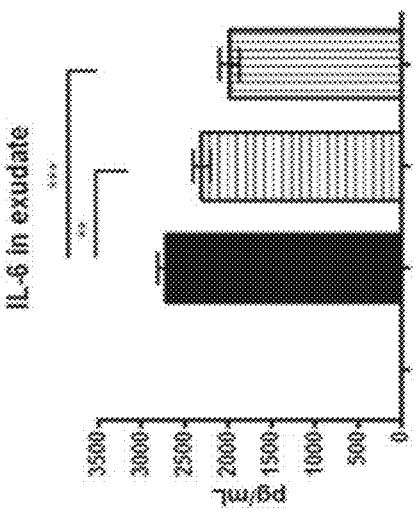

The present invention relates to substituted haloallylamine compounds that may inhibit SSAO/VAP-1.

In accordance with the present invention, there are provided compounds having the structure (Formula I):

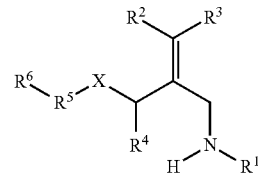

Formula I or a stereoisomer, pharmaceutically acceptable salt, polymorphic form, solvate or prodrug thereof; wherein:
$R^1$ and $R^4$ are independently hydrogen or optionally substituted $C_{1-6}$alkyl;
$R^2$ and $R^3$ are independently selected from the group consisting of hydrogen, chlorine and fluorine; provided, however, that $R^2$ and $R^3$ are not hydrogen at the same time;
$R^5$ is an optionally substituted arylene group;
$R^6$ is selected from

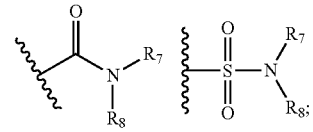

$R^7$ and $R^8$ are independently selected from the group consisting of hydrogen, optionally substituted $C_{1-6}$alkyl and optionally substituted $C_{3-7}$cycloalkyl; and
X is $CH_2$, oxygen, sulfur or $SO_2$.

In one embodiment of compounds of the present invention $R^1$ and $R^4$ are both hydrogen. In another embodiment of compounds of the present invention $R^1$ is hydrogen and $R^4$ is optionally substituted $C_{1-6}$alkyl. In a further embodiment of compounds of the present invention R is optionally substituted $C_{1-6}$alkyl and $R^4$ is hydrogen. In another embodiment of compounds of the present invention R is hydrogen and $R^4$ is methyl. In a further embodiment of compounds of the present invention $R^1$ is methyl and $R^4$ is hydrogen.

In one embodiment of compounds of the present invention $R^2$ and $R^3$ are independently selected from the group consisting of hydrogen, chlorine and fluorine, provided that $R^2$ and $R^3$ are not hydrogen at the same time. In another embodiment of compounds of the present invention $R^2$ and $R^3$ are independently hydrogen or fluorine, provided that $R^2$ and $R^3$ are not hydrogen at the same time. In a further embodiment of compounds of the present invention $R^2$ and $R^3$ are both fluorine. In another embodiment of compounds of the present invention $R^2$ is hydrogen and $R^3$ is fluorine. In a further embodiment of compounds of the present invention $R^2$ is fluorine and $R^3$ is hydrogen.

In one embodiment of compounds of the present invention $R^5$ is an optionally substituted arylene group. In another embodiment of compounds of the present invention $R^5$ is an unsubstituted arylene group. In a further embodiment of compounds of the present invention R⁵ is an optionally substituted phenylene group. In another embodiment of compounds of the present invention R⁵ is an unsubstituted phenylene group. In one embodiment of compounds of the present invention R⁵ is a phenylene group optionally substituted by one or more groups independently selected from alkyl, halo, alkoxy and haloalkyl. In another embodiment of compounds of the present invention R⁵ is a phenylene group optionally substituted by one or more groups independently selected from methyl, fluorine, chlorine, bromine, OCH₃ and CF₃.

In one embodiment of compounds of the present invention R⁶ is selected from:

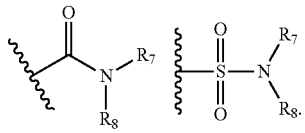

In another embodiment of compounds of the present invention R⁶ is

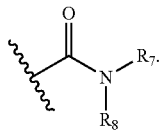

In a further embodiment of compounds of the present invention R⁶ is

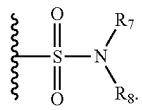

In one embodiment of compounds of the present invention R⁷ and R⁸ are independently selected from the group consisting of hydrogen, optionally substituted C₁₋₆alkyl and optionally substituted C₃₋₇cycloalkyl. In another embodiment of compounds of the present invention R⁷ and R⁸ are independently selected from the group consisting of hydrogen and optionally substituted C₁₋₆alkyl. In a further embodiment of compounds of the present invention R⁷ and R⁸ are both hydrogen. In another embodiment of compounds of the present invention R⁷ and R⁸ are both C₁₋₆alkyl. In a further embodiment of compounds of the present invention R⁷ is hydrogen and R⁸ is C₁₋₆alkyl. In a still further embodiment R⁷ and R⁸ are independently selected from the group consisting of hydrogen, tert-butyl, methyl, ethyl, isopropyl and 2-butyl.

In one embodiment of compounds of the present invention X is CH₂, oxygen, sulfur or SO₂. In another embodiment of compounds of the present invention X is CH₂, oxygen or sulfur. In further embodiment of compounds of the present invention X is oxygen.

In a particular embodiment of the present invention, there is provided a compound having the structure (Formula II), as follows:

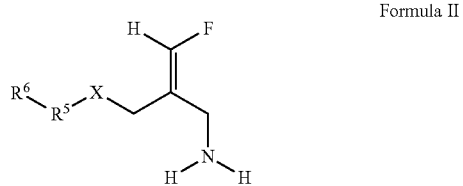

Formula II or a pharmaceutically acceptable salt, solvate, polymorphic form, or prodrug thereof;
wherein:
R⁵ is an optionally substituted arylene group;

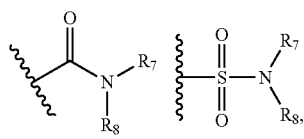

R⁶ is selected from
R⁷ and R⁸ are independently selected from the group consisting of hydrogen, optionally substituted C₁₋₆alkyl and optionally substituted C₃₋₇cycloalkyl; and
X is CH₂, oxygen, sulfur or SO₂.

In accordance with one embodiment of the present invention, presently preferred compounds include compounds of Formulae I and II wherein R³ is fluorine, and X is oxygen.

It is understood that compounds described by Formulae I or II may be administered in a prodrug form wherein the substituent R¹ can be selected from such functional groups as —C(O)alkyl, —C(O)aryl, —C(O)-arylalkyl, C(O)heteroaryl, —C(O)— heteroarylalkyl, or the like.

The compounds described by Formula I may exist as acid addition salts when a basic amino group is present, or as metal salts when an acidic group is present.

Exemplary compounds according to the present invention include the compounds set forth in Table 1:

TABLE 1

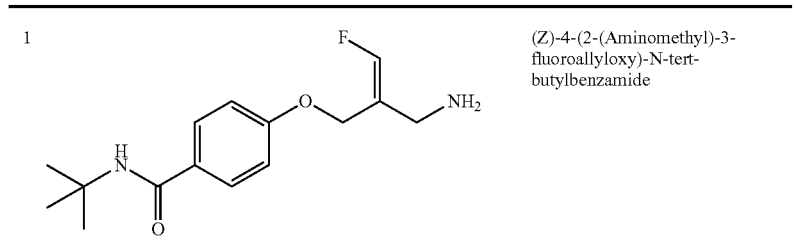

| 1 | | (Z)-4-(2-(Aminomethyl)-3-fluoroallyloxy)-N-tert-butylbenzamide |

TABLE 1-continued

| | | |
|---|---|---|
| 2 | | (Z)-4-(2-(Aminomethyl)-3-fluoroallyloxy)benzamide |
| 3 | | (E)-4-(2-(Aminomethyl)-3-fluoroallyloxy)benzamide |
| 4 | | (Z)-4-(2-(Aminomethyl)-3-fluoroallyloxy)-3-fluoro-N,N-dimethylbenzamide |
| 5 | | (E)-4-(3-(Aminomethyl)-4-fluorobut-3-en-2-yloxy)-N-tert-butylbenzamide |
| 6 | | (Z)-4-(2-(Aminomethyl)-3-fluoroallyloxy)-3-chloro-N,N-dimethylbenzamide |
| 7 | | 4-(2-(Aminomethyl)-3-fluoroallyloxy)-3-methoxy-N,N-dimethylbenzamide |
| 8 | | 4-(2-(Aminomethyl)-3-fluoroallylthio)-N,N-dimethylbenzamide |

TABLE 1-continued

| # | Structure | Name |
|---|---|---|
| 9 | 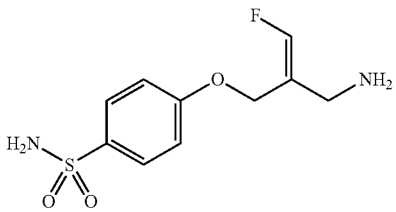 [SMILES: NC/C(=C/F)COc1ccc(S(N)(=O)=O)cc1] | (Z)-4-(2-(Aminomethyl)-3-fluoroallyloxy)benzenesulfonamide |
| 10 | 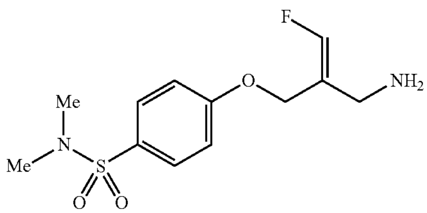 [SMILES: CN(C)S(=O)(=O)c1ccc(OC/C(=C\F)CN)cc1] | (Z)-4-(2-(Aminomethyl)-3-fluoroallyloxy)-N,N-dimethylbenzenesulfonamide |
| 11 | 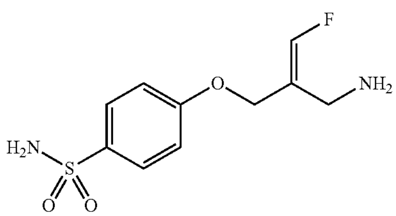 [SMILES: NC/C(=C\F)COc1ccc(S(N)(=O)=O)cc1] | (E)-4-(2-(Aminomethyl)-3-fluoroallyloxy)benzenesulfonamide |
| 12 | 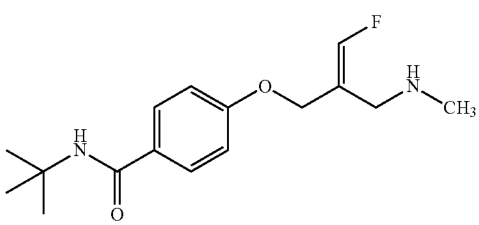 [SMILES: CNC/C(=C\F)COc1ccc(C(=O)NC(C)(C)C)cc1] | (E)-N-tert-Butyl-4-(3-fluoro-2-((methylamino)methyl)allyloxy)benzamide |
| 13 | 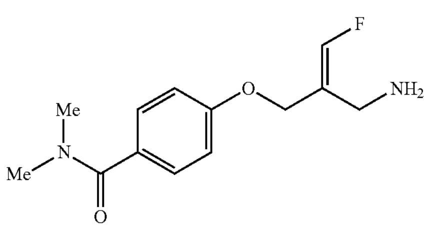 [SMILES: CN(C)C(=O)c1ccc(OC/C(=C/F)CN)cc1] | (E)-4-(2-(Aminomethyl)-3-fluoroallyloxy)-N,N-dimethylbenzamide |
| 14 | 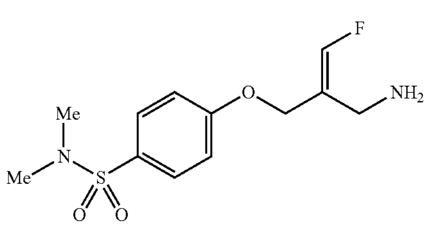 [SMILES: CN(C)S(=O)(=O)c1ccc(OC/C(=C/F)CN)cc1] | (E)-4-(2-(Aminomethyl)-3-fluoroallyloxy)-N,N-dimethylbenzenesulfonamide |
| 15 | 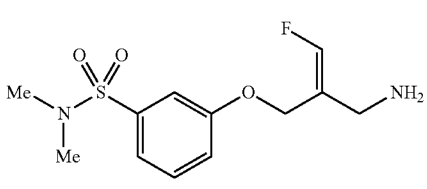 [SMILES: CN(C)S(=O)(=O)c1cccc(OC/C(=C\F)CN)c1] | (Z)-3-(2-(Aminomethyl)-3-fluoroallyloxy)-N,N-dimethylbenzenesulfonamide |

TABLE 1-continued

| | | |
|---|---|---|
| 16 | 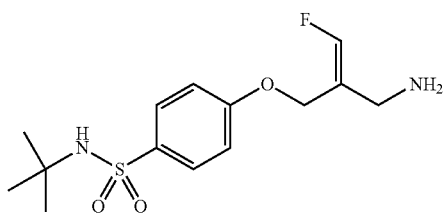 [SMILES: CC(C)(C)NS(=O)(=O)c1ccc(OC/C(=C\F)CN)cc1] | (Z)-4-(2-(Aminomethyl)-3-fluoroallyloxy)-N-tert-butylbenzenesulfonamide |
| 17 | 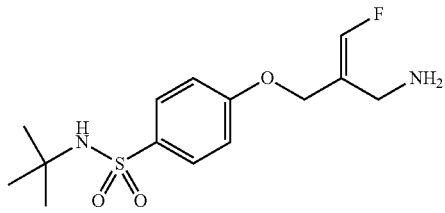 [SMILES: CC(C)(C)NS(=O)(=O)c1ccc(OC/C(=C/F)CN)cc1] | (E)-4-(2-(Aminomethyl)-3-fluoroallyloxy)-N-tert-butylbenzenesulfonamide |
| 18 | 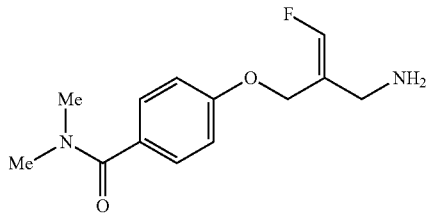 [SMILES: CN(C)C(=O)c1ccc(OC/C(=C\F)CN)cc1] | (Z)-4-(2-(Aminomethyl)-3-fluoroallyloxy)-N,N-dimethylbenzamide |
| 19 | 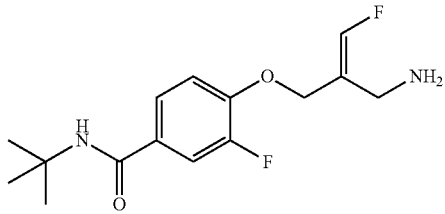 [SMILES: CC(C)(C)NC(=O)c1ccc(OC/C(=C/F)CN)c(F)c1] | (E)-4-(2-(Aminomethyl)-3-fluoroallyloxy)-N-tert-butyl-3-fluorobenzamide |
| 20 | 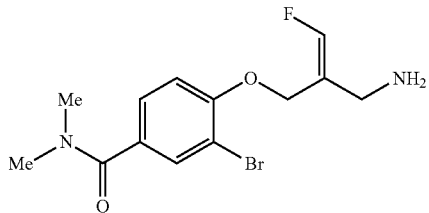 [SMILES: CN(C)C(=O)c1ccc(OC/C(=C\F)CN)c(Br)c1] | (Z)-4-(2-(Aminomethyl)-3-fluoroallyloxy)-3-bromo-N,N-dimethylbenzamide |
| 21 | 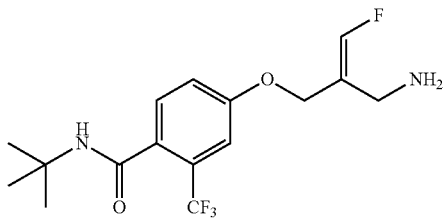 [SMILES: CC(C)(C)NC(=O)c1ccc(OC/C(=C/F)CN)cc1C(F)(F)F] | (E)-4-(2-(Aminomethyl)-3-fluoroallyloxy)-N-tert-butyl-2-(trifluoromethyl)benzamide |
| 22 | 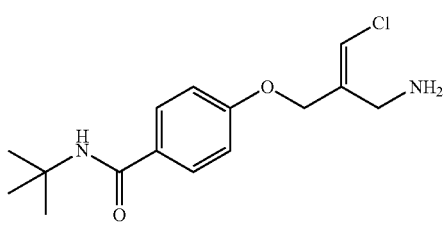 [SMILES: CC(C)(C)NC(=O)c1ccc(OC/C(=C/Cl)CN)cc1] | (E)-4-(2-(Aminomethyl)-3-chloroallyloxy)-N-tert-butylbenzamide |

TABLE 1-continued

| | | |
|---|---|---|
| 23 | 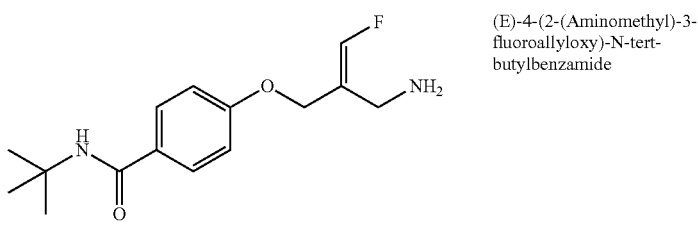 | (E)-4-(2-(Aminomethyl)-3-fluoroallyloxy)-N-tert-butylbenzamide |
| 24 | 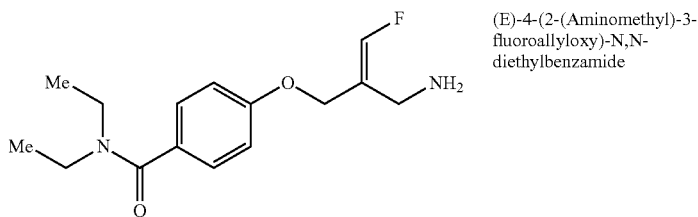 | (E)-4-(2-(Aminomethyl)-3-fluoroallyloxy)-N,N-diethylbenzamide |
| 25 | 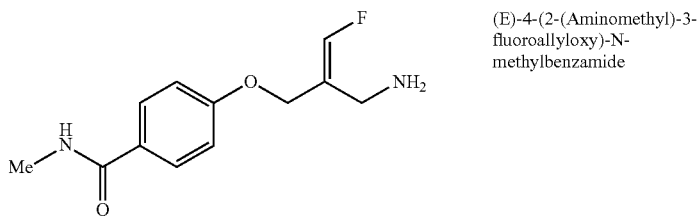 | (E)-4-(2-(Aminomethyl)-3-fluoroallyloxy)-N-methylbenzamide |
| 26 | 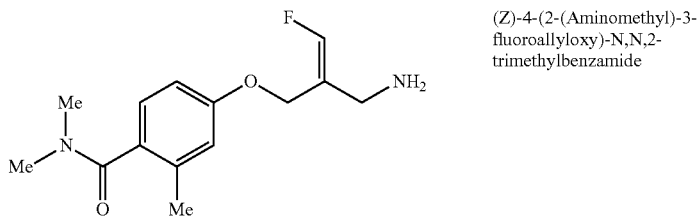 | (Z)-4-(2-(Aminomethyl)-3-fluoroallyloxy)-N,N,2-trimethylbenzamide |
| 27 | 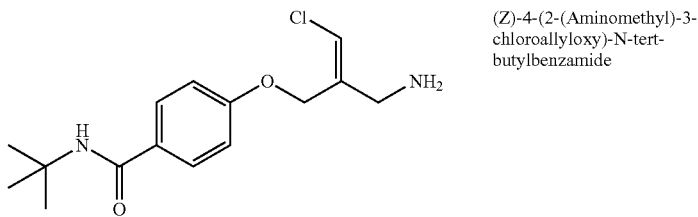 | (Z)-4-(2-(Aminomethyl)-3-chloroallyloxy)-N-tert-butylbenzamide |
| 28 | 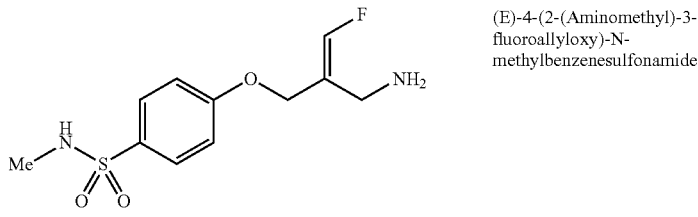 | (E)-4-(2-(Aminomethyl)-3-fluoroallyloxy)-N-methylbenzenesulfonamide |
| 29 | 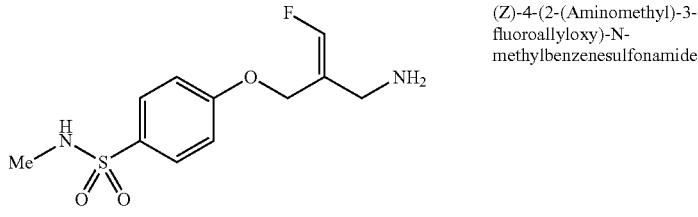 | (Z)-4-(2-(Aminomethyl)-3-fluoroallyloxy)-N-methylbenzenesulfonamide |

TABLE 1-continued

| 30 | 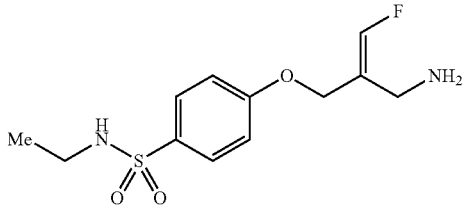 [SMILES: CCNS(=O)(=O)c1ccc(OC/C(=C/F)CN)cc1] | (E)-4-(2-(Aminomethyl)-3-fluoroallyloxy)-N-ethylbenzenesulfonamide |
| 31 | 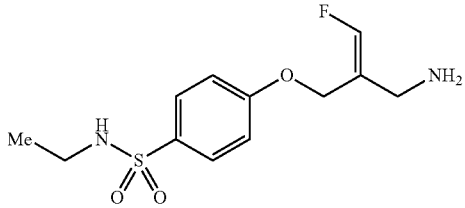 [SMILES: CCNS(=O)(=O)c1ccc(OC/C(=C\F)CN)cc1] | (Z)-4-(2-(Aminomethyl)-3-fluoroallyloxy)-N-ethylbenzenesulfonamide |
| 32 | 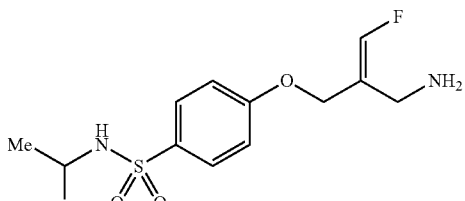 | (E)-4-(2-(Aminomethyl)-3-fluoroallyloxy)-N-isopropylbenzenesulfonamide |
| 33 | 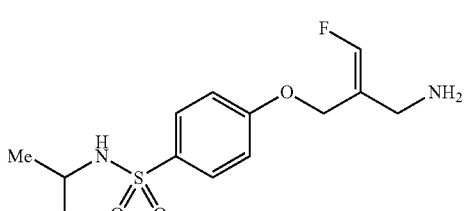 | (Z)-4-(2-(Aminomethyl)-3-fluoroallyloxy)-N-isopropylbenzenesulfonamide |
| 34 | 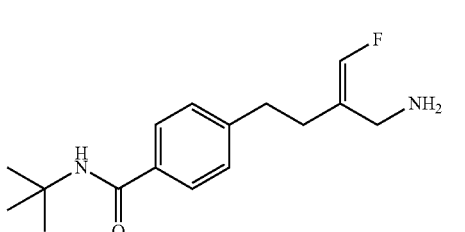 | (Z)-4-(3-(Aminomethyl)-4-fluorobut-3-enyl)-N-tert-butylbenzamide |
| 35 | 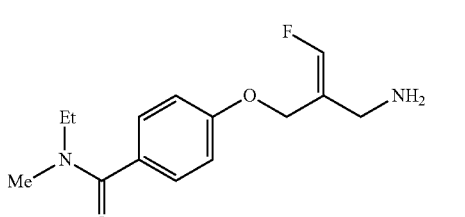 | (Z)-4-(2-(Aminomethyl)-3-fluoroallyloxy)-N-ethyl-N-methylbenzamide |
| 36 | 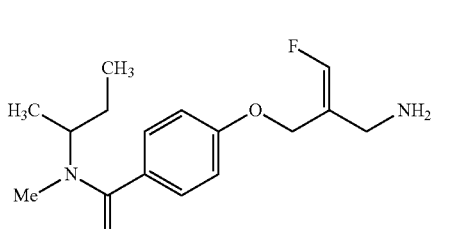 | (Z)-4-(2-(Aminomethyl)-3-fluoroallyloxy)-N-sec-butyl-N-methylbenzamide |

TABLE 1-continued

| | | |
|---|---|---|
| 37 | [structure] | (Z)-4-(2-(Aminomethyl)-3-fluoroallyloxy)-N-tert-butyl-N-methylbenzenesulfonamide |
| 38 | [structure] | (Z)-4-(2-(Aminomethyl)-3-fluoroallyloxy)-N-isopropyl-N-methylbenzenesulfonamide |
| 39 | [structure] | (E)-4-(2-(Aminomethyl)-3-fluoroallyloxy)-N-isopropylbenzamide | or a pharmaceutically acceptable salt or solvate thereof.

Preparation of Compounds of Formula I

The compounds of the invention can be prepared in a variety of ways, such as, for example, procedures described in U.S. Pat. Nos. 4,454,158; 4,699,928; and 4,650,907.

An alternate route to prepare compounds described by Formula I in which X=O or S employs the synthetic protocol described in Scheme 1, below. This is similar to procedures described in WO 2007/120528.

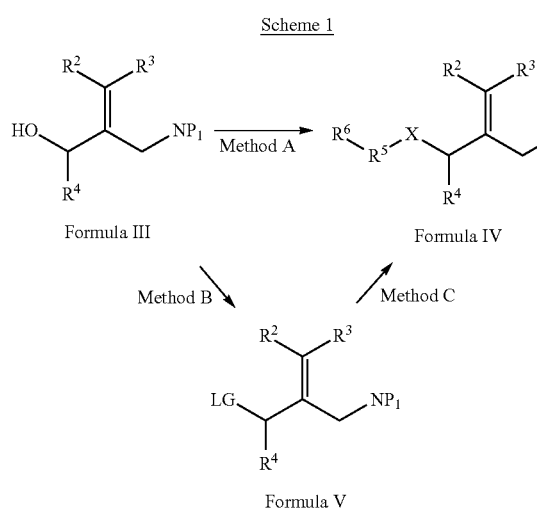

Scheme 1 wherein $R^2$, $R^3$, X and $R^5$ are as defined herein; $P_1$ is a functional group used to protect a nitrogen functionality; and LG is a leaving group. Examples of $P_1$ are carbonates such as the tert-butyloxycarbonyl (BOC), the 9-fluorenylmethyl-oxy-carbonyl (FMOC), and the benzyloxycarbonyl (CBZ) groups; examples of LG are bromo, chloro, iodo, triflates, tosylates, mesylates, and ester groups.

A compound represented by Formula III is either directly used in a displacement reaction (Method A), such as a Mitsunobu reaction, to yield the compound represented by Formula IV, or is first converted to a compound represented by Formula V which contains a leaving group (LG), such as bromide, chloride or iodide, by procedures well known in the art (Method B). Alternatively that alcohol can be directly activated with the tosyl protecting/activating group ($P_2$=Tosyl in Scheme 2, Formula VIII; see below). The activated compound described by Formula V is then treated with a nucleophilic reagent to furnish the compound represented by Formula IV (Method C).

The Mitsunobu reaction conditions are well described in the scientific and patent literature (available on the world wide web at en.wikipedia.org/wiki/Mitsunobu reaction, and Mitsunobu, O. The use of diethyl azodicarboxylate and triphenylphosphine in synthesis and transformation of natural products. *Synthesis* 1981, 1-28) and proceed by contacting an alcohol with an appropriately substituted phenolic or thiophenolic group, or a substituted phthalimide in the presence of a dialkyl azodicarboxylate and triphenylphosphine in an organic solvent such as tetrahydrofuran (THF) or CH2Cl2 ($CH_2Cl_2$).

Conversion of the alcohol group in Formula III to the corresponding bromide, chloride or iodide is accomplished by any number of commonly used procedures (See, for example, March J. *Advanced Organic Synthesis*, John Wiley & Sons, Third Edition 1985), including treatment with $PBr_3$ in toluene or $CBr_4$ and triphenylphosphine in an organic solvent such as $CH_2Cl_2$. The resulting halide can be treated with nucleophiles such as substituted alcohols, phenols, amines, or thiols to afford the compound represented by Formula IV.

There are many well established chemical procedures for the deprotection of the compounds described by Formula IV to the inventive compounds described by Formula I (Method J; see Scheme 2). For example if $P_1$ is a BOC protecting group, compounds described by Formula IV can be treated with an acidic substance such as dry hydrogen chloride in a solvent such as diethyl ether to furnish the compounds described by Formula I as the hydrochloride salt. In general, the free amino compounds are converted to acid addition salts for ease of handling and for improved chemical stability. Examples of acid addition salts include but are not limited to hydrochloride, hydrobromide and methanesulfonate salts.

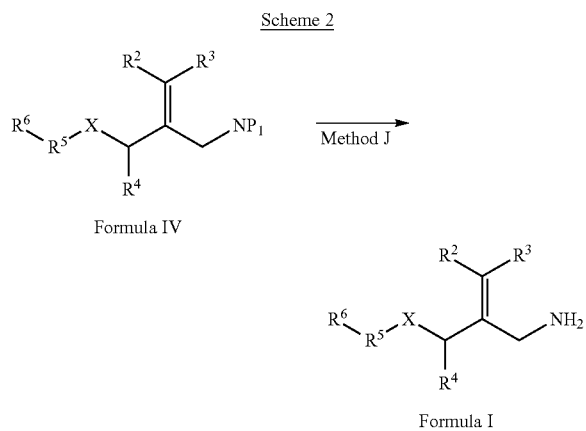

Scheme 2

Formula IV

Formula I

The preparation of compounds described by Formula III is straightforward from either commercially available or readily accessible aminodiol illustrated by Formula VI (See Scheme 3).

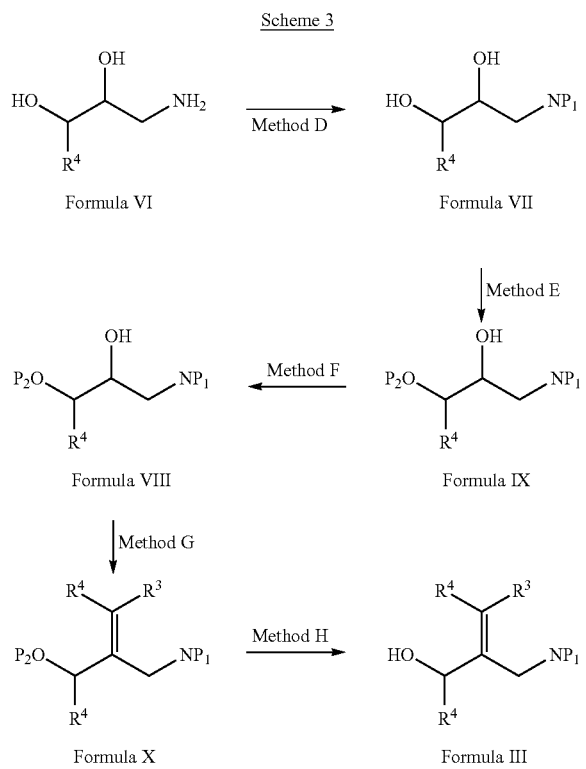

Scheme 3

Formula VI

Formula VII

Formula VIII

Formula IX

Formula X

Formula III

The first step is selective protection of the primary amine, preferably as the tert-butyl carbamate (BOC) ($P_1$=BOC in Formula VII), followed by selective protection of the primary alcohol to afford the alcohol described by Formula IX. Selective protection methods (Method E) are well known in the art of synthetic chemistry. For example, the primary alcohol can be selectively reacted with tert-butyl-(chloro)dimethylsilane in the presence of imizadole to furnish the tert-butyldimethylsilyl protected alcohol (Formula VII). Oxidation of the secondary alcohol is best achieved under Swern oxidation conditions (Method F) resulting in the ketone represented by Formula VIII. The haloalkene functional group in Formula X is introduced by Wittig or Homer-Wadsworth-Emmons reaction. When $R^2$ and $R^3$ are F and H in the structure described by Formula I, reaction of the ketone described by Formula VIII with fluoromethyl (triphenyl)phosphonium tetrafluoroborate in the presence of a strong base such as sodium bis(trimethylsilyl) amide affords the fluoroalkene as a mixture of E and Z isomers (described by Formula X). These isomers can be separated by chromatographic procedures to afford the individual E and Z isomers. Removal of the protecting group in the compounds described by Formula X can be readily achieved (Method H). The choice of the deprotecting reagent is determined by the nature of the protecting groups $P_1$ and $P_2$. When $P_2$ is tert-butyldimethylsilyl and $P_1$ is the BOC group, selective removal of $P_2$ is achieved with TBAF to yield the alcohol described by Formula III.

Therapeutic Uses and Formulations

The present invention provides methods for the use of compounds described by Formulae I and II to inhibit membrane-bound SSAO/VAP-1 and soluble SSAO/VAP-1. The relative inhibitory potencies of the compounds can be determined by the amount needed to inhibit the amine oxidase activity of SSAO/VAP-1 in a variety of ways, e.g., in an in vitro assay with recombinant human protein or with recombinant non-human enzyme, in cellular assays expressing normal rodent enzyme, in cellular assays which have been transfected with human protein, in in vivo tests in rodent and other mammalian species, and the like.

The present invention also discloses methods to use the compounds described by Formulae I and II to inhibit SSAO/VAP-1 in patients suffering from an inflammatory disease, and methods to treat inflammatory diseases. Human inflammatory diseases include arthritis, Crohn's disease, irritable bowel disease, psoriasis, asthma, chronic pulmonary obstructive disease, bronchiectasis, arthrosclerosis, inflammation due to diabetes, and inflammatory cell destruction following stroke.

Thus, in one aspect, the present invention is directed to methods of inhibiting an amine oxidase enzyme in a subject in need thereof, said methods comprising administering to said subject an effective amount of a compound of Formula I or Formula II to effect a positive therapeutic response.

In another aspect, the present invention is directed to methods of treating a disease associated with an amine oxidase enzyme, said methods comprising administering to a subject in need thereof a therapeutically effective amount of a compound of Formula I or Formula II.

In still another aspect, the present invention is directed to methods of treating a disease modulated by SSAO/VAP-1, said methods comprising administering to a subject in need thereof a therapeutically effective amount of a compound of Formula I or Formula II.

The above-described methods are applicable wherein the disease is inflammation. As employed herein, "inflammation" embraces a wide variety of indications, including arthritis (including juvenile rheumatoid arthritis), Crohn's disease, ulcerative colitis, inflammatory bowel diseases (e.g., irritable bowel disease), psoriasis, asthma, pulmonary inflammation, chronic pulmonary obstructive disease (COPD), bronchiectasis, skin inflammation, ocular disease, contact dermatitis, liver inflammation, liver autoimmune diseases, autoimmune hepatitis, primary biliary cirrhosis, sclerosing cholangitis, autoimmune cholangitis, alcoholic liver disease, artherosclerosis, chronic heart failure, congestive heart failure, ischemic diseases, stroke and complications thereof, myocardial infarction and complications thereof, inflammatory cell destruction following stroke, synovitis, systemic inflammatory sepsis, and the like.

The above-described methods are also applicable wherein the disease is Type I diabetes and complications thereof, Type II diabetes and complications thereof, and the like.

The above described methods are also applicable wherein the disease is macular degeneration or other ocular diseases.

The above described methods are also applicable wherein the disease is fibrosis. As employed here "fibrosis" includes such diseases as cystic fibrosis, idiopathic pulmonary fibrosis, liver fibrosis, including non-alcoholic fatty liver diseases such as non-alcoholic steatohepatitis (NASH) and alcohol induced fibrosis leading to cirrhosis of the liver, kidney fibrosis, scleroderma, radiation-induced fibrosis and other diseases where excessive fibrosis contributes to disease pathology.

The above-described methods are also applicable wherein the disease is a neuroinflammatory disease. As employed herein, "neuroinflammatory diseases" embrace a variety of indications, including stroke, Parkinson's disease, Alzheimer's disease, vascular dementia, multiple sclerosis, chronic multiple sclerosis, and the like.

The above-described methods are also applicable wherein the disease is cancer. In one embodiment the cancer is selected from the group consisting of lung cancer; breast cancer; colorectal cancer; anal cancer; pancreatic cancer; prostate cancer; ovarian carcinoma; liver and bile duct carcinoma; esophageal carcinoma; non-Hodgkin's lymphoma; bladder carcinoma; carcinoma of the uterus; glioma, glioblastoma, medullablastoma, and other tumors of the brain; kidney cancer; cancer of the head and neck; cancer of the stomach; multiple myeloma; testicular cancer; germ cell tumor; neuroendocrine tumor; cervical cancer; carcinoids of the gastrointestinal tract, breast, and other organs; signet ring cell carcinoma; mesenchymal tumors including sarcomas, fibrosarcomas, haemangioma, angiomatosis, haemangiopericytoma, pseudoangiomatous stromal hyperplasia, inyofibroblastoma, fibromatosis, inflammatory myofibroblastic tumour, lipoma, angiolipoma, granular cell tumour, neurofibroma, schwannoma, angiosarcoma, liposarcoma, rhabdomyosarcoma, osteosarcoma, leiomyoma or a leiomysarcoma.

Pharmaceutical and/or Therapeutic Formulations

In another embodiment of the present invention, there are provided compositions comprising a compound having Formula I or Formula II and at least one pharmaceutically acceptable excipient, carrier or diluent therefor. The compounds of Formula I may also be present as suitable salts, including pharmaceutically acceptable salts.

The phrase "pharmaceutically acceptable carrier" refers to any carrier known to those skilled in the art to be suitable for the particular mode of administration. In addition, the compounds may be formulated as the sole pharmaceutically active ingredient in the composition or may be combined with other active ingredients.

The phrase "pharmaceutically acceptable salt" refers to any salt preparation that is appropriate for use in a pharmaceutical application. By pharmaceutically acceptable salt it is meant those salts which, within the scope of sound medical judgement, are suitable for use in contact with the tissues of humans and lower animals without undue toxicity, irritation, allergic response and the like, and are commensurate with a reasonable benefit/risk ratio. Pharmaceutically acceptable salts are well known in the art and include acid addition and base salts. Hemisalts of acids and bases may also be formed. Pharmaceutically-acceptable salts include amine salts of mineral acids (e.g., hydrochlorides, hydrobromides, sulfates, and the like); and amine salts of organic acids (e.g., formates, acetates, lactates, malates, tartrates, citrates, ascorbates, succinates, maleates, butyrates, valerates, fumarates, and the like).

For compounds of formula (I) having a basic site, suitable pharmaceutically acceptable salts may be acid addition salts. For example, suitable pharmaceutically acceptable salts of such compounds may be prepared by mixing a pharmaceutically acceptable acid such as hydrochloric acid, sulfuric acid, methanesulfonic acid, succinic acid, fumaric acid, maleic acid, benzoic acid, phosphoric acid, acetic acid, oxalic acid, carbonic acid, tartaric acid, or citric acid with the compounds of the invention.

S. M. Berge et al. describe pharmaceutically acceptable salts in detail in *J. Pharmaceutical Sciences,* 1977, 66:1-19. The salts can be prepared in situ during the final isolation and purification of the compounds of the invention, or separately by reacting the free base function with a suitable organic acid. Representative acid addition salts include acetate, adipate, alginate, ascorbate, asparate, benzenesulfonate, benzoate, bisulfate, borate, butyrate, camphorate, camphorsulfonate, citrate, digluconate, cyclopentanepropionate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Suitable base salts are formed from bases that form non-toxic salts. Examples include the aluminium, arginine, benzathine, calcium, choline, diethylamine, diolamine, glycine, lysine, magnesium, meglumine, olamine, potassium, sodium, trometamine and zinc salts. Representative alkali or alkaline earth metal salts include sodium, lithium potassium, calcium, magnesium, and the like, as well as non-toxic ammonium, quaternary ammonium, and amine cations, including, but not limited to ammonium, tetramethylammonium, tetraethylammonium, methylamine, dimethylamine, trimethylamine, triethylamine, ethylamine, triethanolamine and the like.

Pharmaceutically acceptable salts of compounds of formula I may be prepared by methods known to those skilled in the art, including for example i. by reacting the compound of formula I with the desired acid or base;

ii. by removing an acid- or base-labile protecting group from a suitable precursor of the compound of formula I or by ring-opening a suitable cyclic precursor, for example, a lactone or lactam, using the desired acid or base; or iii. by converting one salt of the compound of formula I to another by reaction with an appropriate acid or base or by means of a suitable ion exchange column.

The above reactions (i)-(iii) are typically carried out in solution. The resulting salt may precipitate out and be collected by filtration or may be recovered by evaporation of the solvent. The degree of ionisation in the resulting salt may vary from completely ionised to almost non-ionised.

Thus, for instance, suitable pharmaceutically acceptable salts of compounds according to the present invention may be prepared by mixing a pharmaceutically acceptable acid such as hydrochloric acid, sulfuric acid, methanesulfonic acid, succinic acid, fumaric acid, maleic acid, benzoic acid, phosphoric acid, acetic acid, oxalic acid, carbonic acid, tartaric acid, or citric acid with the compounds of the invention. Suitable pharmaceutically acceptable salts of the compounds of the present invention therefore include acid addition salts.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when the solvent is water.

In one embodiment the compounds of Formula I may be administered in the form of a "prodrug". The phrase "prodrug" refers to a compound that, upon in vivo administration, is metabolized by one or more steps or processes or otherwise converted to the biologically, pharmaceutically or therapeutically active form of the compound. Prodrugs can be prepared by modifying functional groups present in the compound in such a way that the modifications are cleaved, either in routine manipulation or in vivo, to a compound described herein. For example, prodrugs include compounds of the present invention wherein a hydroxy, amino, or sulfhydryl group is bonded to any group that, when administered to a mammalian subject, can be cleaved to form a free hydroxyl, free amino, or free sulfhydryl group, respectively. Representative prodrugs include, for example, amides, esters, enol ethers, enol esters, acetates, formates, benzoate derivatives, and the like of alcohol and amine functional groups in the compounds of the present invention. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388-392).

Compositions herein comprise one or more compounds provided herein. The compounds are, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (see, e.g., Ansel *Introduction to Pharmaceutical Dosage Forms, Fourth Edition* 1985, 126).

In the compositions, effective concentrations of one or more compounds or pharmaceutically acceptable derivatives thereof is (are) mixed with a suitable pharmaceutical carrier. The compounds may be derivatized as the corresponding salts, esters, enol ethers or esters, acetals, ketals, orthoesters, hemiacetals, hemiketals, acids, bases, solvates, hydrates or prodrugs prior to formulation, as described above. The concentrations of the compounds in the compositions are effective for delivery of an amount, upon administration, that treats, prevents, or ameliorates one or more of the symptoms of diseases or disorders to be treated.

In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and in PCT publication WO 04/018997, and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art.

In one embodiment, a therapeutically effective dosage should produce a serum concentration of active ingredient of from about 0.1 ng/mL to about 50-100 µg/mL. The pharmaceutical compositions, in another embodiment, should provide a dosage of from about 0.001 mg to about 2000 mg of compound per kilogram of body weight per day. Pharmaceutical dosage unit forms are prepared to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

Dosing may occur at intervals of minutes, hours, days, weeks, months or years or continuously over any one of these periods. Suitable dosages lie within the range of about 0.1 ng per kg of body weight to 1 g per kg of body weight per dosage. The dosage is preferably in the range of 1 µg to 1 g per kg of body weight per dosage, such as is in the range of 1 mg to 1 g per kg of body weight per dosage. Suitably, the dosage is in the range of 1 µg to 500 µg per kg of body weight per dosage, such as 1 µg to 200 mg per kg of body weight per dosage, or 1 µg to 100 mg per kg of body weight per dosage. Other suitable dosages may be in the range of 1 mg to 250 mg per kg of body weight, including 1 mg to 10, 20, 50 or 100 mg per kg of body weight per dosage or 10 µg to 100 mg per kg of body weight per dosage.

Suitable dosage amounts and dosing regimens can be determined by the attending physician and may depend on the particular condition being treated, the severity of the condition, as well as the general health, age and weight of the subject.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In instances in which the compounds exhibit insufficient solubility, methods for solubilizing compounds may be used. Such methods are known to those of skill in this art, and include, but are not limited to, using co-solvents, such as dimethylsulfoxide (DMSO), using surfactants, such as TWEEN®, dissolution in aqueous sodium bicarbonate, formulating the compounds of interest as nanoparticles, and the like. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Actual methods of preparing such dosage forms are known, or will be apparent, to those skilled in this art; for example, see Remington's Pharmaceutical Sciences, Mack Publishing Company, Easton, Pa., 15th Edition, 1975.

Dosage forms or compositions containing active ingredient in the range of 0.005% to 100% (wt %) with the balance made up from non-toxic carrier may be prepared. Methods for preparation of these compositions are known to those skilled in the art. The contemplated compositions may contain 0.001%-100% (wt %) active ingredient, in one embodiment 0.1-95% (wt %), in another embodiment 75-85% (wt %).

Modes of Administration

Convenient modes of administration include injection (subcutaneous, intravenous, etc.), oral administration, inhalation, transdermal application, topical creams or gels or powders, vaginal or rectal administration. Depending on the route of administration, the formulation and/or compound may be coated with a material to protect the compound from the action of enzymes, acids and other natural conditions which may inactivate the therapeutic activity of the compound. The compound may also be administered parenterally or intraperitoneally.

Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

Solid Compositions for Oral Administration

In certain embodiments, the formulations are solid dosage forms, in one embodiment, capsules or tablets. The tablets, pills, capsules, troches and the like can contain one or more of the following ingredients, or compounds of a similar nature: a binder; a lubricant; a diluent; a glidant; a disintegrating agent; a colouring agent; a sweetening agent; a flavouring agent; a wetting agent; an emetic coating; and a film coating. Examples of binders include microcrystalline cellulose, gum tragacanth, glucose solution, acacia mucilage, gelatin solution, molasses, polvinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavours. Flavouring agents include natural flavours extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

The compound, or pharmaceutically acceptable derivative thereof, could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colourings and flavours.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Liquid Compositions for Oral Administration

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Colouring and flavouring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Colouring agents include any of the approved certified water soluble FU and C dyes, and mixtures thereof. Flavouring agents include natural flavours extracted from plants such fruits, and synthetic blends of compounds which produce a pleasant taste sensation.

For a solid dosage form, the solution or suspension, in for example propylene carbonate, vegetable oils or triglycerides, is in one embodiment encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

Injectables, Solutions and Emulsions

Parenteral administration, in one embodiment characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions including EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intra-arterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos.

4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in one embodiment, have diameters of less than 50 microns, in one embodiment less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% (vol %) isotonic solutions, pH about 5-7, with appropriate salts.

Compositions for Other Routes of Administration

Other routes of administration, such as transdermal patches, including iontophoretic and electrophoretic devices, and rectal administration, are also contemplated herein.

Transdermal patches, including iontophoretic and electrophoretic devices, are well known to those of skill in the art. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm.

Tablets and capsules for rectal administration are manufactured using the same pharmaceutically acceptable substance and by the same methods as for formulations for oral administration.

Targeted Formulations

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

Co-Administration with Other Drugs

In accordance with another aspect of the present invention, it is contemplated that compounds as described herein may be administered to a subject in need thereof in combination with medication considered by those of skill in the art to be current standard of care for the condition of interest. Such combinations provide one or more advantages to the subject, e.g., requiring reduced dosages to achieve similar benefit, obtaining the desired palliative affect in less time, and the like.

Compounds in accordance with the present invention may be administered as part of a therapeutic regimen with other drugs. It may be desirable to administer a combination of active compounds, for example, for the purpose of treating a particular disease or condition. Accordingly, it is within the scope of the present invention that two or more pharmaceutical compositions, at least one of which contains a compound of Formula (I) according to the present invention, may be combined in the form of a kit suitable for co-administration of the compositions.

In one embodiment of the methods of the present inventions a compound of Formula I may be administered with a second therapeutic agent. In one embodiment the second therapeutic agent is selected from the group consisting of an anti-cancer agent, an anti-inflammatory agent, an anti-hypertensive agent, an anti-fibrotic agent, an anti-angiogenic agent, an anti-diabetic agent, and an immunosuppressive agent.

When two or more active ingredients are co-administered, the active ingredients may be administered simultaneously, sequentially or separately. In one embodiment the compound of Formula I is co-administered simultaneously with a second therapeutic agent. In another embodiment the compound of Formula I and the second therapeutic agent are administered sequentially. In a further embodiment the compound of Formula I and the second therapeutic agent are administered separately.

The invention will now be described in greater detail with reference to the following non-limiting examples. The examples are intended to serve to illustrate the invention and should not be construed as limiting the generality of the disclosure of the description throughout this specification.

EXAMPLE 1

Preparation of the synthons (Z)-tert-butyl 2-(bromomethyl)-3-fluoroallylcarbamate and (E)-tert-butyl 2-(bromomethyl)-3-fluoroallylcarbamate

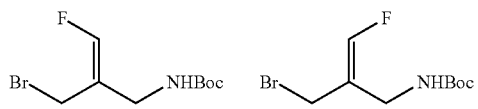 [SMILES: CC(C)(C)OC(=O)NC/C(=C/F)CBr ; CC(C)(C)OC(=O)NC/C(=C\F)CBr]

Preparation of tert-butyl 3-(tert-butyldimethylsilyloxy)-2-hydroxypropylcarbamate

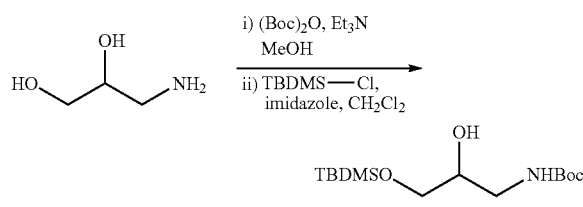

To a stirred solution of 3-amino-1,2-propanediol (10.0 g, 0.11 mol) and triethylamine (23 mL, 0.17 mol) in MeOH (200 mL) at room temperature was added di-tert-butyl dicarbonate (26.4 g, 0.12 mol). The resulting solution was left to stir at room temperature overnight. The reaction mixture was concentrated under reduced pressure then co-evaporated with toluene to remove all the MeOH. The crude residue was taken up in $CH_2Cl_2$ and, after cooling to 0° C., imidazole and tert-butyl-(chloro)dimethylsilane were sequentially added. The resulting mixture was left to stir at this temperature for 2 h. The reaction mixture was partitioned between water (100 mL) and $CH_2Cl_2$ (70 mL) and the aqueous layer was extracted with further $CH_2Cl_2$ (2×70 mL). The combined organics were dried over $Na_2SO_4$ and concentrated in vacuo. The crude residue was purified over silica gel eluting with n-hexane followed by 10% ethyl acetate in hexanes to afford tert-butyl 3-(tert-butyldimethylsilyloxy)-2-hydroxypropylcarbamate (32.6 g, 97.3%) as a colourless oil. $^1$H-NMR (300 MHz, $CDCl_3$) δppm: 0.09 (6 H, s), 0.91 (9 H, s), 1.46 (9 H, s), 2.86 (1 H, br d, J 4.2 Hz), 3.13 (1 H, ddd, J 14.1, 6.7, 5.3 Hz), 3.30-3.43 (1 H, m), 3.54 (1 H, dd, J 10.1, 6.2 Hz), 3.66 (1 H, dd, J 10.1, 4.5 Hz), 3.70-3.80 (1 H, m), 4.98 (1 H, br s).

Preparation of tert-butyl 3-(tert-butyldimethylsilyloxy)-2-oxopropylcarbamate

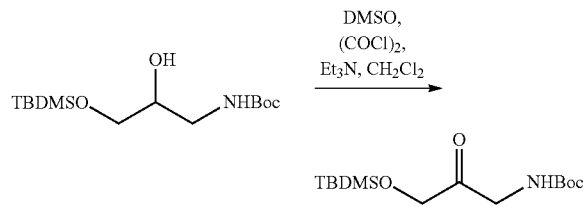

To a stirring solution of oxalyl chloride (13.6 mL, 0.16 mol) in dry $CH_2Cl_2$ (150 mL) at −78° C. under $N_2$ was added DMSO (15.2 mL, 0.21 mol) dropwise over 30 min After complete addition the resulting solution was stirred at −78° C. for 1 h. A solution of tert-butyl 3-(tert-butyldimethylsilyloxy)-2-hydroxypropylcarbamate (32.6 g, 0.11 mol) in $CH_2Cl_2$ (50 mL) was then added dropwise over 20 min Stirring was continued for a further 1 hour at which time triethylamine (59.6 mL, 0.43 mol) was added. The cooling bath was removed and the reaction mixture was allowed to warm to room temperature. The reaction mixture was partitioned between water (100 mL) and $CH_2Cl_2$ (70 mL) and the aqueous layer was extracted with further $CH_2Cl_2$ (2×70 mL); the combined organics were dried over $Na_2SO_4$ and concentrated under a stream of nitrogen gas. The crude residue was purified over silica gel eluting with 5% ethylacetate in n-hexane to give tert-butyl 3-(tert-butyldimethylsilyloxy)-2-oxopropylcarbamate (29.8 g, 92%) as a pale yellow oil. $^1$H-NMR (300 MHz; $CDCl_3$) δppm: 0.11 (6 H, s), 0.94 (9 H, s), 1.47 (9 H, s), 3.92 (2 H, s), 4.26 (2 H, d, J 4.6 Hz), 5.22 (1 H, br s).

Preparation of tert-butyl 2-((tert-butyldimethylsilyloxy)methyl)-3-fluoroallylcarbamate

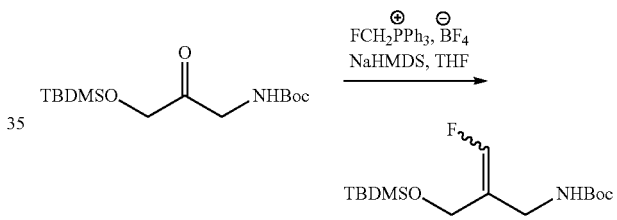

To a vigorously stirring suspension of fluoromethyl(triphenyl)-phosphonium tetrafluoroborate (18.9 g, 49.4 mmol) in dry THF (190 mL) at −20° C. under $N_2$ was added sodium bis(trimethylsilyl)amide (1.0 M in THF; 49.4 mL, 49.4 mmol) slowly over 10 min. The resulting deep orange solution was left to stir at this temperature for 15 min A solution of tert-butyl 3-(tert-butyldimethylsilyloxy)-2-oxopropylcarbamate (10.0 g, 33.0 mmol) in THF (10 mL) was then added slowly over 10 min After complete addition, stirring was continued for a further 1 h during which time the reaction was allowed to warm slowly to room temperature. The reaction was quenched by addition of water (5 mL) and the reaction mixture was concentrated in vacuo. The residue was partitioned between water (100 mL) and diethyl ether (100 mL) and the aqueous layer was extracted with further diethyl ether (2×100 ml). The combined organics were dried over $Na_2SO_4$ and concentrated under reduced pressure. The crude residue was purified over silica gel eluting with n-hexane followed by 6% ethylacetate in n-hexane to give tert-butyl 2-((tert-butyldimethylsilyloxy)methyl)-3-fluoroallylcarbamate as a mixture of E/Z double-bond isomers (E/Z=1:1; 9.9 g, 94%). The isomers were not separated at this stage.

Preparation of (E)-tert-butyl 3-fluoro-2-(hydroxymethyl)allylcarbamate and (Z)-tert-butyl 3-fluoro-2-(hydroxymethyl)allylcarbamate

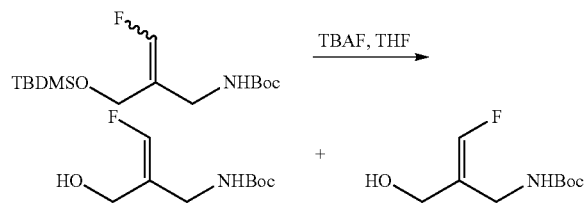

To a stirring solution of tert-butyl 2-((tert-butyldimethylsilyloxy)methyl)-3-fluoroallylcarbamate (E/Z=1:1; 12.0 g, 37.6 mmol) in THF (30 mL) at room temperature was added TBAF (1.0 M in THF; 45.1 mL, 45.1 mmol). The resulting solution was left to stir for 30 min. The reaction mixture was partitioned between water (70 mL) and ethyl acetate (50 mL). The aqueous layer was extracted with ethyl acetate (50 mL) and the combined organics were washed with saturated aqueous NH₄Cl (70 mL) followed by brine (70 mL). After drying over Na₂SO₄, the organics were concentrated in vacuo. Purification of the crude material over silica gel eluting with 20% ethyl acetate and 5% THF in n-hexane gave (Z)-tert-butyl 3-fluoro-2-(hydroxymethyl)-allylcarbamate (0.5 g, 6.5%), (E)-tert-butyl 3-fluoro-2-(hydroxymethyl)allylcarbamate (1.2 g, 15.6%) and a mixture of the E/Z isomers (5.5 g, 71.4%).

(Z)-tert-Butyl 3-fluoro-2-(hydroxymethyl)allylcarbamate: ¹H-NMR (300 MHz; CDCl₃) δppm: 1.46 (9 H, s), 3.41 (1 H, br s), 3.74 (2 H, dd, J 6.5, 3.1 Hz), 4.28 (2 H, dd, J 6.0, 2.3 Hz), 4.87 (1 H, br s), 6.53 (1H, dd, J 83.5 Hz).

(E)-tert-Butyl 3-fluoro-2-(hydroxymethyl)allylcarbamate: ¹H-NMR (300 MHz; CDCl₃) δppm: 1.47 (9 H, s), 3.78 (1 H, t, J 6.4 Hz), 3.93-4.02 (4 H, m), 4.94 (1 H, br s), 6.63 (1 H, d, J 83.6 Hz).

Preparation of (Z)-tert-butyl 2-(bromomethyl)-3-fluoroallylcarbamate

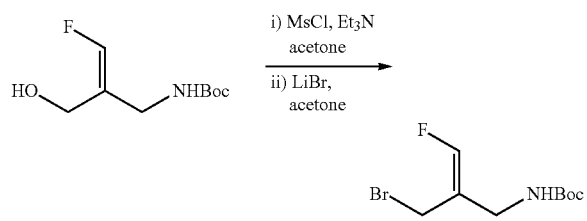

To a stirring solution of (Z)-tert-butyl 3-fluoro-2-(hydroxymethyl)-allylcarbamate (0.50 g, 2.44 mmol) in acetone (15 mL) at 0° C. under N₂ was added sequentially triethylamine (0.51 mL, 3.65 mmol) and methanesulfonyl chloride (0.23 mL, 2.92 mmol). The resulting mixture was stirred at this temperature for 30 min. The reaction mixture was filtered to remove the precipitated salts and the filter cake was washed with further acetone (10 mL). The filtrate was charged with lithium bromide (1.06 g, 12.18 mmol) and the resulting suspension was stirred at room temperature for 1 h. The reaction mixture was partitioned between water (25 mL) and ethyl acetate (25 mL) and the aqueous layer was extracted with further ethyl acetate (25 mL). The combined organics were washed with brine (25 mL), dried over Na₂SO₄ and concentrated in vacuo to give (Z)-tert-butyl 2-(bromomethyl)-3-fluoroallylcarbamate as a pale yellow oil (0.63 g, 96%). ¹H-NMR (300 MHz; CDCl₃) δppm: 1.47 (9 H, s), 3.80 (2 H, br s), 4.09 (2 H, d, J 2.6 Hz), 4.75 (1 H, br s), 6.65 (1 H, d, J 81.9 Hz).

Preparation of (E)-tert-butyl 2-(bromomethyl)-3-fluoroallylcarbamate

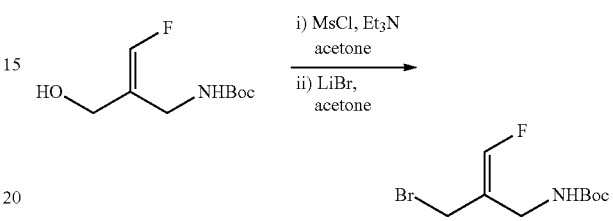

To a stirring solution of (E)-tert-butyl 3-fluoro-2-(hydroxymethyl)-allylcarbamate (1.20 g, 5.85 mmol) in acetone (20 mL) at 0° C. under N₂ was added sequentially triethylamine (1.22 mL, 8.77 mmol) and methanesulfonyl chloride (0.54 mL, 7.02 mmol). The resulting mixture was stirred at this temperature for 30 min. The reaction mixture was filtered to remove the precipitated salts and the filter cake was washed with further acetone (10 mL). The filtrate was charged with lithium bromide (2.54 g, 29.24 mmol) and the resulting suspension was stirred at room temperature for 1 h. The reaction mixture was partitioned between water (25 mL) and ethyl acetate (25 mL) and the aqueous layer was extracted with further ethyl acetate (25 mL). The combined organics were washed with brine (25 mL), dried over Na₂SO₄ and concentrated in vacuo to give (E)-tert-butyl 2-(bromomethyl)-3-fluoroallylcarbamate as a pale yellow oil (1.46 g, 93%). ¹H-NMR (300 MHz; CDCl₃) δppm: 1.47 (9 H, s), 3.97 (2 H, dd, J 3.5, 0.7 Hz), 4.02 (2 H, br d, J 6.1 Hz), 4.78 (1 H, br s), 6.79 (1 H, d, J 81.1 Hz).

EXAMPLE 2

Procedure A: Preparation of (Z)-tert-butyl 2-((4-(dimethylcarbamoyl)phenoxy)-methyl)-3-fluoroallylcarbamate

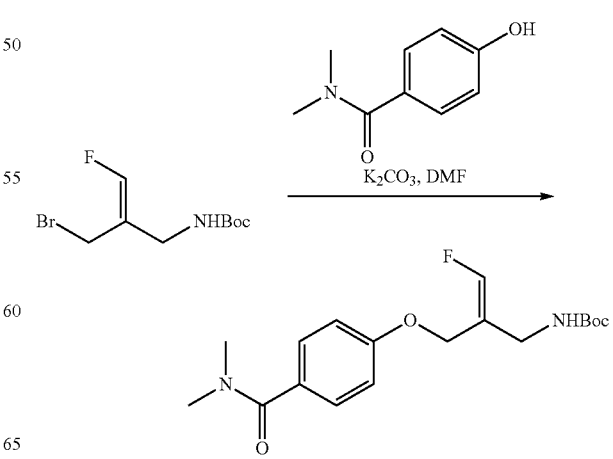

To a vigorously stirring suspension of (Z)-tert-butyl 2-(bromomethyl)-3-fluoroallylcarbamate (430.0 mg, 1.60 mmol) and potassium carbonate (332.5 mg, 2.41 mmol) in dry DMF (2.0 mL) at room temperature under $N_2$ was added 4-hydroxy-N,N-dimethylbenzamide (291.4 mg, 1.76 mmol). The resulting mixture was stirred at room temperature overnight. The reaction mixture was partitioned between water (40 mL) and ethyl acetate (20 mL) and the aqueous layer was extracted with further ethyl acetate (2×20 ml). The combined organics were washed with saturated aqueous $NH_4Cl$ (40 mL), brine (40 mL), dried over $Na_2SO_4$ and concentrated under reduced pressure. Purification of the crude material over silica gel eluting with 60% ethyl acetate in n-hexane followed by 75% ethyl acetate in n-hexane gave (Z)-tert-butyl 2-((4-(dimethylcarbamoyl)phenoxy)methyl)-3-fluoroallylcarbamate (520.0 mg, 92%) as a colourless oil. $^1$H-NMR (300 MHz; $CDCl_3$) δppm: 1.44 (9 H, s), 3.07 (6 H, br s), 3.78 (2 H, br s), 4.74 (2 H, dd, J 2.7, 0.8 Hz), 4.80 (1 H, br s), 6.75 (1 H, d, J 82.7 Hz), 6.95 (2 H, d, J 8.9 Hz), 7.42 (2 H, d, J 8.8 Hz).

Procedure B: Preparation of (Z)-4-(2-(aminomethyl)-3-fluoroallyloxy)-N,N-dimethyl-benzamide hydrochloride (Compound 18)

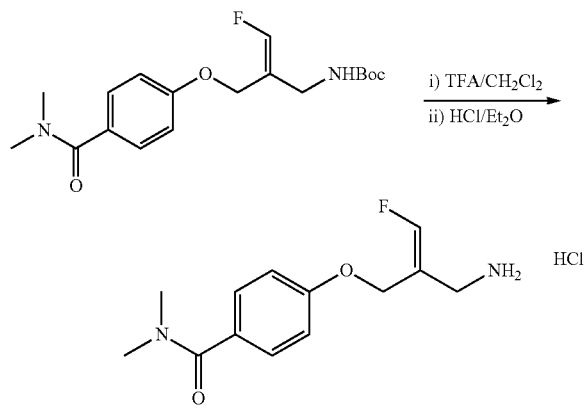

To a stirring solution of (Z)-tert-butyl 2-((4-(dimethylcarbamoyl)-phenoxy)methyl)-3-fluoroallylcarbamate (520.0 mg, 1.48 mmol) in $CH_2Cl_2$ (8.0 mL) at room temperature was added trifluoroacetic acid (2.0 mL). The resulting mixture was stirred at room temperature for 30 min. All volatiles were removed in vacuo and the residue was co-evaporated with $CH_2Cl_2$ (2×20 mL) to remove trifluoroacetic acid. The resulting oil was taken up in ethyl acetate (3.0 mL) and then ethereal HCl (2.0 M in diethyl ether; 1.0 mL, 2.0 mmol) was added. The precipitate formed was isolated and dried under reduced pressure to afford (Z)-4-(2-(aminomethyl)-3-fluoroallyloxy)-N,N-dimethylbenzamide hydrochloride (301 mg, 71%) as a pale yellow solid; m.p.=135-137° C.; $^1$H-NMR (300 MHz; MeOD) δppm: 3.06 (3 H, br s), 3.10 (3 H, br s), 3.71 (2 H, d, J 3.0 Hz), 4.88 (2 H, dd, J 2.8, 0.8 Hz), 7.11 (2H, d, J 8.9 Hz), 7.13 (1 H, d, J 80.8 Hz), 7.45 (2 H, d, J 8.9 Hz).

Procedure C: Preparation of (Z)-tert-butyl 2-((4-(N,N-dimethylsulfamoyl)phenoxy)methyl)-3-fluoroallylcarbamate

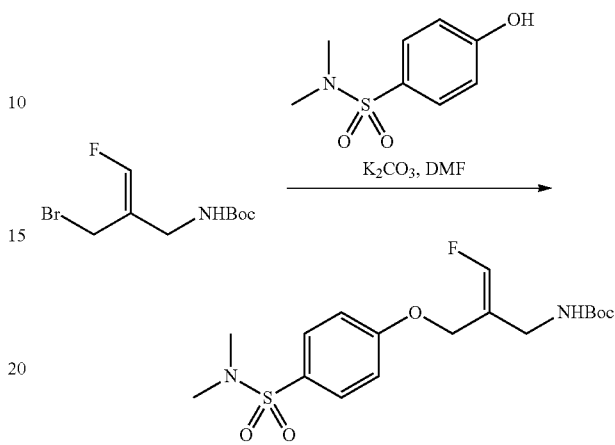

To a vigorously stirring suspension of (Z)-tert-butyl 2-(bromomethyl)-3-fluoroallylcarbamate (232.0 mg, 0.87 mmol) in dry DMF (2.0 mL) at room temperature under $N_2$ was sequentially added potassium carbonate (300.0 mg, 2.16 mmol) and 4-hydroxy-N,N-dimethylbenzamide (174.0 mg, 0.87 mmol). The resulting suspension was left to stir at room temperature for 2 h. The reaction mixture was partitioned between saturated aqueous $NH_4Cl$ (40 mL) and ethyl acetate (20 mL) and the aqueous layer was extracted with further ethyl acetate (20 ml). The combined organics dried over $Na_2SO_4$ and concentrated under reduced pressure. Purification of the crude material over silica gel eluting with 50% ethyl acetate in n-hexane gave (Z)-tert-butyl 2-((4-(N,N-dimethylsulfamoyl)phenoxy)methyl)-3-fluoroallylcarbamate (279.0 mg, 83%) as a colourless oil. $^1$H-NMR (300 MHz; $CDCl_3$) δppm: 1.42 (9 H, s), 2.69 (6 H, s), 3.79 (2 H, br s), 4.76 (2 H, d, J 2.7 Hz), 4.81 (1 H, br s), 6.76 (1 H, d, J 82.6 Hz), 7.04 (2 H, d, J 8.9 Hz), 7.72 (2 H, d, J 9.0 Hz).

Procedure D: Preparation of (Z)-4-(2-(aminomethyl)-3-fluoroallyloxy)-N,N-dimethyl-benzenesulfonamide hydrochloride (Compound 10)

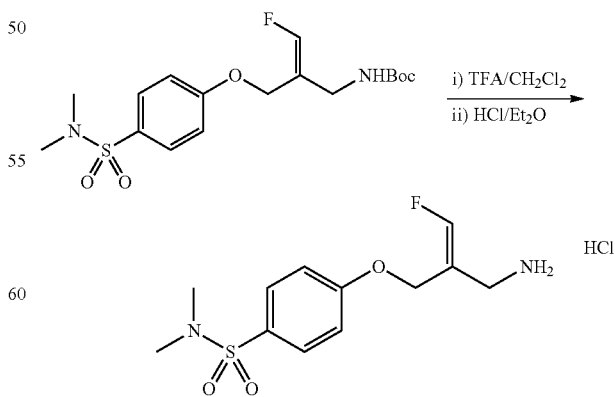

To a stirring solution of (Z)-tert-butyl 2-((4-(N,N-dimethylsulfamoyl)phenoxy)methyl)-3-fluoroallylcarbamate (279.0 mg, 0.72 mmol) in CH$_2$Cl$_2$ (4.0 mL) at room temperature was added trifluoroacetic acid (1.0 mL). The resulting mixture was stirred at room temperature for 30 min. All volatiles were removed in vacuo and the residue was co-evaporated with CH$_2$Cl$_2$ (2×20 mL). The resulting oil was taken up in ethyl acetate/MeOH (5:1; 3.0 mL) and then ethereal HCl (2.0 M in diethyl ether; 0.5 mL, 1.0 mmol) was added. The precipitate formed was isolated and dried under reduced pressure to afford (Z)-4-(2-(aminomethyl)-3-fluoroallyloxy)-N,N-dimethylbenzenesulfonamide hydrochloride (196.0 mg, 84%) as a white solid; m.p. 185-187° C.; $^1$H-NMR (300 MHz; d$_6$-DMSO) δppm: 3.39 (6 H, br s), 3.54 (2 H, br s), 4.81 (2 H, d, J 2.3 Hz), 7.16 (2 H, d, J 9.0 Hz), 7.24 (1 H, d, J 82.3 Hz), 7.25 (2 H, br s), 7.77 (2 H, d, J 9.0 Hz).

EXAMPLE 3

The following compounds were prepared according to procedures A and B as set forth in Example 2.

(Z)-4-(2-(Aminomethyl)-3-fluoroallyloxy)-N-tert-butyl-benzamide hydrochloride (Compound 1):

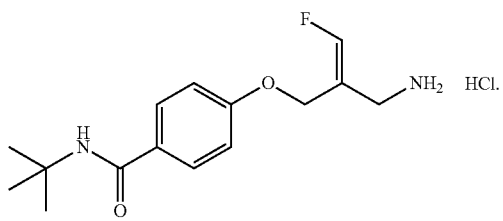

Beige solid; m.p. 180-184° C.; $^1$H-NMR (300 MHz; CD$_3$OD) δ ppm: 1.45 (9 H, s), 3.70 (2H, d, J 2.2 Hz), 4.86 (2 H, dd, J 2.9, 0.7 Hz), 7.06 (2 H, d, J 9.0 Hz), 7.13 (1 H, d, J 80.9 Hz), 7.76 (2 H, d, J 8.9 Hz).

(Z)-4-(2-(Aminomethyl)-3-fluoroallyloxy)-3-fluoro-N,N-dimethyl-benzamide hydrochloride (Compound 4):

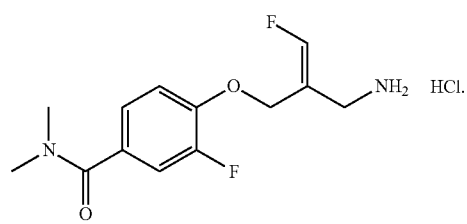

Brown solid; $^1$H-NMR (300 MHz; CD$_3$OD) δ ppm: 3.04 (3 H, br s), 3.09 (3 H, br s), 3.73 (2 H, d, J 2.4 Hz), 4.93 (2 H, dd, J 2.9, 0.8 Hz), 7.16 (1 H, d J 90.0 Hz), 7.25-7.29 (2 H, m)

(Z)-4-(2-(Aminomethyl)-3-fluoroallyloxy)-3-chloro-N,N-dimethyl-benzamide hydrochloride (Compound 6):

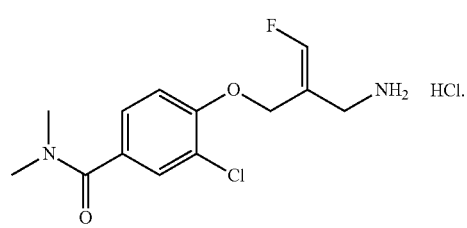

Brown solid; $^1$H-NMR (300 MHz; CD$_3$OD) δ ppm: 3.04 (3 H, br s), 3.09 (3 H, br s), 3.76 (2 H, d, J 2.3 Hz), 4.96 (2 H, dd, J 2.8, 0.9 Hz), 7.16 (1 H, d, 80.6 Hz), 7.26 (1 H, d, J 8.6 Hz), 7.43 (1 H, dd, J 8.5, 2.1 Hz), 7.55 (1 H, d, J 2.0 Hz)

(Z)-4-(2-(Aminomethyl)-3-fluoroallyloxy)-3-bromo-N,N-dimethyl-benzamide hydrochloride (Compound 20):

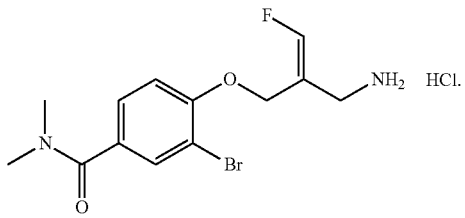

Beige-coloured solid; m.p. 54-57° C.; $^1$H-NMR (300 MHz; CD$_3$OD) δ ppm: 3.04 (3 H, br s), 3.09 (3 H, br s), 3.78 (2 H, d, J 2.4 Hz), 4.95 (2 H, dd, J 2.9, 0.9 Hz), 7.15 (1 H, d, J 80.5 Hz), 7.22 (1 H, d, J 8.5 Hz), 7.47 (1 H, dd, J 8.5, 2.1 Hz), 7.71 (1 H, d, J 2.0 Hz)

4-(2-(Aminomethyl)-3-fluoroallylthio)-N,N-dimethyl-benzamide hydrochloride as a mixture of E and Z isomers (Compounds 8E and 8Z):

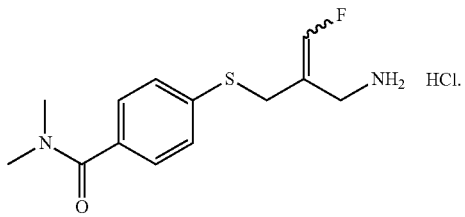

Colorless solid; $^1$H-NMR (300 MHz; CD$_3$OD) δ ppm: 2.99 (3 H, br s), 3.00 (3 H, br s), 3.10 (6 H, br s), 3.64 (2 H, d, J 3.0 Hz), 3.71 (2 H, dd, J 3.1, 1.1 Hz), 3.77 (2 H, d, J 1.0 Hz), 3.87 (2 H, dd, J 2.1, 0.8 Hz), 6.82 (1 H, d, J 82.1 Hz), 6.93 (1 H, d, J 81.6 Hz), 7.38 (2 H, d, J 8.6 Hz), 7.41 (2 H, d, J 8.6 Hz), 7.48 (2 H, d, J 8.6 Hz), 7.49 (2 H, d, J 8.3 Hz).

(E)-4-(2-(Aminomethyl)-3-fluoroallyloxy)-N-isopropyl-benzamide trifluoroacetate (Compound 39):

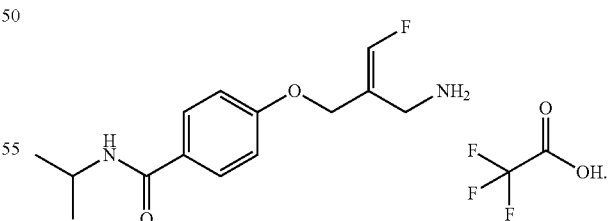

Yellow gum; $^1$H-NMR (300 MHz; d$_6$-DMSO) δppm: 1.13 (6 H, d, J 6.9 Hz), 3.58 (2 H, d, J 5.1 Hz), 4.05 (1 H, septet, J 6.6 Hz), 4.65 (2 H, d, J 3.6 Hz), 7.02 (2 H, d, J 6.9 Hz), 7.32 (1 H, d, J 81.9 Hz), 7.82 (2 H, d, J 6.9 Hz), 8.07 (1 H, d, J 7.5 Hz), 8.18 (3 H, br s).

(E)-4-(2-(Aminomethyl)-3-fluoroallyloxy)-N-tert-butyl-benzamide hydrochloride (Compound 23):

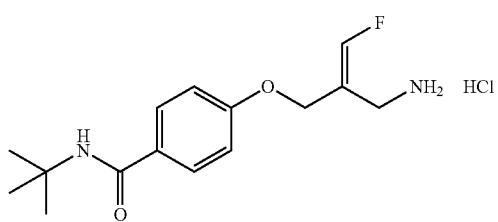 [SMILES: CC(C)(C)NC(=O)c1ccc(OC/C(=C/F)CN)cc1 ; Cl]

Colorless powder; m.p. 140-142° C.; ¹H-NMR (300 MHz; d₆-DMSO) δppm: 1.37 (9 H, s), 3.60 (2 H, d, J 3.9 Hz), 4.68 (2 H, d, J 3.6 Hz), 7.02 (2 H, d, J 6.9 Hz), 7.34 (1 H, d, J 82.5 Hz), 7.61 (1 H, s), 7.81 (2 H, d, J 6.9 Hz), 8.28 (3 H, br s).

(E)-4-(2-(Aminomethyl)-3-fluoroallyloxy)-N,N-diethylbenzamide hydrochloride (Compound 24):

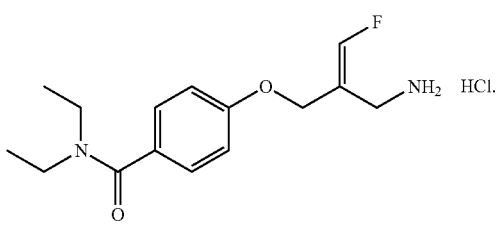

Brown solid; ¹H-NMR (300 MHz; CD₃OD) δ ppm: 1.18 (3 H, br s), 1.25 (3 H, br s), 3.37 (2 H, br s), 3.56 (2 H, br s), 3.83 (2 H, s), 4.68 (2 H, d, J 3.5 Hz), 7.12 (2 H, d, J 8.6 Hz), 7.40 (2 H, d, J 8.7 Hz).

(E)-4-(2-(Aminomethyl)-3-fluoroallyloxy)-N-methylbenzamide hydrochloride (Compound 25):

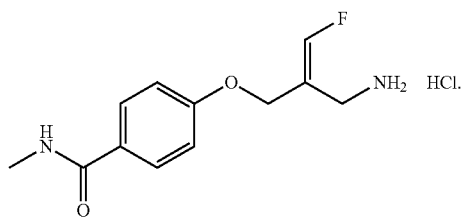

Colorless solid; m.p. 203-205° C.; ¹H-NMR (300 MHz; CD₃OD) δ ppm: 2.90 (3 H, s), 3.83 (2 H, d, J 1.8 Hz), 4.67 (2 H, dd, J 3.7, 0.8 Hz), 7.07 (2 H, d, J 9.0 Hz), 7.24 (1 H, d, J 81.2 Hz), 7.81 (2 H, d, J 9.0 Hz).

(Z)-4-(2-(Aminomethyl)-3-fluoroallyloxy)benzamide hydrochloride (Compound 2):

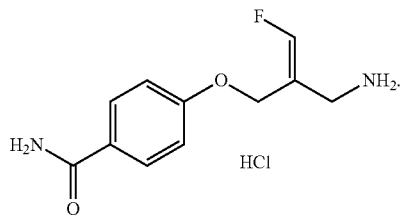 [SMILES: NC/C(=C/F)COc1ccc(C(N)=O)cc1 ; Cl]

Colorless solid; m.p. 195-198° C.; 1H-NMR (300 MHz; MeOD) δppm: 3.72 (2H, d, J 2.2 Hz), 4.90 (2H, dd, J 2.9, 0.8 Hz), 7.11 (2H, d, J 9.0 Hz), 7.14 (1H, d, J 80.8 Hz), 7.90 (2H, d, J 9.0 Hz).

(E)-4-(2-(Aminomethyl)-3-fluoroallyloxy)benzamide hydrochloride (Compound 3):

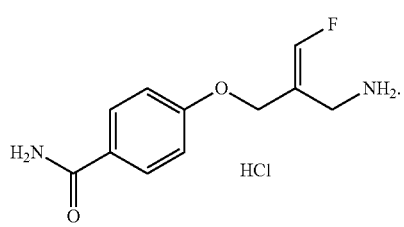 [SMILES: NC/C(=C\F)COc1ccc(C(N)=O)cc1 ; Cl]

Colorless solid; m.p. 225-228° C.; 1H-NMR (300 MHz; MeOD) δppm: 3.85 (2H, s), 4.70 (2H, dd, J 3.6, 1.0 Hz), 7.10 (2H, d, J 9.0 Hz), 7.26 (1H, d, J 81.2 Hz), 7.90 (2H, d, J 9.0 Hz).

(E)-4-(2-(Aminomethyl)-3-fluoroallyloxy)-N,N-dimethylbenzamide hydrochloride (Compound 13):

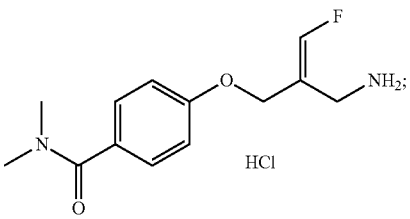 [SMILES: CN(C)C(=O)c1ccc(OC/C(=C/F)CN)cc1 ; Cl]

m.p. 185-187° C.; ¹H-NMR (300 MHz; d₆-DMSO) δppm: 2.95 (6 H, s), 3.60 (2 H, d (br), J 4.2 Hz), 4.67 (2 H, d, J 3.6 Hz), 7.03 (2 H, d, J 8.7 Hz), 7.33 (1 H, d, J 82.2), 7.40 (2 H, d, J 8.7 Hz), 8.29 (3 H, br s).

(Z)-4-(2-(Aminomethyl)-3-fluoroallyloxy)-N,N,2-trimethylbenzamide hydrochloride (Compound 26):

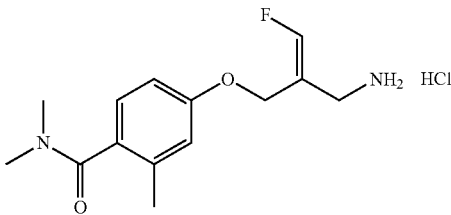 [SMILES: Cc1cc(OC/C(=C\F)CN)ccc1C(=O)N(C)C ; Cl]

¹H-NMR (300 MHz; DMSO) δppm: 2.17 (3 H, s), 2.75 (3 H, s), 2.98 (3 H, s), 3.54 (2 H, m (br)), 4.72 (2 H, d, J 2.4 Hz), 6.85 (1 H, dd, J 2.4, 8.4 Hz), 6.89 (1 H, d, J 2.4 Hz), 7.10 (1 H, d, J 8.4 Hz), 7.21 (1 H, d, J 82.2 Hz), 8.15 (3 H, s).

4-(2-(Aminomethyl)-3-fluoroallyloxy)-3-methoxy-N,N-dimethylbenzamide hydrochloride as a mixture of E and Z isomers (Compounds 7E and 7Z):

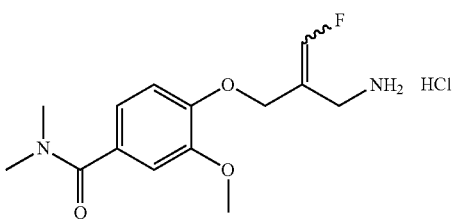 [SMILES: COc1cc(C(=O)N(C)C)ccc1OCC(=CF)CN ; Cl]

E-Isomer

¹H-NMR (300 MHz; DMSO) δppm: 2.95 (6 H, s), 3.52 (2 H, m (br)), 3.79 (3 H, s), 4.65 (2 H, d, J 3.3 Hz), 6.95-7.09 (3 H, m), 7.24 (1 H, d, J 82.0 Hz), 8.25 (3 H, s).

Z-Isomer

¹H-NMR (300 MHz; DMSO) δppm: 2.95 (6 H, s), 3.59 (2 H, m (br)), 3.79 (3 H, s), 4.77 (2 H, d, J 2.1 Hz), 6.95-7.09 (3 H, m), 7.29 (1 H, d, J 82.0 Hz), 8.25 (3 H, s).

EXAMPLE 4

The following compounds were prepared according to procedures C and D as set forth in Example 2.

(E)-4-(2-(Aminomethyl)-3-fluoroallyloxy)benzenesulfonamide hydrochloride (Compound 11):

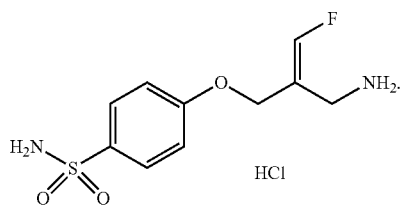 [SMILES: NC/C(=C\F)COc1ccc(S(N)(=O)=O)cc1 ; Cl]

Colorless solid; m.p. 107-110° C.; 1H-NMR (300 MHz; MeOD) δppm: 3.85 (2H, d, J 2.0 Hz) 4.71 (2H, dd, J 3.6, 0.8 Hz), 7.16 (2H, d, J 9.0 Hz), 7.27 (1H, d, J 81.5 Hz), 7.88 (2H, d, J 9.0 Hz).

(E)-4-(2-(Aminomethyl)-3-fluoroallyloxy)-N,N-dimethylbenzenesulfonamide hydrochloride (Compound 14):

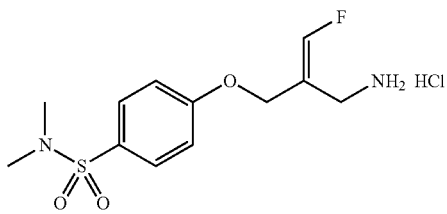 [SMILES: CN(C)S(=O)(=O)c1ccc(OC/C(=C/F)CN)cc1 ; Cl]

m.p. 178-180° C.; ¹H-NMR (300 MHz; d₆-DMSO) δppm: 2.57 (6 H, s), 3.61 (2 H, d (br), J 2.1 Hz), 4.73 (2 H, d, J 3.3 Hz), 7.22 (2H, d, J 8.7 Hz), 7.36 (1 H, d, J 82.2 Hz), 7.71 (2 H, d, J 8.7 Hz), 8.29 (3 H, brs).

(Z)-3-(2-(Aminomethyl)-3-fluoroallyloxy)-N,N-dimethylbenzenesulfonamide hydrochloride (Compound 15):

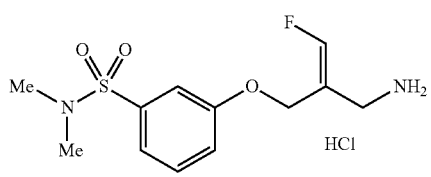 [SMILES: CN(C)S(=O)(=O)c1cccc(OC/C(=C\F)CN)c1 ; Cl]

Off white solid; m.p. 140-142° C.; ¹H-NMR (300 MHz; CD₃OD) δ ppm: 2.70 (6 H, s), 3.71 (2 H, d, J 2.3 Hz), 4.90 (2 H, dd, J 2.9, 0.8 Hz), 7.14 (1 H, d, J 80.8 Hz), 7.31-7.62 (4 H, m).

(E)-4-(2-(Aminomethyl)-3-fluoroallyloxy)-N-methylbenzenesulfonamide hydrochloride (Compound 28):

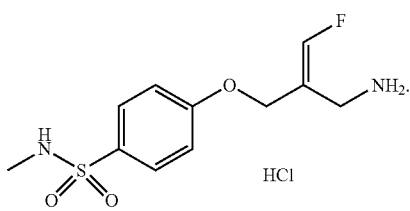 [SMILES: CNS(=O)(=O)c1ccc(OC/C(=C/F)CN)cc1 ; Cl]

Beige solid; m.p. 143-146° C.; 1H-NMR (300 MHz; MeOD) δppm: 2.51 (3H, s), 3.85 (2H, s), 4.73 (2H, d, J 3.3 Hz), 7.19 (2H, d, J 8.8 Hz), 7.27 (1H, d, J 81.0 Hz), 7.80 (2H, d, J 8.7 Hz).

(Z)-4-(2-(Aminomethyl)-3-fluoroallyloxy)-N-methylbenzenesulfonamide hydrochloride (Compound 29):

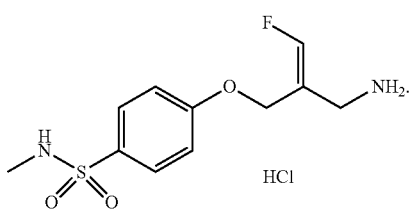 [SMILES: CNS(=O)(=O)c1ccc(OC/C(=C\F)CN)cc1 ; Cl]

Colorless solid; m.p. 178-180° C.; 1H-NMR (300 MHz; d6-DMSO) δppm: 2.38 (3H, d, J 5.0 Hz), 3.55 (2H, br s), 4.81 (2H, d, J 2.3 Hz), 7.20 (2H, d, J 8.9 Hz), 7.25 (1H, d, J 82.0 Hz), 7.34 (1H, q, J 5.1 Hz), 7.73 (2H, d, J 8.9 Hz), 8.15 (3H, br s).

(E)-4-(2-(Aminomethyl)-3-fluoroallyloxy)-N-ethylbenzenesulfonamide hydrochloride (Compound 30):

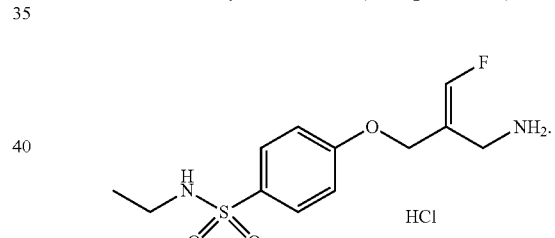

Colorless solid; m.p. 80-85° C.; 1H-NMR (300 MHz; MeOD) δppm: 1.06 (3H, t, J 7.3 Hz), 2.88 (2H, q, J 7.2 Hz), 3.85 (2H, d, J 2.0 Hz), 4.72 (2H, dd, J 3.6, 0.8 Hz), 7.18 (2H, d, J 9.0 Hz), 7.27 (1H, d, J 81.0 Hz), 7.82 (2H, d, J 9.0 Hz).

(Z)-4-(2-(Aminomethyl)-3-fluoroallyloxy)-N-ethylbenzenesulfonamide hydrochloride (Compound 31):

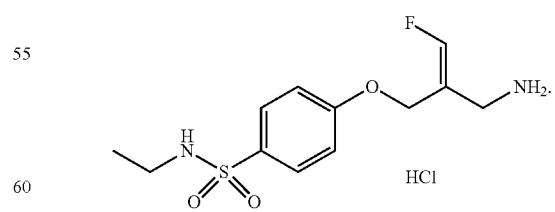

White solid; m.p. 65-67° C.; ¹H-NMR (300 MHz; d₆-DMSO) δppm: 0.96 (3H, t, J 7.2 Hz), 2.74 (2H, dq, J 7.0, 7.2 Hz), 3.55 (2H, br s), 4.80 (2H, br s), 7.19 (2H, d, J 8.8 Hz), 7.25 (1H, d, J 81.9 Hz), 7.44 (1H, t, J 5.5 Hz), 7.74 (2H, d, J 8.7 Hz), 8.16 (3H, br s).

(E)-4-(2-(Aminomethyl)-3-fluoroallyloxy)-N-isopropyl-benzenesulfonamide hydrochloride (Compound 32):

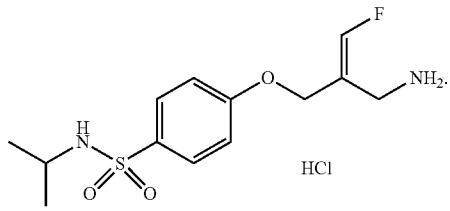 [SMILES: CC(C)NS(=O)(=O)c1ccc(OC/C(=C/F)CN)cc1 ; Cl]

Colorless solid; m.p. 151-153° C.; 1H-NMR (300 MHz; MeOD) δppm: 1.03 (6H, d, J 6.6 Hz), 3.33 (1H, m) 3.85 (2H, s), 4.72 (2H, d, J 3.8 Hz), 7.17 (2H, d, J 9.0 Hz), 7.27 (1H, d, J 80.9 Hz), 7.83 (2H, d, J 8.9 Hz).

(Z)-4-(2-(Aminomethyl)-3-fluoroallyloxy)-N-isopropyl-benzenesulfonamide hydrochloride (Compound 33):

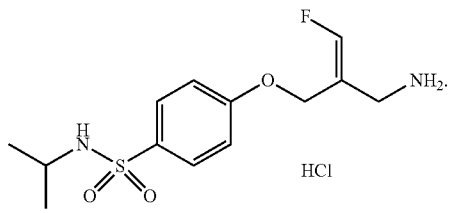 [SMILES: CC(C)NS(=O)(=O)c1ccc(OC/C(=C\F)CN)cc1 ; Cl]

White solid; m.p. 50-52° C.; $^1$H-NMR (300 MHz; $d_6$-DMSO) δppm: 0.94 (6H, d, J 6.5 Hz), 3.18 (1H, m), 3.56 (2H, br s), 4.81 (2H, br s), 7.18 (2H, d, J 8.9 Hz), 7.25 (1H, d, J 81.9 Hz), 7.46 (1H, d, J 7.1 Hz), 7.76 (2H, d, J 8.9 Hz), 8.09 (3H, br s).

(Z)-4-(2-(Aminomethyl)-3-fluoroallyloxy)benzenesulfonamide hydrochloride (Compound 9):

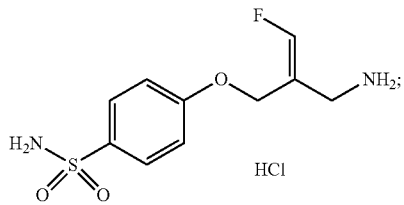 [SMILES: NC/C(=C/F)COc1ccc(S(N)(=O)=O)cc1 ; Cl]

m.p. 227-230° C.; $^1$H-NMR (300 MHz; $d_6$-DMSO) δppm: 3.54 (2 H, br), 4.80 (2 H, s), 7.24 (1 H, d, J 82.2 Hz), 7.15 (2 H, d, J 8.7 Hz), 7.26 (2 H, s), 7.77 (2 H, d, J 8.7 Hz), 8.14 (3 H, br s).

EXAMPLE 5

Method to Determine the Ability of Compounds of Formula I to Inhibit Human Recombinant SSAO/VAP-1

The inhibitory effects of all the compounds of Formula I were tested against human recombinant SSAO/VAP-1 using the coupled colorimetric method as described for monoamine oxidase, copper-containing amine oxidases and related enzymes (Holt A. and Palcic M., A peroxidise-coupled continuous absorbance plate-reader assay for flavin monoamine oxidases, copper-containing amine oxidases and related enzymes. *Nat. Protoc.* 2006, 1, 2498-2505). Briefly, a cloned cDNA template corresponding to residues 34-763 of human SSAO/VAP-1, and incorporating a mouse Ig kappa (κ) signal sequence, N-terminal Flag epitope tag and tobacco etch virus (TEV) cleavage site, was assembled in a mammalian expression vector (pLO-CMV) by Geneart AG. This vector containing human SSAO/VAP-1 residues was transfected into CHO-K1 glycosylation mutant cell line, Lec 8. A clone stably expressing human SSAO/VAP-1 was isolated and cultured in large scale. Active human SSAO/VAP-1 was purified and recovered using immunoaffinity chromatography. This was used as source for SSAO/VAP-1 activity. A high-throughput colorimetric assay was developed using either 96 or 384 well format. Briefly, in a standard 96 well plate assay 50 μL of purified human SSAO/VAP-1 (0.25 μg/mL) in 0.1 M NaPO4 buffer (pH 7.4) was added into each well. Test compounds were dissolved in DMSO and tested in a Concentration Response Curve (CRC) with 4-9 data points, typically in the micromolar or nanomolar range after incubation with human SSAO/VAP-1 for 30 min at 37° C. After 30 min incubation, 50 μL of the reaction mixture containing 600 μM benzylamine (Sigma Aldrich), 120 μM Amplex Red (Sigma Aldrich) and 1.5 U/mL horseradish peroxidase (Sigma Aldrich) prepared in 0.1 M NaPO4 buffer (pH 7.4) were added to the corresponding well. The fluorescence unit (RFU) was read every 2.5 min for 30 min at 37° C. excitation 565 nm and emission 590 (Optima; BMG labtech). The slope of the kinetics for each well was calculated using MARS data analysis software (BMG labtech) and this value was used to deduce the $IC_{50}$ value (Dotmatics). The results are shown in Table 2.

TABLE 2

SSAO/VAP-1, MAO-B and DAO inhibitory activities of examples of compounds of the invention and comparative compounds

| Compound | Human MAO-B Activity $IC_{50}$ (micromolar) | Human SSAO/VAP-1 expressed in HMEC cells Activity $IC_{50}$ (nanomolar) | Endogenous SSAO/VAP-1 in rat fat Activity $IC_{50}$ (nanomolar) | Human Diamine Oxidase Activity $IC_{50}$ (micromolar) |
|---|---|---|---|---|
| 1 | <1 | <100 | <100 | <1 |
| 2 | >1 | <100 | <100 | <0.1 |
| 3 | >10 | <100 | <100 | >1 |
| 4 | >0.1 | <100 | <100 | <1 |
| 6 | >1 | <100 | NT | <1 |
| 7 | >10 | <100 | NT | <1 |
| 8 | >1 | <100 | NT | NT |
| 9 | >10 | <100 | <100 | <1 |
| 10 | >10 | <100 | <100 | >1 |
| 11 | >10 | <100 | <100 | >10 |
| 13 | >0.1 | <100 | <100 | >1 |
| 14 | >10 | <100 | <100 | >10 |
| 15 | >100 | <100 | <100 | NT |
| 18 | >0.1 | <100 | <100 | <0.1 |
| 20 | >1 | <100 | NT | <1 |
| 23 | >1 | <100 | <100 | >10 |
| 24 | >1 | <100 | <100 | >10 |
| 25 | >1 | <100 | <100 | <1 |
| 26 | >1 | <100 | NT | <1 |
| 28 | >10 | <100 | <100 | >10 |
| 29 | >10 | <100 | <100 | >1 |
| 30 | >10 | <100 | <100 | >10 |
| 31 | >1 | <100 | <100 | <1 |
| 32 | >10 | <100 | <100 | >10 |
| 33 | >10 | <100 | <100 | <1 |
| Mofegiline | 5 nM | 19 | 6 | >10 |

EXAMPLE 6

Method to Determine the Ability of Compounds of Formula I to Inhibit Human Recombinant SSAO/VAP-1 Expressed in HMEC Cells SSAO/VAP-1 activity was determined using a similar method as described in Example 5 except for the source of human SSAO/VAP-1. pcDNA-DEST40-hSSAO/VAP-1 was transfected into HMEC cells using lipofectamine (Invitrogen Ltd). A clone stably expressing human SSAO/VAP-1 was selected and was stored in liquid nitrogen until cell lysate was required for colorimetric assay. Briefly, HMEC cell expressing human SSAO/VAP-1 were grown in several 10 cm petri dishes, once the cells reached 100% confluency, cells were harvested and homogenates were prepared. Cells were washed twice with 5 mL of chilled HES buffer (20 mM HEPES, 1 mM EDTA, 250 mM sucrose, pH 7.4). HES buffer containing 1× protease inhibitor (Sigma Aldrich) and added and cells were incubated on ice for 3 min. Buffer was removed and cells were scraped and transferred to a centrifuge tube. Cell lysates were prepared by passing through 23 G needle for 10 times and followed by 27 G needle for 10 times. Alternatively the cell lysates were prepared by using IKA Ultra-Turrax T 10 homogenizer for 3 min for every 10 mL of cell suspensions. Cells were then spun for 5 min at 300×g. The clear supernatant was transferred to new centrifuge tube and stored at −80° C. until colorimetric assay was performed. Prior to the assay, 0.5 mM pargyline was added in order to inhibit any residue MAO activities. The assay was performed as described in Example 5. Briefly, 50 µL of cell lysate was incubated with test compounds for 30 min at 37° C. Reaction mixtures were added and kinetic was read as described in detail in Example 5. Table 2 shows the data of several compounds of Formula I.

EXAMPLE 7

Method to Determine the Ability of Compounds of Formula I to Inhibit SSAO/VAP-1 in Mouse and Rat Fat Homogenate Abdominal fat from BALB/c mice, Wistar or Sprague Dawley rats, which are tissues enriched with SSAO/VAP-1—were surgically removed. For every gram of animal abdominal fat tissue, 1 mL of 0.1 M NaPO4 buffer (pH 7.4) was added. Tissues were homogenized using IKA Ultra-Turrax T 10 homogenizer for 3 min, homogenate was centrifuged for 15 min at 3000×g. The middle layer (clear supernatant) was removed without disturbing the top layer (high fat content) or the debris on the bottom of the tube. SSAO/VAP-1 activity was determined by checking the fluorescent signal. $K_m/V_{max}$ values were determined and the fat homogenate was aliquoted and stored at −80 C until assays were performed. Assay was performed in a similar fashion as for human SSAO/VAP-1 (Example 5) except, the substrate (benzylamine) concentrations used for mouse fat homogenate and rat fat homogenate were 80 µM and 30 µM respectively. The results are shown in Table 2.

EXAMPLE 8

Method to Determine the Ability of Compounds of Formula I to Inhibit Human Recombinant MAO-B The specificity of invention compounds was tested by determining their ability to inhibit MAO-B activities in vitro. Recombinant human MAO-B (0.06 mg/mL; Sigma Aldrich) was used as source of MAO-B enzyme activities. The assay was performed in a similar way as for human SSAO/VAP-1 (Example 5) except, the substrate benzylamine was used at 100 µM. Table 2 shows data for several compounds of Formula I.

EXAMPLE 9

Method to Determine the Ability of Compounds of Formula I to Inhibit Human Recombinant Diamine Oxidase Three human genes are found to encode for copper-containing amine oxidases. Diamine oxidase (DAO) is one of the enzymes produced by the AOC1 gene, named for its substrate preference for diamines. The specificity of the compounds of Formula I was tested by determining their ability to inhibit DAO activities in vitro. Recombinant human DAO (2.4 µg/mL) was used as source of DAO enzyme activities. The assay was performed as described in the method for human SSAO/VAP-1 (Example 5) except the substrate used was 200 µM putrescine, and the control wells contained 10 µM aminoguanidine instead of Mofegiline. Table 2 shows data for several compounds of Formula I.

EXAMPLE 10

Method to Determine the Ability of Compounds of Formula I to Inhibit Lysyl Oxidase Lysyl oxidase (LOX) is an extracellular copper dependent enzyme which oxidizes peptidyl lysine and hydroxylysine residues in collagen and lysine residues in elastin to produce peptidyl alpha-aminoadipic-delta-semialdehydes. This catalytic reaction can be irreversibly inhibited by β-aminopropionitrile (βAPN) that binds to the active site of LOX (Tang S. S., Trackman P. C. and Kagan H. M., Reaction of aortic lysyl oxidase with beta-aminoproprionitrile. J. Biol. Chem. 1983, 258, 4331-4338). There are five LOX family members; these are LOX, LOXL1, LOXL2, LOXL3 and LOXL4. The specificity of compounds of Formula I was tested by determining their ability to inhibit different sources of LOX family in vitro.

Two sources of enriched LOX were prepared using (1) supernatant from normal human lung fibroblast (NHLF) and (2) homogenate from rat skin. Briefly, NHLF was cultured in complete medium containing SingleQuot supplements with 5% FBS (Lonza Australia Pty Ltd) and FGM-2 medium (Lonza Australia Pty Ltd) in T175 flask until 60% to 80% confluency. Once the optimal confluency was reached, cells were washed twice using phosphate saline buffer and replaced with medium containing 0.1% FBS and FGM-2 medium. Two to four days later, supernatant was collected and centrifuged for 5 min at 300×g. Cell debris was removed and LOX proteins were further enriched using Amicon® Ultra-4 Centrifugal Filter Units, with a 10 kDa cut-off (Millipore Ltd). Briefly, samples were added to the columns and centrifuged at 4000×g, 4° C. until a final volume of 1 mL was obtained. During the centrifugation process, buffer was exchanged using sodium borate buffer (1.2 M Urea; 0.05 M sodium borate; pH 8.2). Different substrates were tested on the enriched LOX supernatant and the fluorescent signals were measured using colorimetric assay. The substrate specificity and pharmacology properties of the enriched supernatant were corroborated with published literatures. The enriched supernatant was aliquoted and stored at −80° C.

LOX proteins are found highly expressed on skin (Rucker et al 1995), thus rat skin homogenate were used as a second source for determining LOX enzyme activities. Briefly, to every gram of finely chopped rat skin tissue, 3 mL of phosphate buffered saline was added. Tissues were then homogenized using IKA Ultra-Turrax T 10 homogenizer for 3 min. This and all the following homogenizations were performed on ice. The homogenate was centrifuged (20817× g, 30 min) at 4° C. and the supernatant was discarded. Tissues were resuspended using 4.2M urea-sodium borate buffer and homogenized for approximately 3 min (2.5 mL buffer/g). Homogenate was incubated overnight at 4° C. Sample was spun (20817×g, 30 min) and supernatants were collected. Cell pellet underwent two cycles of homogenization and the supernatant from each process was collected. All the supernatants were pooled and LOX proteins in rat skin homogenate were enriched using Amicon® Ultra-4 Centrifugal Filter Units, with a 10 kDa cut-off. Sample underwent buffer exchange until a concentration of 1.2 M urea was reached. Different substrates were tested on the enriched LOX skin homogenate and the fluorescent signals were measured using colorimetric assay. The substrate specificity and pharmacology properties were determined. The enriched skin homogenate was aliquoted and stored at −80° C.

The specificity of compounds of Formula I was tested using the two different sources of LOX supernatant from normal human lung fibroblast (NHLF) and homogenate from rat skin. Assays were performed as described in the method for human SSAO/VAP-1 (Example 5 except these two sources were treated with pargyline (0.5 mM), the substrate used was 10 mM putrescine, the control wells contained 10 µM βAPN instead of Mofegiline, and was read at 45° C. Table 2 shows data for several compounds of Formula I.

EXAMPLE 11

Method to Determine the Ability of Compounds of Formula I to Inhibit SSAO/VAP-1 when Administered to Mice and Rats Mice and rats were administered either orally (p.o.) or intravenously (i.v.) with invention compounds at various concentrations ranging from 0.1 mg/Kg to 100 mg/Kg. Control group were administered the same volume of vehicle p.o. or i.v. Abdominal fats, plasma and lung, liver and aorta tissue were collected at various time points ranging from 0 to 96 hours.

Each tissue was homogenized in HES buffer with 1× phosphatase inhibitor (Sigma Aldrich) and 1× protease inhibitor (5 mL/g for rats and 20 mL/g for mice). The homogenate was used to measure SSAO activity as described in human SSAO/VAP-1 (Example 5), except the mice and rat homogenate was further diluted using 0.1 M NaPO4 buffer (pH 7.4) at 1:5 and 1:20 ratio, respectively. The substrate (benzylamine) concentrations used for mouse fat homogenate and rat fat homogenate were 80 µM and 30 µM respectively. The slope of the kinetics for each well was calculated using MARS data analysis software. The percentage response was calculated using the SSAO activity from treated animal tissue normalized to control animals. Graphs were plotted using GraphPad Prism Software. The method described by Yu, P. H. et al., Involvement of SSAO-mediated deamination in adipose glucose transport and weight gain in obese diabetic KKay mice, *Am J Physiol Endocrinol Metab* 2004, 286: E634-E64 was used to determine the degree of SSAO/VAP-1 inhibition in plasma. FIGS. 1A-1E, 2A-2E and 3A-3E show the dose response profile for Compound 23 in all tissues employing various administration protocols.

EXAMPLE 12

Inhibition of Carrageenan-Induced Rat Paw Edema

Carrageenan-induced paw edema is a widely used test to determine the anti-inflammatory activity of various therapeutic agents and is a useful experimental system for assessing the efficacy of compounds to alleviate acute inflammation. Inflammation is induced by intraplantar injection of 20 µL of carrageenan suspension (1% in saline) as described (see Roussin, A. et al., Neutrophil-associated inflammatory responses in rats are inhibited by phenylarsine oxide. *Eur. J. Pharmacol*, 1997, 322, 91-96 and Wise, L. E. et al., Evaluation of fatty acid amides in the carrageenan-induced paw edema model. *Neuropharmacology*, 2008. 54, 181-188). Test compound (0.1-100 mg/kg) is given 1 hour prior to the administration of carrageenan. Paw thickness is measured with electronic digital calipers prior to and 1, 3, 5, 6 and 24 hours after the carrageenan injection, to demonstrate greater than 50% inhibition of edema as compared to control animals.

EXAMPLE 13

Efficacy in Model of Systemic Inflammation

Evaluation of the efficacy of compounds of the invention is carried out in a model of endotoxemia that consists of intraperitoneal injection of a high dose of lipopolysaccharisde (LPS) (5 mg/kg) (see Schabbauer, G. et al., PI3K-Akt pathway suppresses coagulation and inflammation in endotoxemic mice. *Arterioscler. Thromb. Vasc. Biol.*, 2004, 24, 1963-1969 and Lentsch, A. B. et al., STAT4 and STAT6 regulate systemic inflammation and protect against lethal endotoxemia. *J. Clin. Invest.*, 2001, 108, 1475-1482). Blood samples (50 mL) are collected at 0, 1, 2, 4, and 8 hrs after LPS injection and used for blood smears and cytokine evaluation. Plasma concentrations of TNF-α, IL-6, MCP-1 and KC in mice treated with compound (0.1-100 mg/kg) are reduced between 20-80% as measured by ELISA. Animal survival rates are recorded for the next 3 days and compound treated mice show a 20% greater survival rate.

EXAMPLE 14

Inhibition of Air Pouch Inflammation in the Mouse

Injection of carrageenan induces inflammation and the pouch serves as a reservoir of cells and mediators that can be easily measured in the fluid that accumulates locally.

Animals were anaesthetized and 6 ml of sterile air was injected subcutaneously as described (see Romano, M. et al., Carrageenan-induced acute inflammation in the mouse air pouch synovial model. Role of tumour necrosis factor. *Mediators Inflamm*, 1997. 6, 32-38). After 3 days the pouches were re-injected with 3 ml of sterile air. On day 6, the controls received 1 ml of vehicle; treated controls received 10 mg/kg dexamethasone, and Compound 23 group received 2 mg/kg. 1 hour after treatment the mice were injected with 1 ml carrageenan solution into the air pouch.

At 4 hours after carrageenan injection, the animals were euthanized and the pouches were washed with saline. The exudates were used for cell count as well as cytokine measurement. Compound 23 treated mice showed reduced inflammation, with a significant reduction in exudate volume and neutrophil infiltration as well as significantly diminished TNF-α and IL-6 production (FIG. 4).

EXAMPLE 15

Inhibition of Leukocyte Migration in Cremaster Microcirculation

The mouse cremaster preparation was used to study the inhibition of leukocyte migration to the microcirculation and adjacent connective tissue as described (see Pinho, V. et al., Tissue- and Stimulus-Dependent Role of Phosphatidylinositol 3-Kinase Isoforms for Neutrophil Recruitment Induced by Chemoattractants In Vivo. *J Immunol* 2007; 179:7891-7898 and Nanhekhan, L.V., Microcirculatory hemodynamics of the rat cremaster muscle flap in reduced blood flow states. *Ann Plast Surg.* 2003 August; 51(2):182-8).

Briefly, an incision was made in the scrotal skin to expose the left cremaster muscle, which was then carefully removed from the associated fascia. A lengthwise incision was made on the ventral surface of the cremaster muscle using a cautery. The testicle and the epididymis were separated from the underlying muscle and were moved into the abdominal cavity. The muscle was then spread out over an optically clear viewing pedestal and was secured along the edges with a suture. The exposed tissue was superfused with warm bicarbonate-buffered saline. Single, unbranched cremasteric venules (25-40 um in diameter) were selected and, to minimize variability, the same section of cremasteric venule was observed throughout the experiment. The number of rolling, adherent, and emigrated leukocytes upon KC or LPS stimulation was determined offline during video playback analysis. Rolling leukocytes were defined as those cells moving at a velocity less than that of erythrocytes within a given vessel. The flux of rolling cells was measured as the number of rolling cells passing by a given point in the venule per minute. A leukocyte was considered to be adherent if it remained stationary for at least 30 s, and total leukocyte adhesion was quantified as the number of adherent cells within a 100 μm length of venule. Compound 23 (6 mg/kg) was given 1 hour prior to the administration of stimulus. Compound 23 demonstrated >50% inhibition of rolling and adhesion when compared to the control group (FIG. 5).

EXAMPLE 16

Inhibition of Inflammation Upon Induction of the Cecal Ligation and Perforation (CLP) Insult The CLP procedure involved a laparotomy and ligation of the cecum, distal to the ileocecal valve as described (see Martin, E. et al Phosphoinositide-3 Kinase γ Activity Contributes to Sepsis and Organ Damage by Altering Neutrophil Recruitment *Am. J. Respir. Crit. Care Med.* September, 2010 182 (6) 762-773 and Lutterloh, E. C., Inhibition of the RAGE products increases survival in experimental models of severe sepsis and systemic infection. *Crit Care.* 2007; 11(6):R122).

Figure 6A:
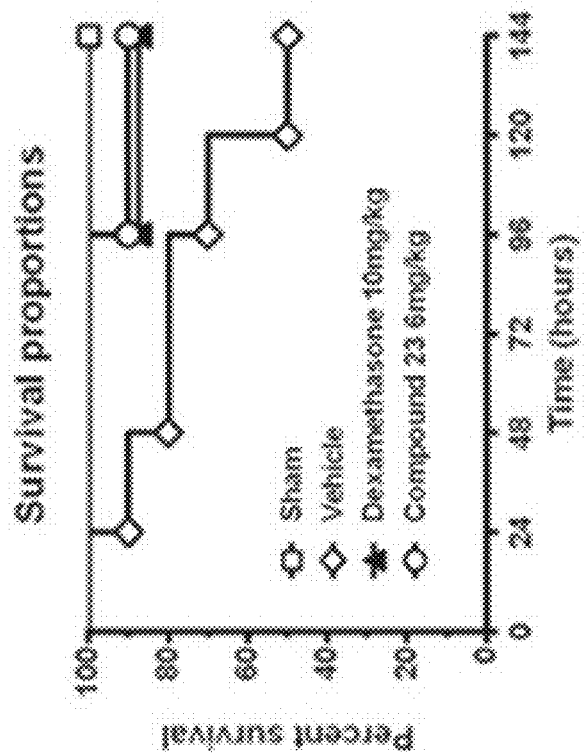
FIGS. 6A & 6B show the ability of Compound 23 to reduce inflammation in a cecal ligation and perforation (CLP) model in the mouse: Total cell count (FIG. 6A); Reduction of mortality (FIG. 6B).
Figure 6B:
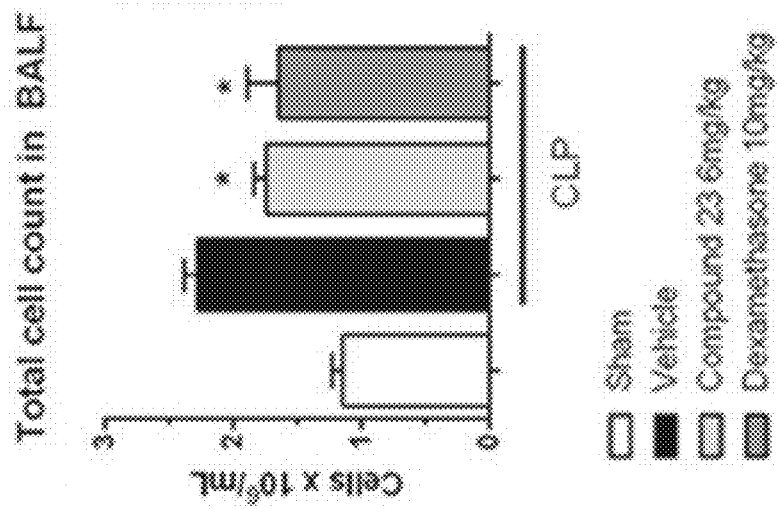
Figure 7A:
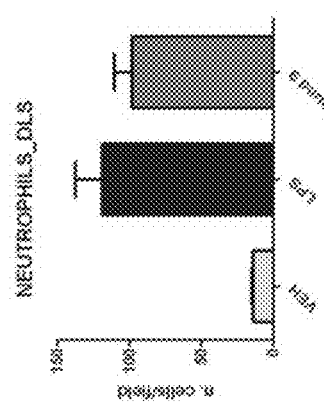
Figure 7B:
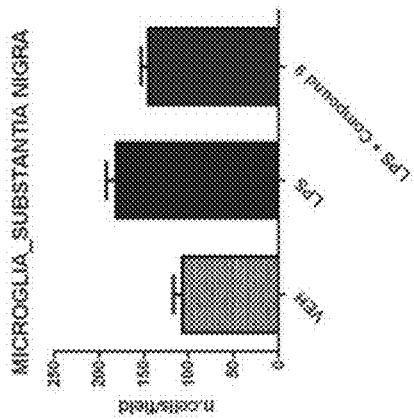
Figure 7C:
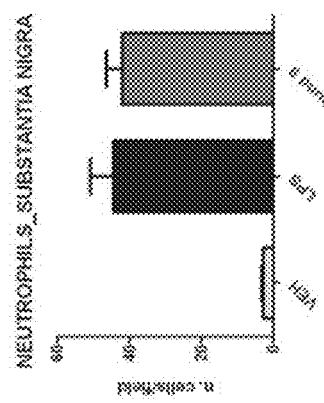
Figure 7D:
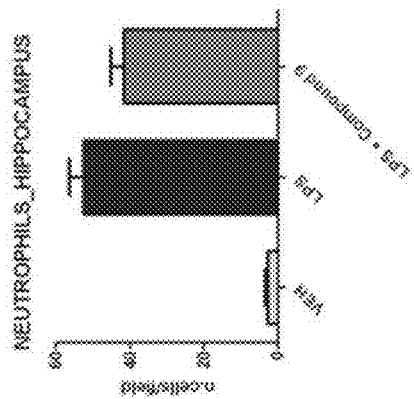

The cecum was punctured with a needle to induce moderate sepsis; following the puncture a small amount of fecal matter was extruded from each puncture Sham animals received a laparotomy with no manipulation of the cecum. Compound 23 was dosed 6 hours prior to puncture. Following ligation and puncture, the cecum was returned to the abdomen, the peritoneal wall and skin incisions were closed, and the animals were allowed to recover. Eighteen hours following CLP/sham surgery, a proportion of the animals from each group were sacrificed and the lungs were lavaged. The lavage was centrifuged to isolate inflammatory cells for differential cell analysis, while a separate aliquot was used to count total live cell number using a haemocytometer and light microscopy. Survival was monitored over 7 days. Compared with the vehicle-treated group that showed 50% lethality incidence, compound-treated mice resulted in a statistically significant reduction in lethality with 90% of mice surviving at day 7 (FIG. 6B). In addition, the inhibitory effect of the compound on the inflammatory component of disease was seen by reduced total leukocyte in the BALF (FIG. 6A).

EXAMPLE 17

Inhibition of Chemically Induced Colitis

This procedure is used to screen for compounds which inhibit the development of colitis as compared to control using the TNBS-induced colitis model (see Maslowski, K. M. et al., Regulation of inflammatory responses by gut microbiota and chemoattractant receptor GPR43. *Nature,* 2009. 461, 1282-1286). Briefly, mice are sensitised by applying a mixture of acetone/olive oil (50:50) with TNBS (50:50, total) on shaved skin between shoulder blades. Seven days later, mice are challenged intra-rectally with 2.5 mg TNBS with 50% ethanol, 3.5 cm from the anal verge. Mice are fasted overnight before the intrarectal challenge, and given 5% dextrose in the drinking water. Mice are analysed 3 days after TNBS challenge.

Colitis is also induced by dextran sulphate sodium salt (DSS), as described (see Vieira, A. T. et al., Treatment with a novel chemokine-binding protein or eosinophil lineage-ablation protects mice from experimental colitis. *Am. J. Pathol,* 2009. 175. 2382-2891). Mice receive 4% (w/v) DSS in their drinking water ad libitum for 7 days, then switch to autoclaved drinking water. Compounds are given throughout the experimental period at 0.1-100 mg/kg. Mice are sacrificed on the seventh day, and the colon is analysed. For survival studies, mice are followed for 25 days after start of DSS treatment. Compounds inhibit disease progression as evaluated by less weight loss (20%) and decreases clinical symptoms. They also delay presence of blood in stools and loss of firmness. Histological analysis of colon sections demonstrate >30% less inflammation. Cytokine measurement shows up to 70% inhibition of IL5, IL6 and TNFα production.

EXAMPLE 18

Inhibition of ConA Liver Induced Injury in Mice

Autoimmune liver disease includes autoimmune hepatitis (AIH), a distinct form of acute and chronic inflammatory liver disease in which immune reactions against host antigens have been found to be the major pathological mechanism. AIH may lead to severe liver disease such as liver cirrhosis. ConA-induced specific liver injury in mice is an experimental animal model, which has been closely studied in the pathogenesis of the liver injury. T cell mediated immunity and the subsequent release of TNF-α are considered to play an important role in this disease.

Concanavalin A (ConA) 10 mg/kg is administered intravenously in saline. Control mice are injected with saline. Transaminase and alkaline phosphatase in blood and liver are >40% reduced by compound at 0.1-100 mg/kg. Cytokines, such as IL-6, TNF-α and IL-5, are significantly reduced, showing up to 75% reduction when compared to control. Hepatic histopathology demonstrates decreased inflammation and tissue damage in the compound treated group (see Hu, X. D. et al., Preventive effects of 1,25-(OH)2VD3 against ConA-induced mouse hepatitis through promoting vitamin D receptor gene expression. *Acta Pharmacol. Sin,* 2010, 31, 703-708; Zhang, X. L. et al., Protective effects of cyclosporine A on T-cell dependent ConA-induced liver injury in Kunming mice. *World J. Gastroenterol.,* 2001, 7, 569-571; Erhardt, A. et al., IL-10, regulatory T cells, and Kupffer cells mediate tolerance in concanavalin A-induced liver injury in mice. *Hepatology,* 2007, 475-485).

EXAMPLE 19

Inhibition of Parkinson's Disease Pathology in Rats

Model A: Systemic Exposure to LPS to Promote Neurodegeneration

Parkinson's disease is a pathological, age-related neurodegenerative disorder, characterized by a specific and progressive degeneration of dopaminergic neurons. Peripheral exposure to LPS, a potent inducer of inflammation in rodents, has been shown to result in neuroinflammation, persistent microglial activation, delayed and progressive dopamine neurons loss in the substantia nigra, similar to that observed in Parkinson's Disease. Recent evidence has implicated inflammation in the neurodegeneration of nigrostriatal dopaminergic neurons, and LPS was shown to promote it (see Qin, L. et al. Systemic LPS causes chronic neuroinflammation and progressive neurodegeneration, 2007 *Glia,* 453-462).

Long Evans rats were dosed intraperitoneal (ip) with 2 mg/kg of Compound 9 or vehicle 1 h before the first (time 0 h) and the third (time 24 h) injections of LPS. At time 0 the animals received a dose of 10 mg/kg of LPS. At time 6 and 24 h the animals were dosed with 3 mg/kg of LPS solution, ip. 30 h after the first LPS injection, the animals received ip injections of lethabarb and were transcardially perfused with 400 ml PBS at 4° C. followed by 400 ml of 4% paraformaldehyde (PFA). The brains were post fixed overnight in 4% PFA at 4° C. followed by 20% sucrose solution for 24 h. 30 μm sections were collected and stained for immunofluorescence, immunohistochemistry and western blot analysis. The group treated with Compound 9 showed reduced neutrophil infiltration in the dorso-lateral striatum and hippocampus, and a reduction of microglial cell recruitment and activation (dendrites length, surface and volume) in the substantia nigra and dorso-lateral striatum (FIG. 7).

Model B: Localized Exposure to LPS to Promote Neurodegeneration

Direct injection of LPS in selected areas of the brain can be performed in order to induce a localized inflammatory response in the brain. The dopaminergic neurons are more vulnerable to inflammation based neurotoxicity, and the local LPS injections in relevant areas such as substantia nigra and striatum have been used as a model for Parkinson's Disease (see Liu, M., & Bing, G. Lipopolysaccharide animal models for Parkinson's disease. *Parkinson's disease,* 2011, 327089; Choi, D.-Y. et al. Striatal neuroinflammation promotes Parkinsonism in rats. *PloS one,* 2009, 4(5), e5482). LPS has also been shown to promote nigral dopaminergic neuron degeneration (see Machado, A. et al., Inflammatory animal model for Parkinson's Disease: The intranigral injection of LPS induced the inflammatory process along with the selective degeneration of nigrostriatal dopaminergic neurons. *ISRN Neurology,* 2011, 1-16).

A solution containing 2 μL of 1 mg/mL of LPS is injected in the left substantia nigra of female rats previously anesthetized. Animals are treated with 0.1-100 mg/Kg of compound and the results show up to 80% decreases in inflammation with less activation of microglia as compared to control animals. Vehicle treated animals are accompanied by loss of dopaminergic neurons and decreases of the intracellular content of dopamine (DA), effects which are significantly inhibited by the compound. The average loss of the dopaminergic system in the vehicle treated groups is around 35%, whilst in the compound treated group it is <20%.

EXAMPLE 20

Inhibition of Inflammation Associated with Stroke in Mice

The development of the brain tissue damage in stroke is composed of an immediate component followed by an inflammatory response with secondary tissue damage after reperfusion. The ischemia/reperfusion model mimics the tissue damage as well as inflammatory component (see Hase, Y. et al., Cilostazol, a phosphodiesterase inhibitor, prevents no-reflow and haemorrhage in mice with focal cerebral ischemia. *Exp. Neurol.,* 2012, 233(1), 523). Mice are subjected to middle cerebral artery occlusion/reperfusion surgery by introducing a nylon monofilament into the right common carotid artery (CCA). It is carefully advanced to 11 mm from the carotid artery bifurcation and a proximal occlusion of the right middle cerebral artery is established. After 90 min occlusion, the filament is withdrawn to allow reperfusion for another 22.5 hr. Animals are treated with compound 0.1-100 mg/Kg and show up to 50% reduction in platelet aggregation and leukocyte plugging in the micro vessels. Treatment significantly reduces mortality rate with >80% of animal survival.

EXAMPLE 21

Inhibition of Acute Lung Inflammation in the LPS Driven Model

Inflammation was induced by instillation of LPS into the lungs of mice using an tracheal surgery challenge method (see Innate immune responses to LPS in mouse lung are suppressed and reversed by neutralization of GM-CSF via repression of TLR-4. *Am. J. Physiol. Lung Cell. Mol. Physiol.,* 2004, L877-85; and Harrod, K. S., A. D. Mounday, and J. A. Whitsett, Adenoviral E3-14.7K protein in LPS-induced lung inflammation. *Am. J. Physiol. Lung Cell. Mol. Physiol.,* 2000, 278, L631-9). Briefly, 1 hour after treatment with 10 mg/kg of Dexamethasone or 2 mg/kg of Compound 9, mice were anesthetized, a midline incision was made in the neck, the muscle layers separated by blunt dissection, and 1 ml/kg LPS (20 mg/kg) or vehicle injected into the trachea. The incision was closed with wound clips and the mice returned to cages.

Six hours after LPS/saline injection, the mice were anesthetized, the wound clips removed, the trachea was cannulated with a 23G blunt needle, and the lungs lavaged eight times with 0.5 ml heparinized saline. The lavage was pooled, gently inverted, and a sample retained for white blood cell (WBC) differential analysis. The remainder of the lavage was centrifuged, the supernatants used for cytokine analysis. Compound 9 showed a significant reduction in neutrophil infiltration and a diminution of IL-6 and TNF-α levels compared to controls (FIG. 8).

EXAMPLE 22

Inhibition of Lung Allergic Inflammation of Viral Infected Mice

Early-life respiratory viral infections, notably with respiratory syncytial virus (RSV), increase the risk of subsequent development of childhood asthma. Infection with pneumonia virus of mice (PVM), which belongs to the same family (Paramyxoviridae) and genus (Pneumovirus) as RSV, provides a model of RSV disease (see Rosenberg, H. F. et al., The pneumonia virus of mice infection model for severe respiratory syncytial virus infection: identifying novel targets for therapeutic intervention. *Pharmacol. Ther.*, 2005, 105, 1-6). Allergic airway inflammation, including recruitment of eosinophils, is prominent in animals that are neonatally infected with PVM and then challenged with OVA antigen (see Siegle, J. S. et al., Early-life viral infection and allergen exposure interact to induce an asthmatic phenotype in mice. *Respir. Res.*, 2010, 11, 14).

On both days 1 and 2 of life, mice are intranasally inoculated with 2 pfu (PVM J3666 strain ~1×10$^5$ pfu/mL) in 5 μL phosphate buffered saline (PBS) on the external nares. Control animals are sham-infected with PBS alone. Intranasal sensitisation to OVA is performed either at days 1 and 2 of life or at days 28 and 29, with 5 μg OVA/5 μL PBS or 100 μg/40 μL respectively. Mice receive low-level aerosol challenge with ovalbumin (mass concentration of ≈3 mg/m3 of ovalbumin for 30 min/day, 3 days/week for 4 weeks). This is followed by a single moderate-level challenge (≈30 mg/m$^3$ for 30 minutes) to induce the changes of an acute exacerbation. The purpose of this study is to assess anti-inflammatory effect of the compound (0.1-100 mg/kg) in mice that are predisposed to the development of features of asthma due to early-life infection.

Bronchoalveolar lavage (BAL) is performed for recovery of airway luminal cells. This procedure is achieved by intratracheal instillation of 800 μL of PBS/mouse. The total number of leukocytes is counted using a haemocytometer. Cytospin slides are prepared from BAL fluid and then stained with Wright-Giemsa stain for differential cell count. Cells are classified into mononuclear cells, eosinophils, neutrophils and lymphocytes according to standard morphologic criteria and at least 200 cells were counted per slide under light microscopy. For lung histology, lungs are perfused, inflated and fixed in 10% buffered formalin before immunohistochemichal analysis. The extent of the leukocyte infiltrate is scored as 0, minimal or no inflammation; 1, mild inflammation, only perivascular or peribronchiolar; 2, moderate inflammation, some parenchymal involvement; 3, marked inflammation, widespread parenchymal involvement; 4, severe inflammation as previously described. Compounds are administered at 0.1 mg/kg-100 mg/kg and animals show a reduction of 40-80% in neutrophil infiltration, diminution of IL-6 and TNFα of up to 30% compared to controls.

EXAMPLE 23

Inhibition of Exacerbation in an HDM-Induced Asthma Model

Respiratory infections, which are predominantly caused by rhinovirus in people with asthma, exacerbate airway inflammation and further contribute to disease burden and healthcare cost. The rhinovirus exacerbated house dust mite (HDM) model was used to study the effect of Compound 23 in a model of allergic asthma (Collison, A. et al. The E3 ubiquitin ligase midline 1 promotes allergen and rhinovirus-induced asthma by inhibiting protein phosphatase 2A activity. *Nat. Med.* 2013, 19(2): 232-7).

Figure 9A:
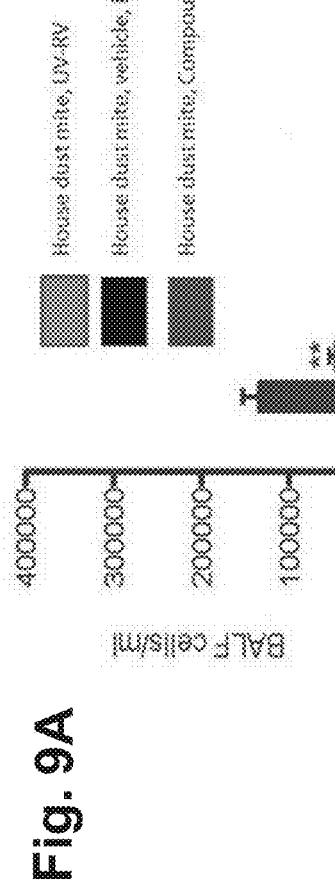
FIGS. 9A & 9B show the ability of Compound 23 to reduce neutrophil migration to the lung and airway hyper reactivity in a mouse model of allergic asthma: Inhibition of neutrophils in broncheoalveolar lavage fluid (BALF) (FIG. 9A); Inhibition of methacholine-induced hyper reactivity (FIG. 9B).
Figure 9B:
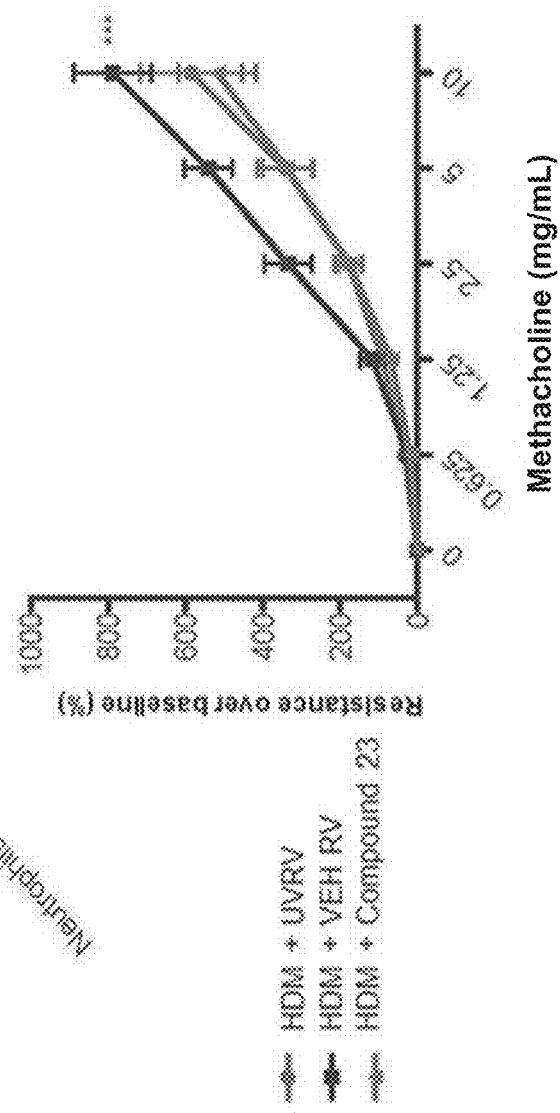

Mice were sensitized and challenged by exposing them intranasally to crude HDM extract (50 μg daily at days 0, 1 and 2 followed by four exposures of 5 μg HDM daily from day 14 to day 17 delivered in 50 μl of sterile saline). Animals were infected (day 18, 1 d after last HDM extract challenge) with 50 μl infective or ultraviolet light (UV)-inactivated RV1B41 (2.5×106 median tissue culture infective dose) intranasally. Compounds were dosed at 0.1-100 mg/kg 1 hour prior to rhinovirus challenge. Mice were killed 24 h after the last allergen or rhinovirus challenge. Cytospin slides were prepared from Bronchoalveolar lavage fluid and then stained with Wright-Giemsa stain for differential cell count. Cells are classified into mononuclear cells, eosinophils, neutrophils and lymphocytes according to standard morphologic criteria and at least 200 cells were counted per slide under light microscopy. Animals treated with Compound 23 at 6 mg/kg showed a significant reduction in neutrophil infiltrate in the BALF (FIG. 9A) and reduced airway hyper reactivity in response to metacholine challenge back to that of the control group (FIG. 9B).

EXAMPLE 24

Inhibition of Cutaneous Inflammation in the SCID Mouse Model of Psoriasis

Psoriasis is a common inflammatory skin disease characterized by abnormal epithelial differentiation, extensive capillary formation in the papillary dermis, and accumulation of inflammatory leukocytes including T lymphocytes, NK lymphocytes, and granulocytes. Transplantation of human skin onto immunocompromised mice (severe combined immunodeficiency [SCID] mice) provides a model to study psoriasis. Using this approach, epidermal thickening, extensive rete peg formation, and presence of inflammatory cells are maintained for an extended period in the transplanted skin (see Zeigler, M. et al., Anti-CD11a ameliorates disease in the human psoriatic skin-SCID mouse transplant model: comparison of antibody to CD11a with Cyclosporin A and clobetasol propionate. *Lab. Invest,* 2001, 81, 1253-1261 and Nickoloff, B. J. et al., Severe combined immunodeficiency mouse and human psoriatic skin chimeras. Validation of a new animal model. *Am. J. Pathol.,* 1995, 146, 580-588).

SCID mice (6-8 weeks old) are prepared for orthotopical skin xenografts. Human skin xenografts (measuring 1.5× 1.5×0.05 cm) are sutured to the flank area of each SCID mouse with absorbable Dexon suture. Dressings are changed every 2 days, and animals are maintained pathogen-free throughout the study. Human skin/SCID mice chimeras are sacrificed at 4 or 6 weeks after xenograft transplantation (as this period of time assured adequate acceptance and healing). Xenograft biopsies are processed for cytokine ELISA as well as histopathology analysis. After transplantation, compound treated group (0.1-100 mg/kg) show a 20-50% reduction in inflammation in the dermis and epidermis, compared with the vehicle-treated group. In addition, cytokines such as IL-6 and TNFα are inhibited by up to 80% by compound treatment.

EXAMPLE 25

Antimicrobial Activity—*Klebsiella pneumoniae* Infection

The efficacy of the compound was investigated in a model of pulmonary infection caused by the Gram-negative bacterium *Klebsiella pneumoniae*. The outcomes were the differences between compound and control in lethality rates, bacterial counts and inflammatory indices following pulmonary infection of mice (see Soares, A. C. et al., Dual function of the long pentraxin PTX3 in resistance against pulmonary infection with *Klebsiella pneumoniae* in transgenic mice. *Microbes Infect.*, 2006, 8, 1321-1329.).

BALB/c mice (8 weeks old) were divided in 3 groups; 2 infected and 1 uninfected. Infected groups: Group A, animals were administered vehicle orally; Group B, animals were administered 2 mg/kg of compound orally; and Group C animals were uninfected. Broncheoalveolar lavage fluid (BALF) was collected to determine total number of leukocytes. Cytospin slides were prepared from BAL fluid and then stained with Wright-Giemsa stain for differential cell count. Cells are classified into mononuclear cells, eosinophils, neutrophils and lymphocytes according to standard morphologic criteria and at least 200 cells were counted per slide under light microscopy. For bacterial counts, lung was homogenised, serially diluted and plated on MacConkey agar plates. Colony forming units were counted at the end of 24 hours incubation at 37° C. Animal survival rates were recorded for the next 10 days.

Figure 10B:
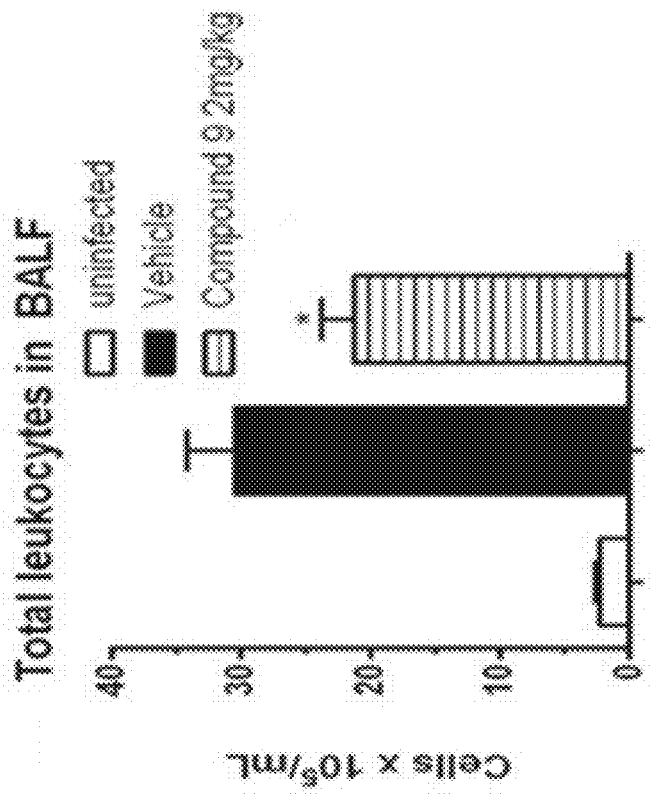
FIGS. 10A & 10B show the ability of Compound 9 to reduce leukocyte migration into the lung and protect against mortality in a mouse model of bacterial lung infection: Reduction of mortality (FIG. 10A); Inhibition of leukocytes in broncheoalveolar lavage fluid (BALF) (FIG. 10B).
Figure 10A:
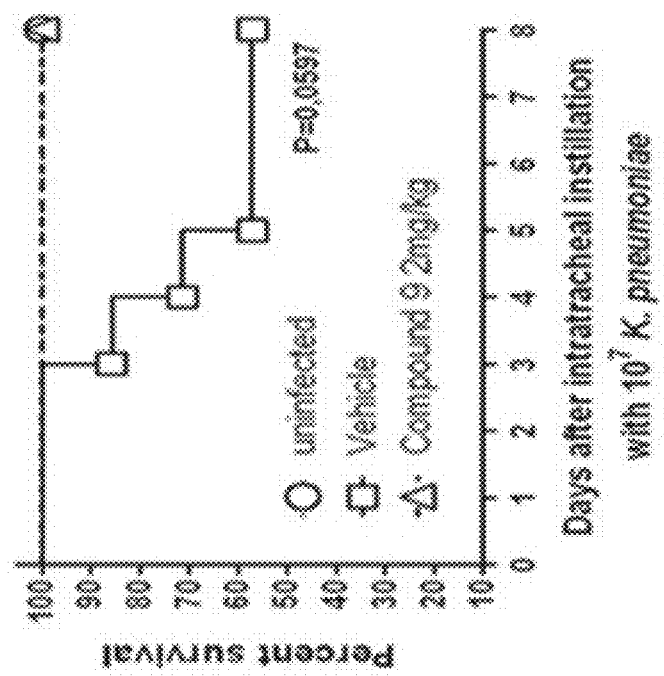

Compared with the vehicle-treated group that showed a 45% lethality incidence, Compound 23 treated mice showed a statistically significant reduction in lethality with 100% of mice surviving (p=0.0597) after 8 days (FIG. 10A). In addition, the inhibitory effect of Compound 23 on the inflammatory component of disease was seen in reduced leukocyte infiltrate to the BALF (FIG. 10B).

EXAMPLE 26

Inhibition of Chronic Obstructive Pulmonary Disease

Chronic Obstructive Pulmonary Disease (COPD) is a debilitating disorder of the lung. The disease is characterized by chronic airway inflammation, mucus hypersecretion, airway remodeling, and emphysema, which lead to reduced lung function and breathlessness. Airflow limitation is usually both progressive and associated with an abnormal inflammatory response of the lungs to noxious gases and particles. Cigarette smoke elicits a repetitive inflammatory insult that is believed to, through the actions of mediators such as proteinases, lead to structural and functional changes in the lung. Moreover, patients with COPD are more susceptible to respiratory tract infections (see Beckett, E. L., A new short-term mouse model of chronic obstructive pulmonary disease identifies a role for mast cell tryptase in pathogenesis. *J Allergy Clin Immunol.* 2013 March; 131(3): 752-762.e7; Guerassimov, A., The Development of Emphysema in Cigarette Smoke-exposed Mice Is Strain Dependent. *Am. J. Respir. Crit. Care Med.* November, 2004 (170) 974-980 and Morris, A., Comparison of Cigarette Smoke-Induced Acute Inflammation in Multiple Strains of Mice and the Effect of a Matrix Metalloproteinase Inhibitor on These Responses. *JPET* December 2008 (327) 851-862).

Figure 11:
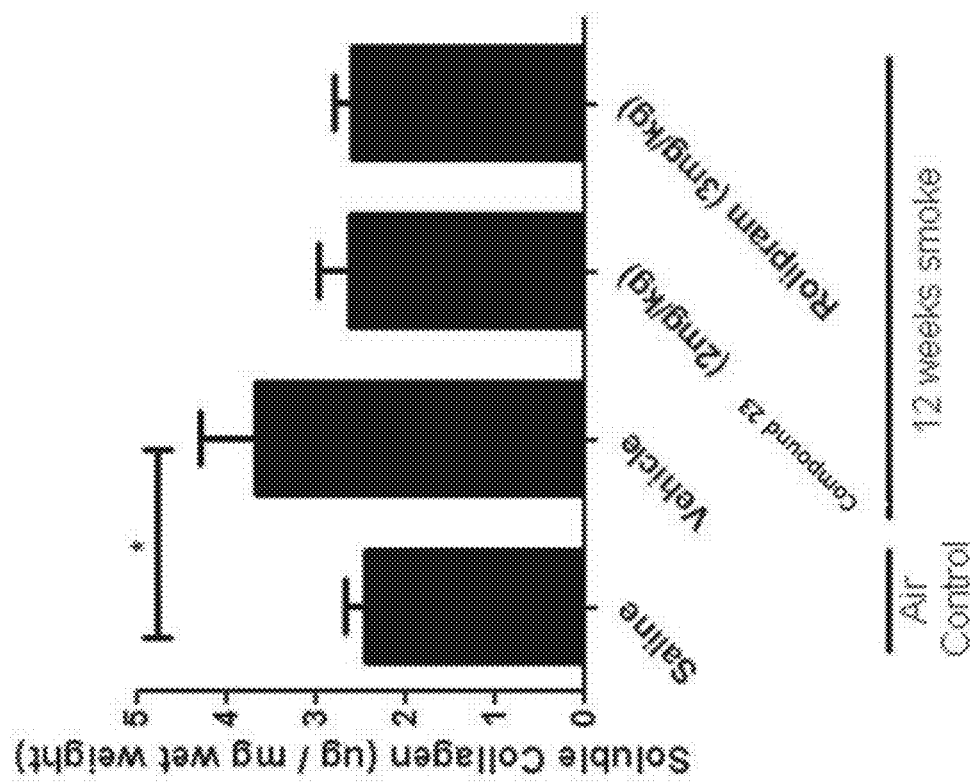
FIG. 11 shows the ability of Compound 23 to reduce the amount of soluble collagen in a mouse model of COPD.

BALB/c mice were simultaneously exposed to cigarette smoke (twelve 3R4F reference cigarettes [University of Kentucky, Lexington, Ky] twice per day and 5 times per week for 1 to 12 weeks) by using a custom-designed and purpose-built nose-only, directed-flow inhalation and smoke-exposure system (CH Technologies, Westwood, N.J.) housed in a fume and laminar flow hood. Each exposure lasted 75 minutes. Nose-only exposure was achieved by using specialized containment tubes that delivered smoke and normal air directly to the animal's nose. This protocol allowed a more intensive delivery of smoke than whole-body exposure systems. For the first 2 days, mice were exposed to 1 session of smoking with 12 puffs from each cigarette to allow acclimatization. Smoke was delivered in 2-second puffs, with 30 seconds of normal air between each puff. After day 2, the mice were subjected to 2 sessions in which they were exposed to the smoke from 12 cigarettes (morning and afternoon, separated by a recovery period). Compound 23 was given at 2 mg/kg from week 6 onwards of the experimental procedure and significantly inhibited lung collagen content (FIG. 11).

EXAMPLE 27

Inhibition of $CCl_4$ Induced Liver Fibrosis

An analysis of the use of VAP-1/SSAO inhibitors to treat inflammatory/fibrotic diseases is performed through the use of a $CCl_4$ induced liver fibrosis model. Liver injury is frequently followed by complete parenchymal regeneration due to regenerative potency of hepatocytes. However, the concomitant activation of fat-storing cells leads to extracellular matrix accumulation accompanied by recurrent hepatocyte necrosis, inflammation, and regenerative processes, and causes liver fibrosis and consequently liver cirrhosis (see Natsume, M. et al., Attenuated liver fibrosis and depressed serum albumin levels in carbon tetrachloride-treated IL-6-deficient mice. *J. Leukoc. Biol.*, 1999, 66, 601-608.).

Figure 12A:
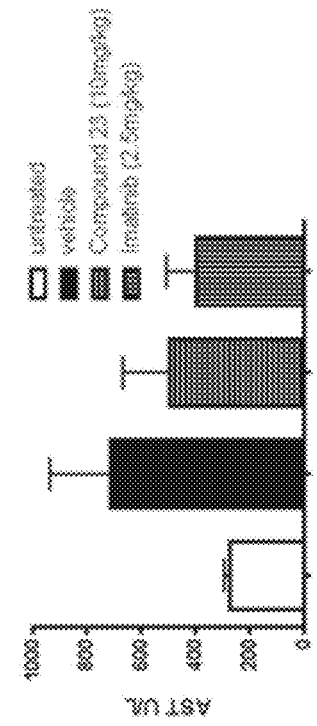
Figure 12B:
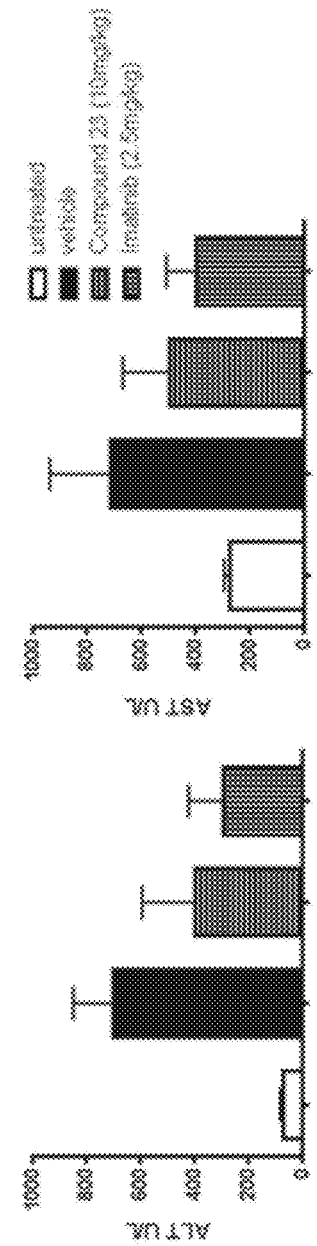
Figure 12C:
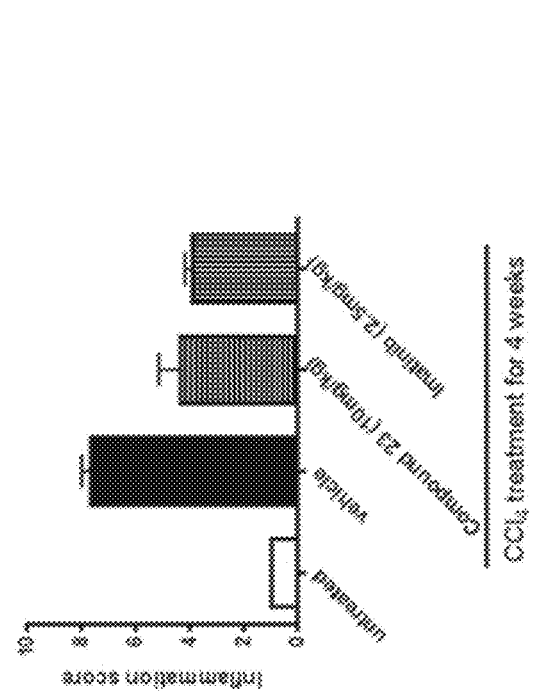
Figure 12D:
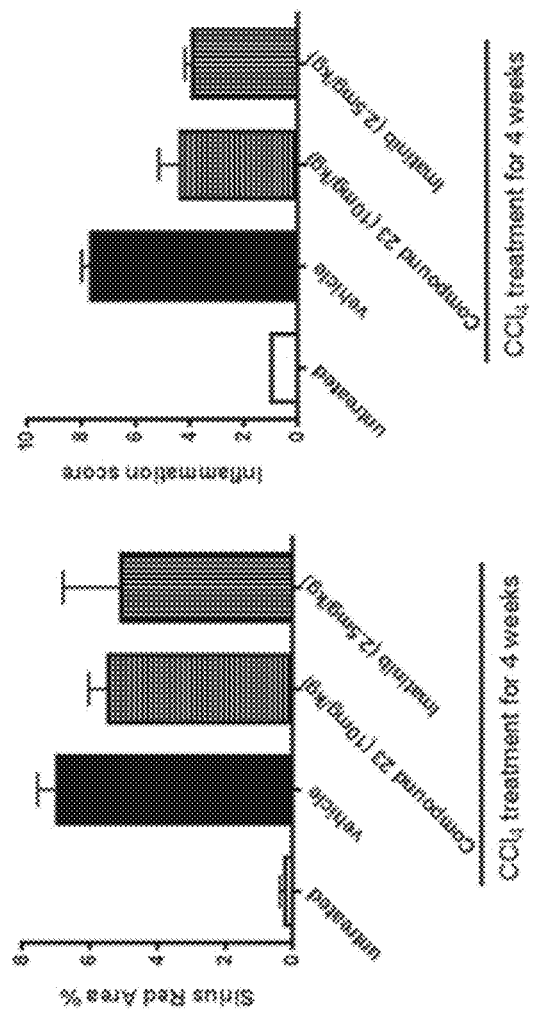

Liver fibrosis in the male Sprague Dawley (SD) rats was induced by oral application of $CCl_4$ (2.5 µL/g of $CCl_4$ olive solution, 3 times a week). Vehicle (PBS), and the positive control imatinib mesylate (2.5 mg/kg) were given to the rats from day 1 to day 28, and Compound 23 (6 mg/kg) was given to the rats from day 14 to day 28. Compound 23 demonstrated a clear trend of decreased levels of fibrotic tissue, as represented by a decrease in Sirius red staining (FIG. 12C). Moreover, Compound 23 showed liver function protective effects and a reduction in inflammation which were evidenced by significantly decreased levels of serum ALT and AST (FIGS. 12A & 12B) and a reduction in inflammatory score (12D) when compared to the $CCl_4$ only group.

EXAMPLE 28

Inhibition of Non-Alcoholic Steatohepatitis (NASH) Induced Liver Fibrosis

Figure 13A:
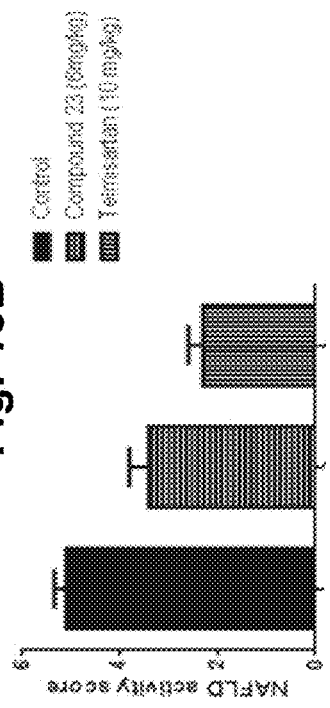
FIGS. 13A-13D show the ability of Compound 23 to reduce inflammation and fibrosis in a mouse model of fatty liver disease: Reduction of inflammation score (FIG. 13A); Reduction in non-alcoholic fatty liver disease (NAFLD) activity score (FIG. 13B); Reduction in Sirius red area (FIG. 13C); Reduction in liver triglycerides (FIG. 13D).
Figure 13B:
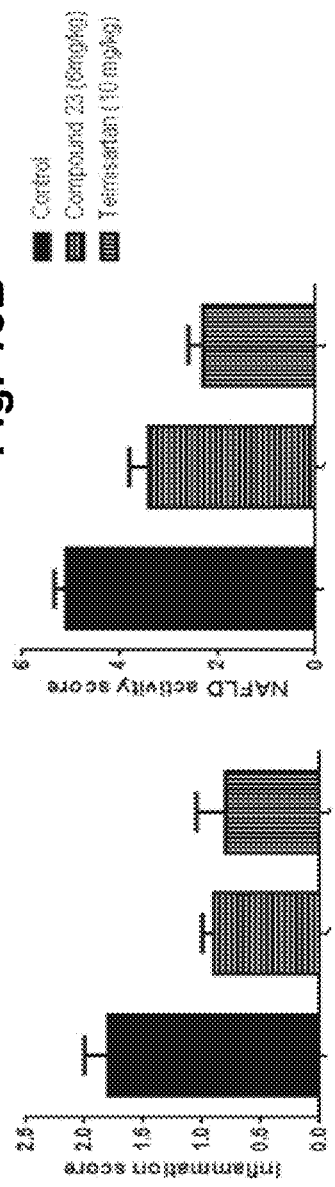
Figure 13C:
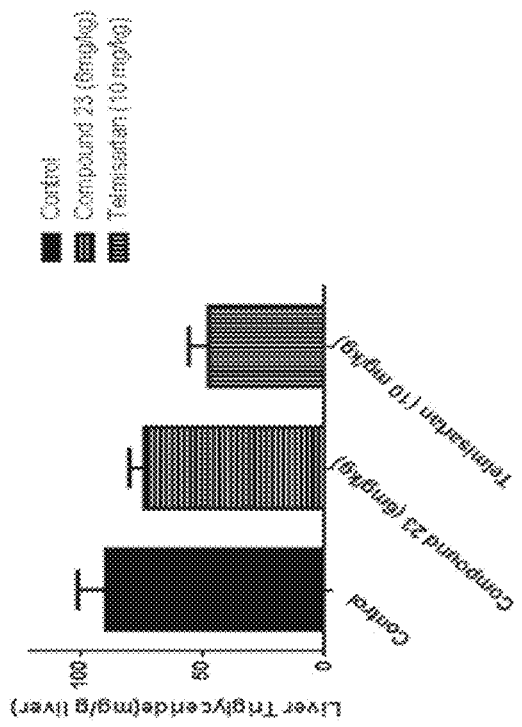
Figure 13D:
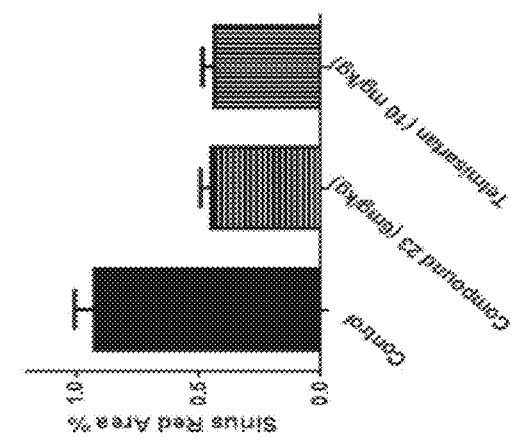

An analysis of the use of VAP-1/SSAO inhibitors to treat inflammatory/fibrotic diseases is performed through the use of a non-alcoholic steatohepatitis (NASH) induced liver fibrosis model. STAM model of NASH was induced in 30 male mice by a single subcutaneous injection of streptozotocin solution 2 days after birth and feeding with high fat diet (HFD, 57 kcal % fat) after 4 weeks of age to 10 weeks of age. From 7 weeks of age mice were orally administered daily dose of vehicle (PBS), Compound 23 (6 mg/kg) or the positive control Telmisartan (10 mg/kg) for 3 weeks. Compound 23 reduced both inflammation and non-alcoholic fatty liver disease (NAFLD) scores upon clinical examination (FIGS. 13A & 13B). Fibrosis, as evidenced by a reduction of Sirius red-positive area (FIG. 13C) was also reduced.

EXAMPLE 29

Inhibition of Uveitis

This procedure is to determine inhibition of uveitis by compound(s) according to the invention. Uveitis is a complex inflammatory eye disease that can lead to blindness. It can affect any part of the eye and is characterized by the accumulation of leukocytes in ocular tissues. Current therapies for uveitis include corticosteroids and chemotherapeutic agents to reduce inflammation. However, the grave side effects of these drugs, such as increased intraocular pressure or cytotoxicity limit their use (see Moorthy, R. S. et al., Glaucoma associated with uveitis. *Surv. Ophthalmol.,* 1997, 41, 361-394 and Lightman, S., New therapeutic options in uveitis. *Eye* 1997, 11, 222-226).

Thirty (30) Lewis albino rats were divided into four (4) groups. For three groups out of 4, ocular inflammation was induced by a single footpad injection of 1 mg/kg lipopolysaccharide (LPS from *Salmonella Typhimurium*). Compound 23 (2 mg/kg) and vehicle were administered by oral gavage (1 ml/kg) 1 hour before induction (Day 0). Reference item (dexamethasone, 2 mg/kg) was administered by intravenous injection (2.5 ml/kg) just after induction (Day 0). Ocular inflammation was assessed by clinical examination and quantification of neutrophils, eosinophils and proteins in aqueous humor, 24 h after induction.

Clinical Examination of Inflammation; Animals were examined with a slit-lamp at baseline (Day −1) then 24 h after induction (Day 1). The inflammation in each animal was graded using a scoring system as described (Devos A. et al., Systemic antitumor necrosis factor antibody treatment exacerbates Endotoxin Induced Uveitis in the rat. *Exp. Eye. Res.* 1995; 61: 667-675.). Flare, miosis and hypopion were scored for absence (0), or presence (1), iris hyperemia and cells in the anterior chamber were scored for absence (0), or mild (1) or severe presence (2). The maximum score (sum of the five parameter scores) is 7. In the group treated with Compound 23, a 33% reduction in the severity of the ocular inflammation, compared with the score observed for the vehicle group, was detected 24 hours after induction and 25 hours after oral administration (FIG. 14A).

At the end of the clinical evaluation (24 h after induction), animals were anesthetized by an intramuscular injection of a mixed solution of Rompun® (xylazine) and Imalgene® 1000 (ketamine) and euthanized by cardiac injection of overdosed pentobarbital. The aqueous humor was collected immediately for each eye.

Quantification of Cellular Infiltration in Aqueous Humor; Infiltrated neutrophils and eosinophils were manually counted in cytological preparation of aqueous humor samples diluted 10-fold with PBS before Giemsa staining. A significant diminution in eosinophils (mean±SEM: 8.9±1.7 cells/µL, n=20) was observed for the group treated with Compound 23 versus the group treated with the vehicle (p=0.033) (FIG. 14B).

EXAMPLE 30

Inhibition of Macular Degeneration

Age-related macular degeneration (AMD) is the leading cause of blindness and occurs in two major forms. The first is a geographic atrophy ('dry') form that is defined by degeneration of photoreceptors and the retinal pigmented epithelium (RPE) near the macula, the accumulation of lipofuscin (A2E), and the formation of drusen. The second is a 'wet' form that is associated with choroidal neovascularization (see Randazzo, J. et al., Orally active multifunctional antioxidants are neuroprotective in a rat model of light-induced retinal damage. *PLoS One,* 2011, 6 e21926 and Davis, S. J. et al., The Effect of Nicotine on Anti-Vascular Endothelial Growth Factor Therapy in a Mouse Model of Neovascular Age-Related Macular Degeneration. *Retina,* 2011).

Model A: Light Model

After two weeks of dark adaptation, rats from each group are exposed to damaging light for three hours to 1000 lx of cool white fluorescent light (light-damaged rats, LD). The control rats in each group are also placed into the light box apparatus for three hours, but not exposed to light (non-light-damaged rats, NLD). Oxidative stress markers were evaluated immediately after light exposure. Compound treated animals 0.1-100 mg/kg show >20% reduction in oxidative stress as seen by evaluation of neural retinas, which are dissected—following euthanasia—from the enucleated eye. For functional and morphological assessment, rats are returned to the dark environment after exposure and retinal function is assessed by ERG, 5 to 7 days later. Following ERG analysis, the rats are euthanized and the enucleated eyes are immediately processed for quantitative morphology. Compound treated group demonstrate a reduction in severity of disease as seen by decreases in morphological changes of the eyes as compares to control animals.

Model B: Laser Model

CNV is induced by laser photocoagulation in mice with an argon laser (spot size, 50 mm; duration, 0.05 seconds; power, 260 mW). Three laser spots are placed in each eye close to the optic nerve. Production of a vaporization bubble at the time of laser confirms the rupture of BM. Animals from each group are sacrificed on days 1, 3, 5, and 7 post-laser. Compared with control, the compound-treated mice (0.1-100 mg/kg) show a significant reduction in size (by 20%) and incidence of CNV (>40%) as determined by microscopy.

EXAMPLE 31

Inhibition of Cancer Progression

B16F10 melanoma cells ($4\times10^5$ cells/animal) are injected in the shaved adnominal region of the animal as described in Marttila-Ichihara, F. et al., Small-Molecule Inhibitors of Vascular Adhesion Protein-1 Reduce the Accumulation of Myeloid Cells into Tumors and Attenuate Tumor Growth in Mice. *The Journal of Immunology,* 2010, 184, 3164-3173. The growth of the tumor is followed by measuring the dimensions using electronic callipers. Tumor progression is diminished in compound treated animals (0-1.-100 mg/kg), with up to 25% less tumor growth when compared to control group. Compound treated groups show attenuated myeloid cell accumulation in the tumors, showing >40% less cell infiltration; in addition treated mice demonstrate inhibited neoangiogenesis.

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, variations can be made to provide additional compounds of Formula I and/or various methods of administration can be used. Thus, such additional embodiments are within the scope of the present invention and the following claims.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

Thus, additional embodiments are within the scope of the invention and within the following claims.

The invention claimed is:

1. A method for inhibiting the amine oxidase activity of SSAO/VAP-1 in a subject in need thereof, said method comprising administering to said subject an effective amount of a compound selected from the group consisting of:

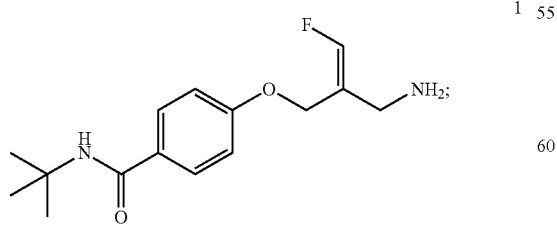

(Z)-4-(2-(Aminomethyl)-3-fluoroallyloxy)-N-tert-butylbenzamide

1

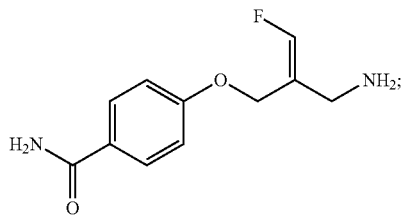

(Z)-4-(2-(Aminomethyl)-3-fluoroallyloxy)benzamide

2

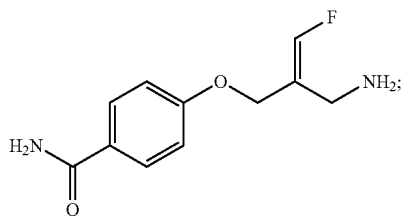

(E)-4-(2-(Aminomethyl)-3-fluoroallyloxy)benzamide

3

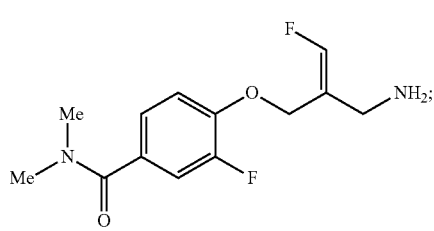

(Z)-4-(2-(Aminomethyl)-3-fluoroallyloxy)-3-fluoro-N,N-dimethylbenzamide

4

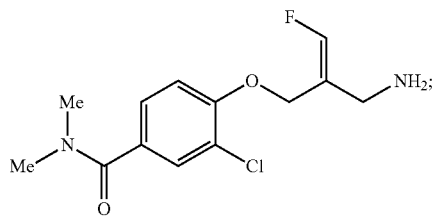

(Z)-4-(2-(Aminomethyl)-3-fluoroallyloxy)-3-chloro-N,N-dimethylbenzamide

6

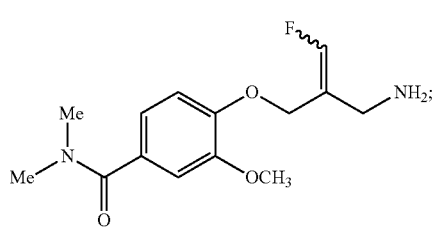

4-(2-(Aminomethyl)-3-fluoroallyloxy)-3-methoxy-N,N-dimethylbenzamide

7

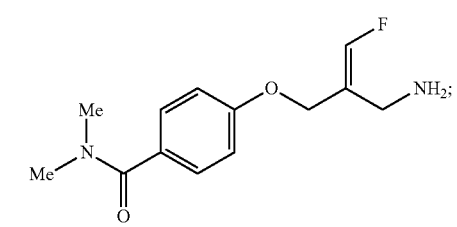

(E)-4-(2-(Aminomethyl)-3-
fluoroallyloxy)-N,N-
dimethylbenzamide

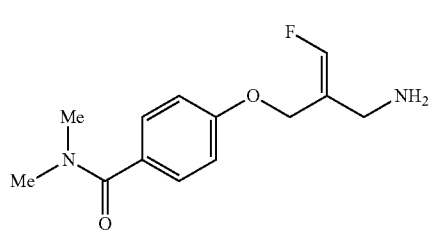

(Z)-4-(2-(Aminomethyl)-3-
fluoroallyloxy)-N,N-
dimethylbenzamide

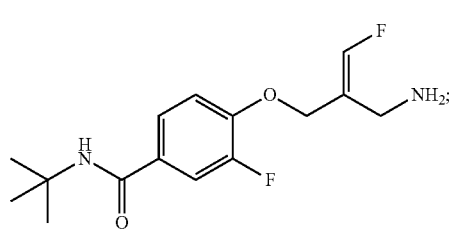

(E)-4-(2-(Aminomethyl)-3-
fluoroallyloxy)-N-tert-butyl-3-
fluorobenzamide

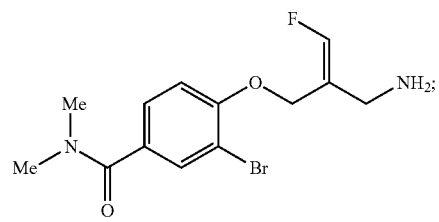

(Z)-4-(2-(Aminomethyl)-3-
fluoroallyloxy)-3-bromo-N,N-
dimethylbenzamide

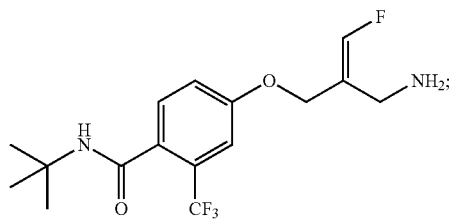

(E)-4-(2-(Aminomethyl)-3-
fluoroallyloxy)-N-tert-butyl-2-
(trifluoromethyl)benzamide

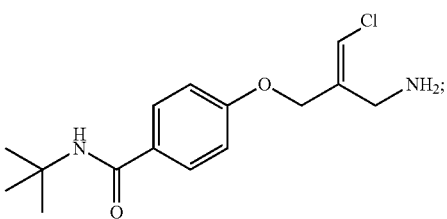

(E)-4-(2-(Aminomethyl)-3-
chloroallyloxy)-N-tert-
butylbenzamide

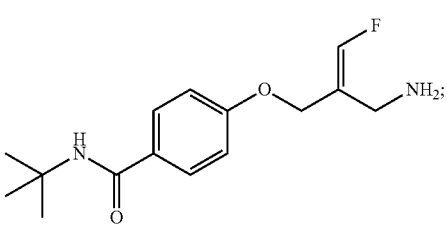

(E)-4-(2-(Aminomethyl)-3-
fluoroallyloxy)-N-tert-
butylbenzamide

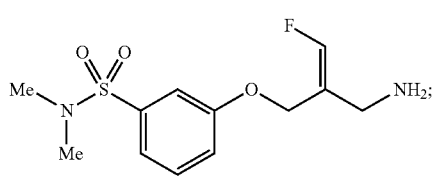

(Z)-3-(2-(Aminomethyl)-3-
fluoroallyloxy)-N,N-
dimethylbenzenesulfonamide

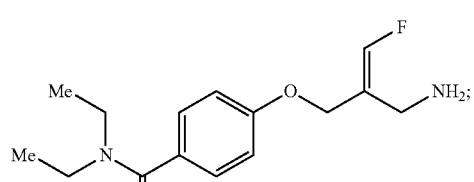

(E)-4-(2-(Aminomethyl)-3-
fluoroallyloxy)-N,N-
diethylbenzamide

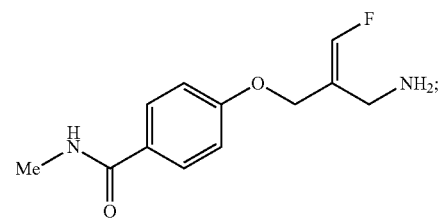

(E)-4-(2-(Aminomethyl)-3-
fluoroallyloxy)-N-
methylbenzamide

-continued

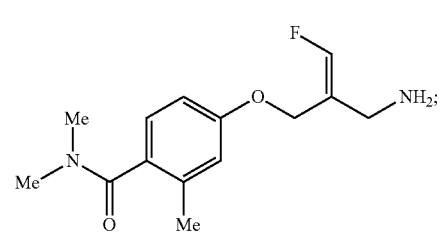

(Z)-4-(2-(Aminomethyl)-3-
fluoroallyloxy)-N,N,2-
trimethylbenzenamide

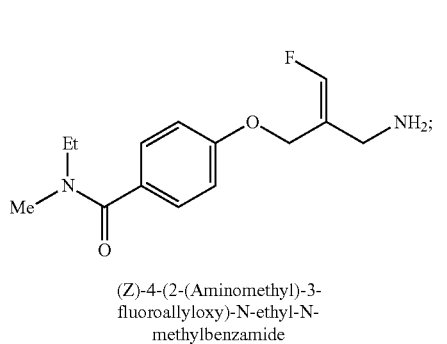

(Z)-4-(2-(Aminomethyl)-3-
fluoroallyloxy)-N-ethyl-N-
methylbenzamide

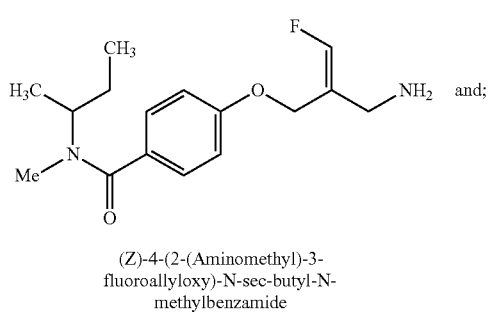

(Z)-4-(2-(Aminomethyl)-3-
fluoroallyloxy)-N-sec-butyl-N-
methylbenzamide

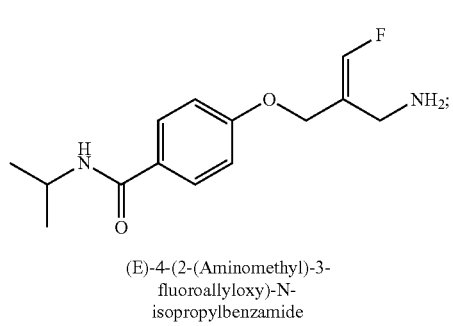

(E)-4-(2-(Aminomethyl)-3-
fluoroallyloxy)-N-
isopropylbenzamide

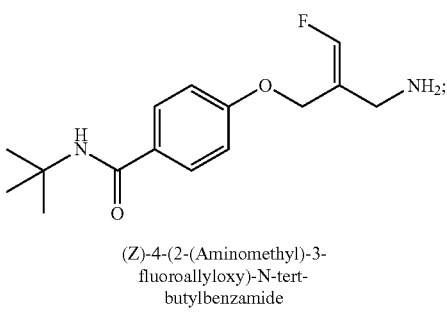

(Z)-4-(2-(Aminomethyl)-3-
fluoroallyloxy)-N-tert-
butylbenzamide

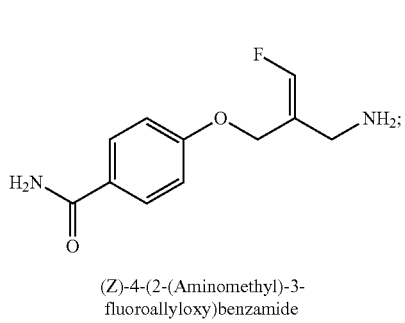

(Z)-4-(2-(Aminomethyl)-3-
fluoroallyloxy)benzamide

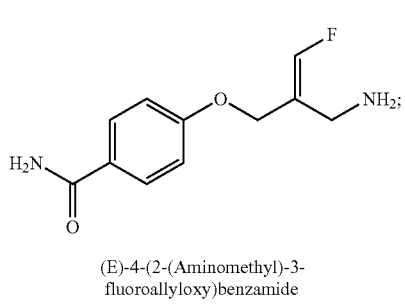

(E)-4-(2-(Aminomethyl)-3-
fluoroallyloxy)benzamide

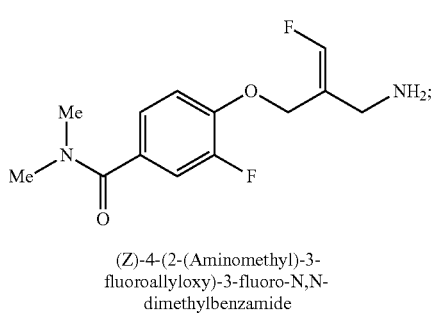

(Z)-4-(2-(Aminomethyl)-3-
fluoroallyloxy)-3-fluoro-N,N-
dimethylbenzamide

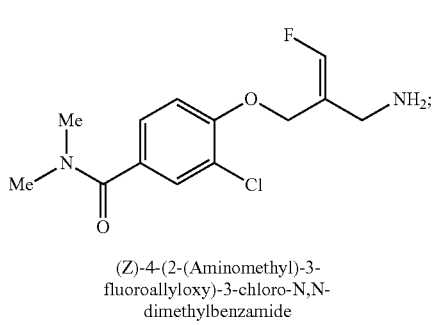

(Z)-4-(2-(Aminomethyl)-3-
fluoroallyloxy)-3-chloro-N,N-
dimethylbenzamide or a pharmaceutically acceptable salt thereof, or a composition comprising the foregoing, and at least one pharmaceutically acceptable excipient, carrier or diluent, to effect a positive therapeutic response.

2. A method for therapeutically treating a disease associated with or modulated by SSAO/VAP-1 protein, said method comprising administering to a subject in need thereof a therapeutically effective amount of a compound selected from the group consisting of:

| | |
|---|---|
| 7 | 21 |
| 4-(2-(Aminomethyl)-3-fluoroallyloxy)-3-methoxy-N,N-dimethylbenzamide | (E)-4-(2-(Aminomethyl)-3-fluoroallyloxy)-N-tert-butyl-2-(trifluoromethyl)benzamide |
| 13 | 22 |
| (E)-4-(2-(Aminomethyl)-3-fluoroallyloxy)-N,N-dimethylbenzamide | (E)-4-(2-(Aminomethyl)-3-chloroallyloxy)-N-tert-butylbenzamide |
| 18 | 23 |
| (Z)-4-(2-(Aminomethyl)-3-fluoroallyloxy)-N,N-dimethylbenzamide | (E)-4-(2-(Aminomethyl)-3-fluoroallyloxy)-N-tert-butylbenzamide |
| 19 | 15 |
| (E)-4-(2-(Aminomethyl)-3-fluoroallyloxy)-N-tert-butyl-3-fluorobenzamide | (Z)-3-(2-(Aminomethyl)-3-fluoroallyloxy)-N,N-dimethylbenzenesulfonamide |
| 20 | 24 |
| (Z)-4-(2-(Aminomethyl)-3-fluoroallyloxy)-3-bromo-N,N-dimethylbenzamide | (E)-4-(2-(Aminomethyl)-3-fluoroallyloxy)-N,N-diethylbenzamide |

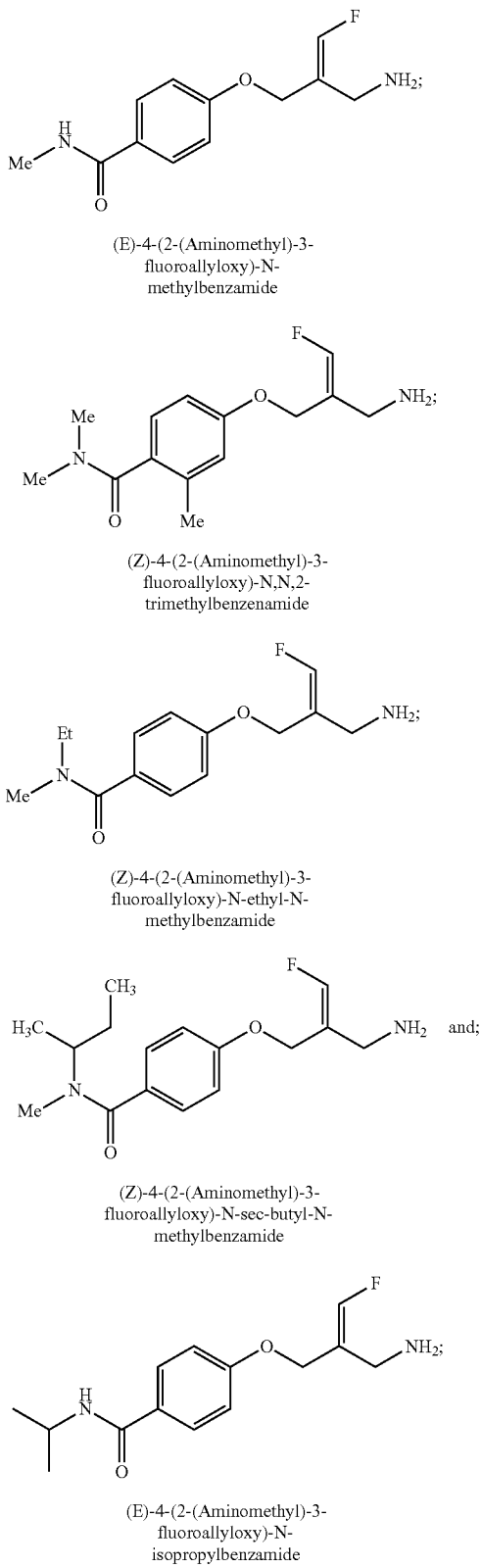

(E)-4-(2-(Aminomethyl)-3-fluoroallyloxy)-N-methylbenzamide (Z)-4-(2-(Aminomethyl)-3-fluoroallyloxy)-N,N,2-trimethylbenzenamide (Z)-4-(2-(Aminomethyl)-3-fluoroallyloxy)-N-ethyl-N-methylbenzamide (Z)-4-(2-(Aminomethyl)-3-fluoroallyloxy)-N-sec-butyl-N-methylbenzamide (E)-4-(2-(Aminomethyl)-3-fluoroallyloxy)-N-isopropylbenzamide or a pharmaceutically acceptable salt thereof, or a composition comprising the foregoing, and at least one pharmaceutically acceptable excipient, carrier or diluent.

3. The method of claim 2 wherein the disease is inflammation.

4. The method of claim 3 wherein said inflammation is associated with liver disease.

5. The method of claim 3 wherein said inflammation is associated with respiratory disease.

6. The method of claim 5 wherein said inflammation is associated with cystic fibrosis.

7. The method of claim 5 wherein said inflammation is associated with asthma or chronic obstructive pulmonary disease.

8. The method of claim 3 wherein said inflammation is associated with ocular disease.

9. The method of claim 2 wherein the disease is a diabetes-induced disease selected from the group consisting of diabetic nephropathy, glomerulosclerosis, diabetic retinopathy, non-alcoholic fatty liver disease and choroidal neovascularisation.

10. The method of claim 2 wherein the disease is a neuroinflammatory disease.

11. The method of claim 2 wherein the disease is fibrosis.

12. The method of claim 2 wherein the disease is cancer.

13. The method of claim 11, wherein the fibrosis is selected from the group consisting of cystic fibrosis, liver fibrosis, liver cirrhosis, kidney fibrosis, scleroderma, idiopathic pulmonary fibrosis and radiation-induced fibrosis.

14. The method of claim 2, wherein the disease is a non-alcoholic fatty liver disease.

15. The method of claim 2, wherein the disease is a non-alcoholic steatohepatitis (NASH).

16. The method of claim 2, wherein the disease is an alcohol induced fibrosis leading to cirrhosis of the liver.

17. The method of claim 2, wherein the disease is diabetic retinopathy.

18. The method according to claim 1, wherein said compound is selected from the group consisting of:
(E)-4-(2-(Aminomethyl)-3-fluoroallyloxy)benzamide;
(E)-4-(2-(Aminomethyl)-3-fluoroallyloxy)-N,N-diethylbenzamide;
(E)-4-(2-(Aminomethyl)-3-fluoroallyloxy)-N-methylbenzamide; and
(E)-4-(2-(Aminomethyl)-3-fluoroallyloxy)-N-tent-butylbenzamide,
or a pharmaceutically acceptable salt thereof.

19. The method according to claim 2, wherein said compound is (E)-4-(2-(Aminomethyl)-3-fluoroallyloxy)benzamide, or a pharmaceutically acceptable salt thereof.

20. The method according to claim 19, wherein said compound is (E)-4-(2-(Aminomethyl)-3-fluoroallyloxy)benzamide hydrochloride.

21. The method according to claim 2, wherein said compound is (E)-4-(2-(Aminomethyl)-3-fluoroallyloxy)-N,N-diethylbenzamide, or a pharmaceutically acceptable salt thereof.

22. The method according to claim 21 wherein said compound is (E)-4-(2-(Aminomethyl)-3-fluoroallyloxy)-N,N-diethylbenzamide hydrochloride.

23. The method according to claim 2, wherein said compound is (E)-4-(2-(Aminomethyl)-3-fluoroallyloxy)-N-methylbenzamide, or a pharmaceutically acceptable salt thereof.

24. The method according to claim 23, wherein said compound is (E)-4-(2-(Aminomethyl)-3-fluoroallyloxy)-N-methylbenzamide hydrochloride.

25. The method according to claim 2, wherein said compound is (E)-4-(2-(Aminomethyl)-3-fluoroallyloxy)-N-tert-butylbenzamide, or a pharmaceutically acceptable salt thereof.

26. The method according to claim 25, wherein said compound is (E)-4-(2-(Aminomethyl)-3-fluoroallyloxy)-N-tert-butylbenzamide hydrochloride.

\* \* \* \* \*